(12) United States Patent
Bier et al.

(10) Patent No.: US 11,944,424 B2
(45) Date of Patent: Apr. 2, 2024

(54) DYNAMIC 129XE GAS EXCHANGE SPECTROSCOPY

(71) Applicant: Duke University, Durham, NC (US)

(72) Inventors: Elianna Bier, Durham, NC (US);
Bastiaan Driehuys, Chapel Hill, NC (US); Ziyi Wang, Durham, NC (US); Sudarshan Rajagopal, Chapel Hill, NC (US)

(73) Assignee: Duke University, Durham, NC (US)

( * ) Notice: Subject to any disclaimer, the term of this patent is extended or adjusted under 35 U.S.C. 154(b) by 884 days.

(21) Appl. No.: 16/406,630

(22) Filed: May 8, 2019

(65) Prior Publication Data

US 2020/0022616 A1     Jan. 23, 2020

Related U.S. Application Data

(60) Provisional application No. 62/673,175, filed on May 18, 2018.

(51) Int. Cl.
| | |
|---|---|
| *A61B 5/08* | (2006.01) |
| *A61B 5/00* | (2006.01) |
| *A61B 5/055* | (2006.01) |
| *G01R 33/54* | (2006.01) |
| *G16H 30/40* | (2018.01) |

(52) U.S. Cl.
CPC ............ *A61B 5/0813* (2013.01); *A61B 5/055* (2013.01); *A61B 5/7282* (2013.01); *G01R 33/543* (2013.01); *G16H 30/40* (2018.01); *A61B 2576/02* (2013.01)

(58) Field of Classification Search
CPC ..... A61B 5/0813; A61B 5/055; A61B 5/7282; A61B 2576/02; G01R 33/543; G16H 30/40
See application file for complete search history.

(56) References Cited

U.S. PATENT DOCUMENTS

| | | |
|---|---|---|
| 5,545,396 A | 8/1996 | Albert et al. |
| 5,642,625 A | 7/1997 | Cates, Jr. et al. |
| 5,809,801 A | 9/1998 | Cates, Jr. et al. |
| 6,346,229 B1 | 2/2002 | Driehuys et al. |
| 6,491,895 B2 | 12/2002 | Driehuys et al. |

(Continued)

FOREIGN PATENT DOCUMENTS

| | | |
|---|---|---|
| JP | 2016521859 A | 7/2016 |
| WO | 2014201230 A1 | 12/2014 |

OTHER PUBLICATIONS

Ruppert et al., "Detecting Pulmonary Capillary Blood Pulsations Using Hyperpolarized Xenon-129 Chemical Shift Saturation Recovery (CSSR) MR Spectroscopy", 2016, Magnetic Resonance in Medicine 75:1771-1780 (Year: 2016).*

(Continued)

*Primary Examiner* — Colin T. Sakamoto
*Assistant Examiner* — Andrew W Begeman
(74) *Attorney, Agent, or Firm* — Myers Bigel, P.A.

(57) ABSTRACT

Methods and systems with $^{129}$Xe dynamic spectroscopy with a fitting function that includes one or more non-Lorentzians, optionally with a barrier Voigt, and signal processing for identifying cardiogenic oscillations for evaluating disease states, use in drug discovery or monitoring disease status.

49 Claims, 30 Drawing Sheets
(7 of 30 Drawing Sheet(s) Filed in Color)

(56) References Cited

U.S. PATENT DOCUMENTS

| | | | |
|---|---|---|---|
| 6,696,040 | B2 | 2/2004 | Driehuys |
| 6,991,777 | B2 | 1/2006 | Driehuys et al. |
| 8,911,709 | B2* | 12/2014 | Driehuys ............ G01R 33/5601 703/11 |
| 2004/0005273 | A1* | 1/2004 | Driehuys ............... G01R 33/46 424/9.3 |
| 2010/0280358 | A1 | 11/2010 | Mata et al. |
| 2013/0208970 | A1* | 8/2013 | Fujisawa ............... G16H 50/20 382/128 |
| 2017/0007116 | A1* | 1/2017 | Samec .................. A61B 3/024 |

OTHER PUBLICATIONS

Norquay et al., "129Xe Chemical Shift in Human Blood and Pulmonary Blood Oxygenation Measurement in Humans Using Hyperpolarized 129Xe NMR", 2017, Magnetic Resonance in Medicine 77:1399-1408 (Year: 2017).*

Robertson et al., "Quantitative Spectral Contrast in Hyperpolarized 129-Xe Pulmonary MRI", 2016 (Year: 2016).*

Rowland et al., "Spectral Improvement by Fourier Thresholding of in vivo Dynamic Spectroscopy Data", 2016 Magn Reson Med; 76(3): 978-985 (Year: 2016).*

Olschewski et al., "Inhaled Prostacyclin and Iloprost in Severe Pulmonary Hypertension Secondary to Lung Fibrosis", 1999, Am J Respir Crit Care Med, 160:600-607 (Year: 1999).*

Kaushik et al., "Measuring Diffusion limitation with a perfusion-limited gas Hyperpolaroized 129-Xe gas-transfer spectroscopy in patients with idiopathic pulmonary fibrosis", 2014, J Appl Physiol 117: 577-585 (Year: 2014).*

Kaushik et al., "Single-Breath Clinical Imaging of Hyperpolarized129Xein the Airspaces, Barrier, and Red Blood Cells Using an Interleaved 3D Radial 1-Point Dixon Acquisition", 216, Magnetic Resonance in Medicine 75:1434-1443 (Year: 2016).*

Robertson et al. "Uncovering a Third Dissolved-Phase129Xe Resonance in the Human Lung: Quantifying Spectroscopic Features in Healthy Subjects and Patients With Idiopathic Pulmonary Fibrosis", Nov. 8, 2016, Magnetic Resonance in Medicine, vol. 78, p. 1306-1315 (Year: 2016).*

Chang et al., "Quantification of Human Lung Structure and Physiology Using Hyperpolarized129Xe", 2014, Magnetic Resonance in Medicine, vol. 71, p. 339-344 (Year: 2014).*

Marshall et al. "Use of Voigt Lineshape for Quantification of in Vivo 'H Spectra", 1997, Magnetic Resonance in Medicine, vol. 37, p. 651-657 (Year: 1997).*

Bier et al. "Characterizing the Temporal Dynamics of 129Xe Spectroscopy to Uncover the Origins of Gas Exchange Impairment" 2017, Medical Physics Graduate Program Duke University (Year: 2017).*

He et al. "Extending Semiautomatic Ventilation Defect Analysis for Hyperpolarized 129Xe Ventilation MRI" Academic Radiology, 21(12):1530-1541 (2014).

Kirby et al. "Hyperpolarized 3He and 129Xe MR Imaging in Healthy Volunteers and Patients with Chronic Obstructive Pulmonary Disease" Radiology, 265(2):600-610 (2012).

International Search Report and the Written Opinion of the International Searching Authority corresponding to International Patent Application No. PCT/US2019/031660 (28 pages) (dated Nov. 19, 2019).

Robertson, Scott Haile "Quantitative Spectral Contrast in Hyperpolarized 129Xe Pulmonary MRI" Dissertation, Medical Physics Graduate Program, Duke University (239 pages) (2016); (Jan. 4, 2017; XP055633746).

Alfakih et al. "Normal Human Left and Right Ventricular Dimensions for MRI as Assessed by Turbo Gradient Echo and Steady-State Free Precession Imaging Sequences" Journal of Magnetic Resonance Imaging, 17:323-329 (2003).

Barnes et al. "Systemic manifestations and comorbidities of COPD" The European Respiratory Journal, 33(5):1165-1185 (2009).

Bier et al. "Quantifying Changes in Time-Resolved Hyperpolarized 129Xe Spectroscopy among Healthy and IPF Subjects" Proceedings of the International Society of Magnetic Resonance in Medicine, 25th ISMRM Annual Meeting and Exhibition, abstract 2152 (3 pages) (2017).

Bier et al. "A protocol for quantifying cardiogenic oscillations in dynamic (129) Xe gas exchange spectroscopy: The effects of idiopathic pulmonary fibrosis" NMR in Biomedicine, 32(1):e4029 (2019).

Celli et al. "Standards for the diagnosis and treatment of patients with COPD: a summary of the ATS/ERS position paper" The European Respiratory Journal, 23(6):932-946 (2004).

Chang, Yulin V. "MOXE: A model of gas exchange for hyperpolarized 129Xe magnetic resonance of the lung" Magnetic Resonance in Medicine, 69(3):884-890 (2013).

Chen et al. "Tissue-blood partition coefficient for xenon: temperature and hematocrit dependence" Journal of Applied Physiology: Respiratory, Environmental and Exercise Physiology, 49(2):178-183 (1980).

Chen et al. "Spatially resolved measurements of hyperpolarized gas properties in the lung in vivo. Part I: Diffusion coefficient" Magnetic Resonance in Medicine, 42(4):721-728 (1999).

Cherubini et al. "Hyperpolarised xenon in biology" Progress in Nuclear Magnetic Resonance Spectroscopy, 42:1-30 (2003).

Cleveland et al. "Hyperpolarized 129 Xe MR Imaging of Alveolar Gas Uptake in Humans" PLoS One, 5(8):e12192 (2010).

Cleveland et al. "3D MR Imaging of Impaired Hyperpolarized 129Xe Uptake in a Rat Model of Pulmonary Fibrosis" NMR in Biomedicine, 27(12):1502-1514 (2014).

Cosgrove et al. "Barriers to timely diagnosis of interstitial lung disease in the real world: the INTENSITY survey" BMC Pulmonary Medicine, 18(9):1-9 (2018).

Dahhan et al. "Abnormalities in hyperpolarized 129Xe magnetic resonance imaging and spectroscopy in two patients with pulmonary vascular disease" Pulmonary Circulation, 6(1):126-131 (2016).

De Simone et al. "Stroke Volume and Cardiac Output in Normotensive Children and Adults" Circulation, 95(7):1837-1843 (1997).

Divo et al. "Comorbidities and Risk of Mortality in Patients with Chronic Obstructive Pulmonary Disease" American Journal of Respiratory and Critical Care Medicine, 186(2):155-161 (2012).

Doyle et al. "SIFT, a Postprocessing Method That Increases the Signal-to-Noise Ratio of Spectra Which Vary in Time" Journal of Magnetic Resonance, Series B, 103(2):128-133 (1994).

Driehuys et al. "Chronic Obstructive Pulmonary Disease: Safety and Tolerability of Hyperpolarized 129Xe MR Imaging in Healthy Volunteers and Patients" Radiology, 262(1):279-89 (2012).

Dwyer-Lindgren et al. "Trends and Patterns of Differences in Chronic Respiratory Disease Mortality Among US Counties, 1980-2014" JAMA, 318(12):1136-1149 (2017).

Farha et al. "Loss of alveolar membrane diffusing capacity and pulmonary capillary blood volume in pulmonary arterial hypertension" Respiratory Research, 14(6):1-8 (2013).

Glazier et al. "Measurements of capillary dimensions and blood volume in rapidly frozen lungs" Journal of Applied Physiology, 26(1):65-76 (1969).

Guazzi, Marco "Alveolar Gas Diffusion Abnormalities in Heart Failure" Journal of Cardiac Failure, 14(8):695-702 (2008).

Hajari et al. "Morphometric changes in the human pulmonary acinus during inflation" Journal of Applied Physiology, 112(6):937-943 (2012).

Hawkins et al. "Heart failure and chronic obstructive pulmonary disease: the challenges facing physicians and health services" European Heart Journal, 34(36):2795-2803 (2013).

He et al. "Dose and Pulse Sequence Considerations for Hyperpolarized 129Xe Ventilation MRI" Magnetic Resonance Imaging, 33(7):877-885 (2015).

He et al. "Using Hyperpolarized 129Xe MRI to Quantify the Pulmonary Ventilation Distribution" Academic Radiology, 23(12):1521-1531 (2016).

Hoeper et al. "Elderly patients diagnosed with idiopathic pulmonary arterial hypertension: results from the COMPERA registry" International Journal of Cardiology, 168(2):871-880 (2013).

(56) References Cited

OTHER PUBLICATIONS

Janssens et al. "Physiological changes in respiratory function associated with ageing" European Respiratory Journal, 13(1):197-205 (1999).
Kaushik et al. "Probing the regional distribution of pulmonary gas exchange through single-breath gas- and dissolved-phase Xe-129 MR imaging" Journal of Applied Physiology, 115(6):850-860 (2013).
Kaushik et al. "Measuring diffusion limitation with a perfusion-limited gas—hyperpolarized 129Xe gas-transfer spectroscopy in patients with idiopathic pulmonary fibrosis" Journal of Applied Physiology, 117(6):577-585 (2014).
Kaushik et al. "Single-Breath Clinical Imaging of Hyperpolarized 129Xe in the Airspaces, Barrier, and Red Blood Cells using an Interleaved 3D Radial 1-Point Dixon Acquisition" Magnetic Resonance in Medicine, 75(4):1434-1443 (2016).
Kreuter et al. "Impact of Comorbidities on Mortality in Patients with Idiopathic Pulmonary Fibrosis" PLoS One, 11(3):e0151425 (2016).
Kruger et al. "Functional Imaging of the Lungs with Gas Agents" Journal of Magnetic Resonance Imaging, 43(2):295-315 (2016).
Lang "Recommendations for Cardiac Chamber Quantification by Echocardiography in Adults: An Update from the American Society of Echocardiography and the European Association of Cardiovascular Imaging" Journal of the American Society of Echocardiography, 28:1-39 (2015).
Lau et al. "Early detection of pulmonary arterial hypertension" Nature Reviews Cardiology, 12(3):143-55 (2015).
Lederer et al. "Idiopathic Pulmonary Fibrosis" New England Journal of Medicine, 379(8):797-798 (2018).
Mammarappallil et al. "New Developments in Imaging Idiopathic Pulmonary Fibrosis With Hyperpolarized Xenon Magnetic Resonance Imaging" Journal of Thoracic Imaging, 34(2):136-150 (2019).
Marshall et al. "Use of Voigt Lineshape for Quantification of in Vivo 1H Spectra" Magnetic Resonance in Medicine, 37(5):651-657 (1997).
Matin et al. "Chronic Obstructive Pulmonary Disease: Lobar Analysis with Hyperpolarized 129Xe MR imaging" Radiology, 282(3):857-868 (2016).
Minasian et al. "Serial pulmonary function tests to diagnose COPD in chronic heart failure" Translational Respiratory Medicine, 2(12):1-8 (2014).
Norquay et al. "Xe-129 Chemical Shift in Human Blood and Pulmonary Blood Oxygenation Measurement in Humans Using Hyperpolarized Xe-129 NMR" Magnetic Resonance in Medicine, 77(4):1399-1408 (2017).
Olson et al. "Impaired Pulmonary Diffusion in Heart Failure With Preserved Ejection Fraction" JACC—Heart Failure, 4(6):490-498 (2016).
Pike et al. "Regional Heterogeneity of Chronic Obstructive Pulmonary Disease Phenotypes: Pulmonary He-3 Magnetic Resonance Imaging and Computed Tomography" COPD—Journal of Chronic Obstructive Pulmonary Disease, 13(5):601-609 (2016).
Porra et al. "Synchrotron Imaging Shows Effect of Ventilator Settings on Intra-breath Cyclic Changes in Pulmonary Blood Volume" American Journal of Respiratory Cell and Molecular Biology, 57(4):459-467 (2017).
Qing et al. "Assessment of Lung Function in Asthma and COPD using Hyperpolarized 129Xe Chemical Shift Saturation Recovery Spectroscopy and Dissolved-Phase MRI" NMR Biomedicine, 27(12):1490-1501 (2014).
Qing et al. "Regional Mapping of Gas Uptake by Blood and Tissue in the Human Lung using Hyperpolarized Xenon-129 MRI" Journal of Magnetic Resonance Imaging, 39(2):346-359 (2014).
Raghu et al. "An Official ATS/ERS/JRS/ALAT Statement: Idiopathic Pulmonary Fibrosis: Evidence-based Guidelines for Diagnosis and Management" American Journal of Respiratory and Critical Care Medicine, 183(6):788-824 (2011).
Rahaghi et al. "Cardiopulmonary coupling in chronic obstructive pulmonary disease: the role of imaging" Journal of Thoracic Imaging, 29(2):80-91 (2014).
Robertson et al. "Uncovering a Third Dissolved-phase 129Xe Resonance in the Human Lung: Quantifying Spectroscopic Features in Healthy Subjects and Patients with Idiopathic Pulmonary Fibrosis" Magnetic Resonance in Medicine, 78(4):1306-1315 (2017).
Rosenkranz et al. "Left ventricular heart failure and pulmonary hypertension" European Heart Journal, 37(12):942-954 (2016).
Rossvoll et al. "Pulmonary Venous Flow Velocities Recorded by Transthoracic Doppler Ultrasound: Relation to Left Ventricular Diastolic Pressures" Journal of the American College of Cardiology, 21(7):1687-1696 (1993).
Roversi et al. "Chronic Obstructive Pulmonary Disease and Cardiac Diseases. An Urgent Need for Integrated Care" 194(11):1319-1336 (2016).
Rowland et al. "Spectral Improvement by Fourier Thresholding of in vivo Dynamic Spectroscopy Data" Magnetic Resonance in Medicine, 76(3):978-985 (2016).
Ruppert et al. "Detecting Pulmonary Capillary Blood Pulsations Using Hyperpolarized Xenon-129 Chemical Shift Saturation Recovery (CSSR) MR Spectroscopy" Magnetic Resonance in Medicine, 75(4):1771-1780 (2016).
Simonneau et al. "Updated Clinical Classification of Pulmonary Hypertension" Journal of the American College of Cardiology, 54(1):S43-S54 (2009).
Stewart et al. "Experimental Validation of the Hyperpolarized 129Xe Chemical Shift Saturation Recovery Technique in Healthy Volunteers and Subjects with Interstitial Lung Disease" Magnetic Resonance in Medicine, 74(1):196-207 (2015).
Storto et al. "Hydrostatic Pulmonary Edema: High-Resolution CT Findings" American Journal of Roentgenology, 165(4):817-820 (1995).
Tsunoda et al. "Lung volume, thickness of alveolar walls, and microscopic anisotropy of expansion" Respiration Physiology, 22(3):285-296 (1974).
Virgincar et al. "Quantitative analysis of hyperpolarized 129Xe ventilation imaging in healthy volunteers and subjects with chronic obstructive pulmonary disease" NMR in Biomedicine, 26(4):424-435 (2013).
Wang et al. "Quantitative analysis of hyperpolarized 129 Xe gas transfer MRI" Medical Physics, 44(6):2415-2428 (2017).
Wang et al. "Hyperpolarized (129) Xe gas transfer MRI: the transition from 1.5T to 3T" Magnetic Resonance in Medicine, 80(6):2374-2383 (2018).
Wang et al. "Using Hyperpolarized (129)Xe MRI to Quantify Regional Gas Transfer in Idiopathic Pulmonary Fibrosis" Thorax, 73(1):21-28 (2018).
Weatherley et al. "Hyperpolarised xenon magnetic resonance spectroscopy for the longitudinal assessment of changes in gas diffusion in IPF" Thorax, 74:500-502 (2018).
Wolber et al. "Hyperpolarized Xe-129 NMR as a Probe for Blood Oxygenation" Magnetic Resonance in Medicine, 43(4):491-496 (2000).
Bier, Elianna A. "Characterizing the Temporal Dynamics of 129Xe Spectroscopy to Uncover the Origins of Gas Exchange Impairment" Thesis, Medical Physics Graduate Program, Duke University (91 pages) (2017).

* cited by examiner

© 2018 Duke University

© 2018 Duke University

© 2018 Duke University

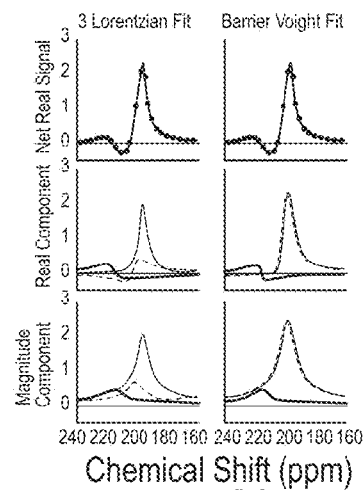
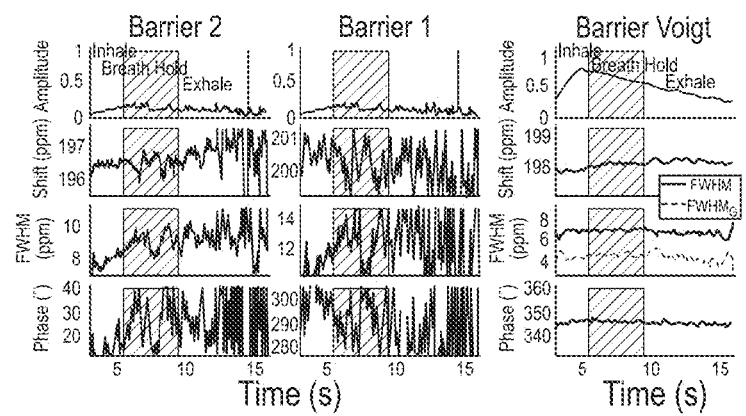
FIG. 6A
FIG. 6B
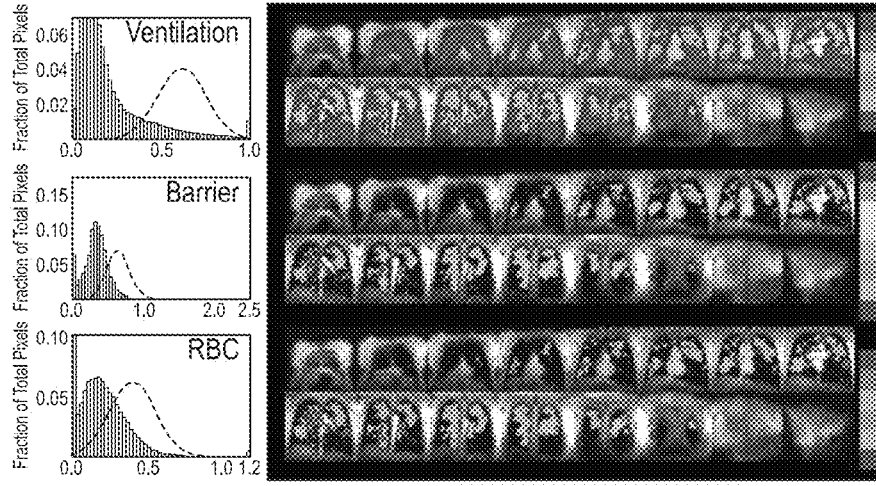
FIG. 7A
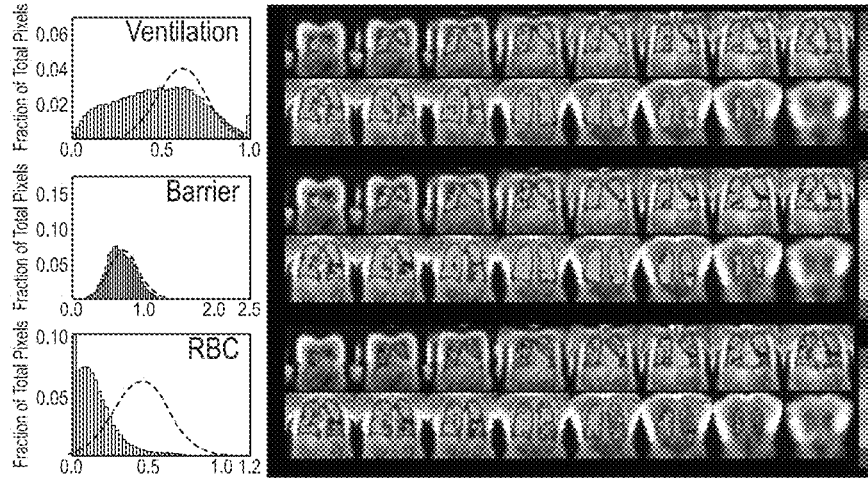
FIG. 7B

|  | Subject ID | SEX | AGE | PFTs (%Predicted) FVC (L) | DLCO (mL/min/mm Hg) | Intensity RBC:Barrier | RBC Oscillations Amplitude (%) | Chemical Shift (ppm) | FWHM (ppm) | Phase (°) |
|---|---|---|---|---|---|---|---|---|---|---|
| Healthy | 1 | M | 23 | 5.8 (96%) | 33.9 (88%) | 0.532 | 14.3 | 0.07 | 0.04 | 1.0 |
|  | 2 | M | 21 | 6.16 (100%) | 39.2 (114%) | 0.685 | 8.2 | 0.07 | 0.34 | 2.4 |
|  | 3 | M | 26 | 5.0 (98%) | 28.8 (89%) | 0.558 | 13.8 | 0.18 | 0.31 | 1.7 |
|  | 4 | M | 27 | 3.2 (65%) | 26.5 (92%) | 0.643 | 9.1 | 0.05 | 0.14 | 1.5 |
|  | 5 | M | 37 | 3.3 (67%) | 16.8 (55%) | 0.395 | 9.4 | 0.02 | 0.24 | 2.5 |
|  | 6 | M | 23 | ND | ND | 0.789 | 6.8 | 0.15 | 0.13 | 0.9 |
|  | 7 | M | 24 | 6.3 (112%) | 34.0 (93%) | 0.530 | 6.3 | 0.08 | 0.16 | 0.4 |
|  | 8 | F | 29 | ND | ND | 0.546 | 10.1 | 0.06 | 0.17 | 0.7 |
|  | Mean |  | 26.3 | 5.0 (89.7%) | 29.9 (88.5%) | 0.585 | 9.7 | 0.08 | 0.19 | 1.4 |
|  | SD |  | 5.0 | 1.4 (19.2%) | 7.8 (19.0%) | 0.119 | 2.9 | 0.05 | 0.10 | 0.8 |
| IPF | 11 | M | 56 | 2.1 (94%) | 7.0 (26%) | 0.100 | 24.9 | 1.16 | 0.65 | 19.8 |
|  | 12 | F | 61 | 2.5 (85%) | 11.6 (63%) | 0.132 | 14.9 | 0.74 | 0.35 | 13.4 |
|  | 13 | M | 68 | 1.9 (49%) | 11.6 (48%) | 0.211 | 19.9 | 0.29 | 0.36 | 5.8 |
|  | 14 | M | 70 | 4.3 (99%) | 17.0 (72%) | 0.143 | 13.9 | 0.48 | 0.16 | 8.5 |
|  | 15 | M | 62 | 2.7 (53%) | 16.1 (60%) | 0.230 | 16.1 | 0.26 | 0.28 | 4.7 |
|  | 16 | F | 67 | 1.6 (74%) | 8.4 (51%) | 0.114 | 17.2 | 0.37 | 0.30 | 6.7 |
|  | 17 | M | 67 | 3.0 (71%) | 14.6 (58%) | 0.283 | 6.3 | 0.18 | 0.14 | 1.2 |
|  | 18 | M | 69 | 3.6 (76%) | 13.6 (53%) | 0.284 | 20.5 | 0.22 | 0.25 | 4.4 |
|  | 19 | M | 75 | 2.3 (54%) | 11.4 (48%) | 0.164 | 18.0 | 0.17 | 0.24 | 4.8 |
|  | Mean |  | 66.1 | 2.7 (72.8%) | 12.4 (53.2%) | 0.185 | 16.8 | 0.43 | 0.30 | 7.7 |
|  | SD |  | 5.6 | 0.9 (18.1%) | 3.3 (12.8%) | 0.070 | 5.2 | 0.33 | 0.15 | 5.6 |

FIG. 14

| Characteristic | Healthy Volunteers N = 23 | COPD N = 8 | IPF N = 12 | Left Heart Failure N = 6 | PAH[a] N = 10 |
|---|---|---|---|---|---|
| Age (years) | 26 (22, 32) | 61.5 (57.0, 71.8) | 68 (63.3, 71.5) | 63.5 (58.0, 69.0) | 50 (46.5, 54.0) |
| Female | 5 (22%) | 3 (38%) | 2 (17%) | 2 (33%) | 5 (50%) |
| Nonwhite race | 7 (30%) | 0 (0%) | 0 (0%) | 1 (17%) | 2 (20%) |
| Body Mass Index | 24.0 (23.3, 27.4) | 24.3 (22.5, 26.5) | 28.8 (24.7, 33.0) | 29.4 (25.1, 32.3) | 29.6 (24.9, 33.9) |
| Current or prior tobacco use | 0 (0%) | 6 (75%) | 8 (67%) | 4 (67%) | 3 (30%) |
| Supplemental $O_2$ at rest | 0 (0%) | 5 (63%) | 4 (33%) | 1 (17%) | 2 (20%) |
| 6MWD[b] (m) | | 395 (324, 429), N=4 | 461 (369, 515), N=10 | | 500 (426, 575) |
| PFT (% predicted) | | | | | |
| $FEV_1$ | 92 (78, 102), N=19 | 34 (27, 55) | 70 (57, 80) | 72 (58, 85), N=4 | 83 (63, 94), N=9 |
| FVC | 96 (83, 103), N=19 | 79 (63, 91) | 63 (50, 76) | 75 (57, 95), N=4 | 96 (68, 99), N=9 |
| $FEV_1$/FVC | 81 (78, 88), N=19 | 49 (40, 54), N=7 | 84 (80, 89) | 84 (81, 89), N=3 | 82 (74, 87), N=4 |
| TLC | 102 (92, 113), N=18 | 100 (93, 107), N=2 | 48 (43, 63), N=3 | 94 (88, 100), N=2 | 95 (86, 107), N=9 |
| $DL_{CO}$ | 91 (83, 97), N=19 | 43 (39, 55) | 50 (40, 60) | 82 (59, 96), N=4 | 81 (68, 83), N=9 |
| Echocardiogram[b] | | | | | |
| % with RV dilation[c] | | 0 (0%), N=3 | | 1 (20%), N=5 | 2 (20%) |
| % with RV dysfunction[c] | | 0 (0%), N=3 | | 0 (0%) | 2 (20%) |
| RVSP (mm Hg) | | | | 47 (39, 51), N=3 | 54 (45, 58), N=7 |
| % with LVEF < 55% | | 0 (0%), N=3 | | 2 (33%) | 0 (0%) |
| Right Heart Catheterization[b] | | | | | |
| Right atrial pressure | | 10, N=1 | | 15 (13, 15), N=3 | 7 (6, 12), N=9 |
| Mean PA pressure | | 24, N=1 | | 32 (29, 36), N=3 | 46 (39, 39) |
| PCWP | | 20, N=1 | | 19 (17, 29), N=3 | 12 (10, 14) |
| PVR | | 0.6, N=1 | | 2.1 (2.0, 2.2), N=3 | 6 (4, 8) |
| Cardiac Index | | 2.9, N=1 | | 2.4 (2.2, 2.6), N=2 | 2.9 (2.4, 3.5) |

FIG. 15

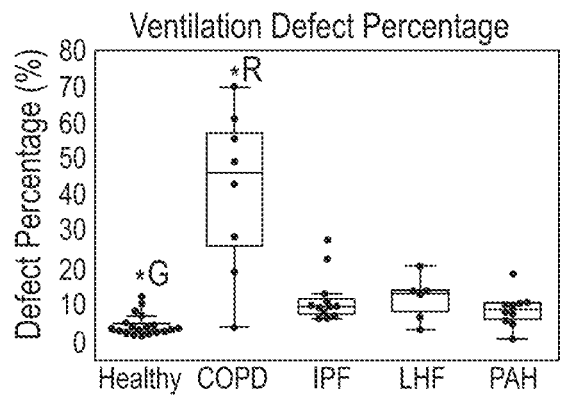
FIG.17A
G (green)
R (red)
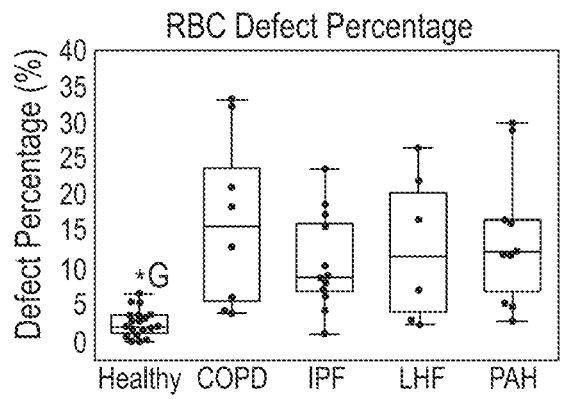
FIG.17C
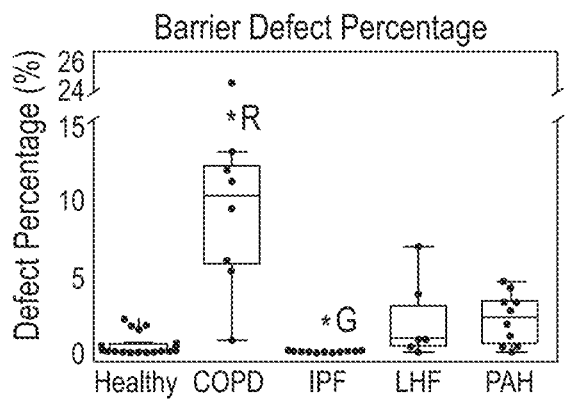
FIG.17B
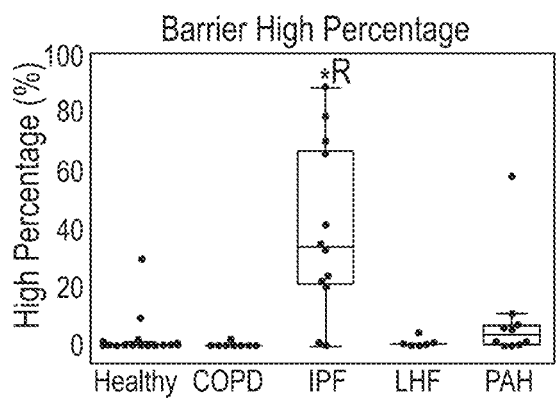
FIG.17D
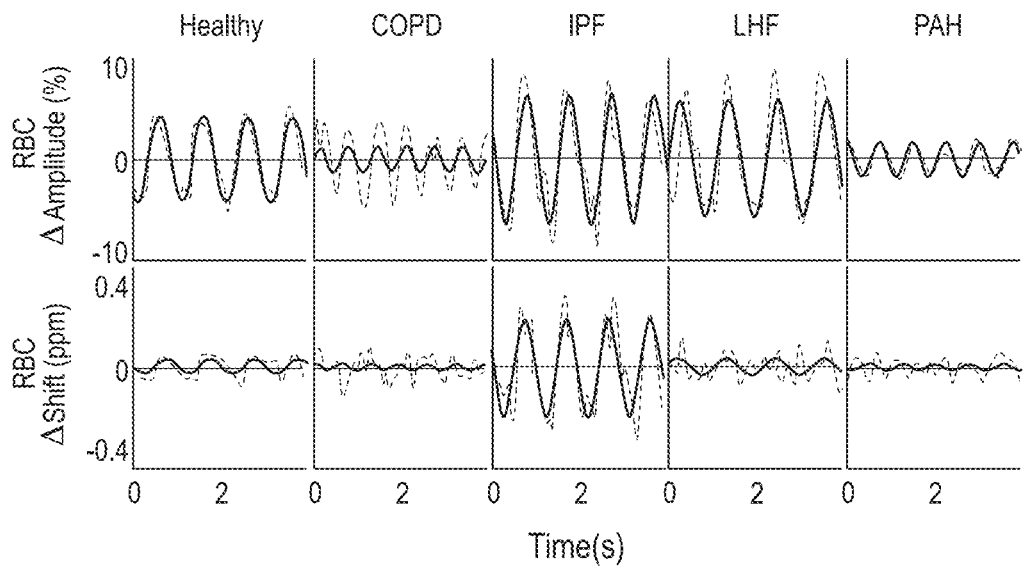
FIG.18A
FIG.18B

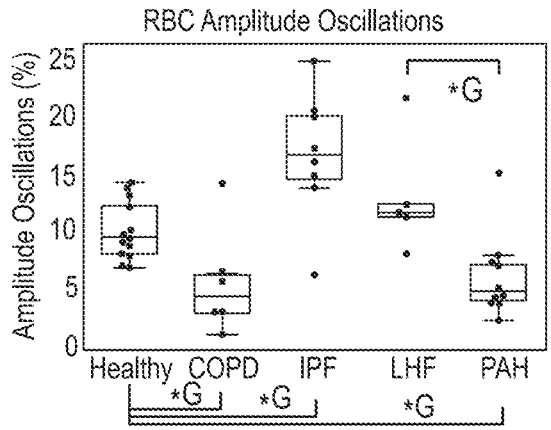
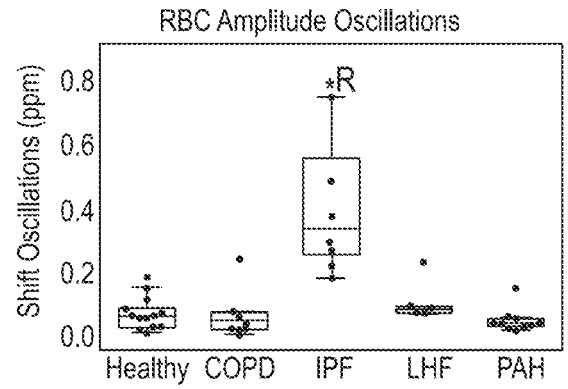
FIG.19A
FIG.19B
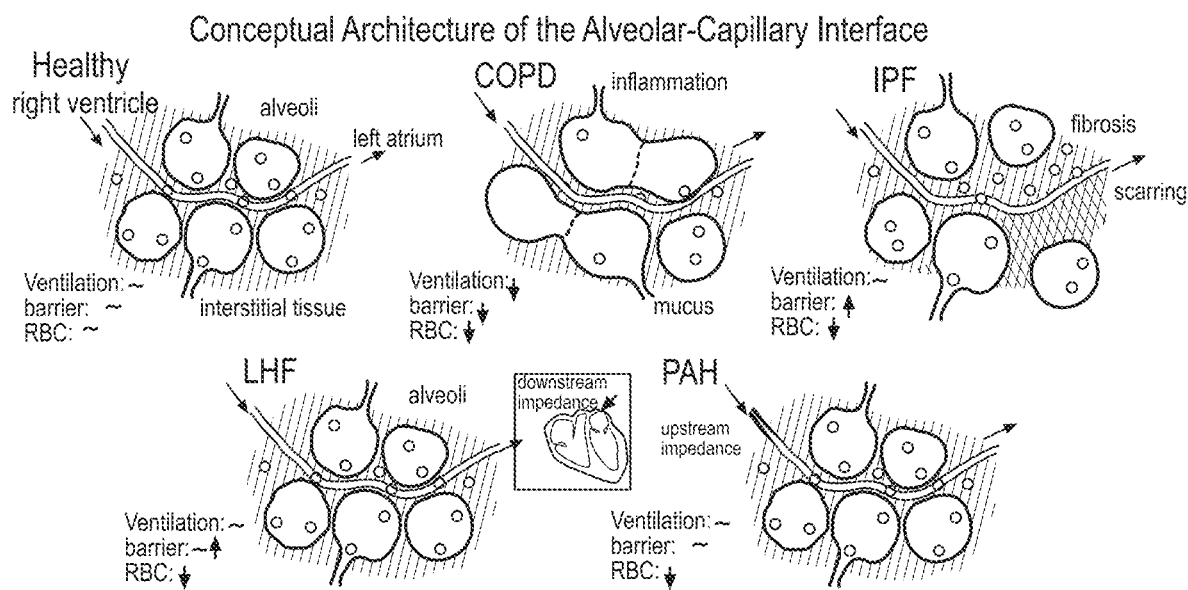
FIG.20

Representative Images/Spectra of Healthy, PAH and ILD

DYNAMIC 129XE GAS EXCHANGE SPECTROSCOPY

RELATED APPLICATIONS

This application claims the benefit of and priority to U.S. Provisional Application Ser. No. 62/673,175 filed May 18, 2018, the contents of which are hereby incorporated by reference as if recited in full herein.

GOVERNMENT GRANTS

The invention was made with government support under Grant Numbers NHLB1 R01 HL105643 and NHLBI R01HL126771 awarded by the National Institutes of Health and under Grant Number HHSN268201700001C awarded by the Department of Health and Human Services. The United States government has certain rights in the invention.

RESERVATION OF COPYRIGHT

A portion of the disclosure of this patent document contains material to which a claim of copyright protection is made. The copyright owner has no objection to the facsimile or reproduction by anyone of the patent document or the patent disclosure, as it appears in the Patent and Trademark Office patent file or records, but reserves all other rights whatsoever.

FIELD OF THE INVENTION

The invention relates to medical evaluations using in vivo NMR spectroscopy.

BACKGROUND

Hyperpolarized (HP) $^{129}$Xe MRI is emerging as a valuable means of imaging lung structure and function. See Kruger et al. Functional imaging of the lungs with gas agents. *Journal of Magnetic Resonance Imaging.* 2016; 43(2):295-315; Matin et al. Chronic obstructive pulmonary disease: lobar analysis with hyperpolarized $^{129}$Xe MR imaging. *Radiology.* 2016; 282(3):857-868. Arguably, its most significant feature as a probe for lung function is related to its solubility in blood and biological tissues, combined with distinct in vivo chemical shifts that reflect the local environment. See Cherubini et al. Hyperpolarised xenon in biology. *Progress in Nuclear Magnetic Resonance Spectroscopy.* 2003; 42(1):1-30. $^{129}$Xe dissolved in human blood exhibits separate resonances for red blood cells (RBCs) and plasma, separated by approximately 22 ppm. See Norquay et al. $^{129}$Xe chemical shift in human blood and pulmonary blood oxygenation measurement in humans using hyperpolarized 129Xe NMR. *Magnetic resonance in medicine.* 2017; 77(4):1399-1408; Wolber et al. Hyperpolarized $^{129}$Xe NMR as a probe for blood oxygenation. *Magnetic resonance in medicine.* 2000; 43(4):491-496. $^{129}$Xe spectra acquired in the human lung also exhibit a unique RBC peak at 217 ppm, relative to the gas-phase resonance at 0 ppm, as well as a resonance consisting of $^{129}$Xe dissolved in both plasma and parenchymal tissues. See Kaushik et al. Measuring diffusion limitation with a perfusion-limited gas-hyperpolarized 129Xe gas-transfer spectroscopy in patients with idiopathic pulmonary fibrosis. *Journal of Applied Physiology.* 2014; 117(6):577-585. Because these environments also form the barrier to diffusive $^{129}$Xe or $O_2$ transfer to RBCs, it is often termed the barrier resonance. See Cleveland et al. 3D MRI of impaired hyperpolarized $^{129}$Xe uptake in a rat model of pulmonary fibrosis. *NMR in Biomedicine.* 2014; 27(12):1502-1514. Although recent high resolution spectroscopy suggests that the barrier resonance may contain additional structure, it is generally considered to have a frequency shift of about 198 ppm. See Robertson et al. Uncovering a third dissolved-phase $^{129}$Xe resonance in the human lung: Quantifying spectroscopic features in healthy subjects and patients with idiopathic pulmonary fibrosis. *Magnetic resonance in medicine.* 2017; 78(4):1306-1315. The contents of the cited documents are hereby incorporated by reference as if recited in full herein.

Recently, these unique spectroscopic properties of $^{129}$Xe have been exploited to yield 3D images of pulmonary gas exchange. See Qing et al. Regional mapping of gas uptake by blood and tissue in the human lung using hyperpolarized xenon-129 MRI. *Journal of Magnetic Resonance Imaging.* 2014; 39(2):346-359. Such imaging has revealed impaired gas exchange in various diseases affecting the cardiopulmonary system. In patients with idiopathic pulmonary fibrosis (IPF), for example, $^{129}$Xe uptake in the barrier is significantly enhanced throughout much of the lung, while its transfer to RBCs is focally impaired. See Wang et al., Using hyperpolarized $^{129}$Xe MRI to quantify regional gas transfer in idiopathic pulmonary fibrosis. *Thorax.* 2017:thoraxjnl-2017-210070. By contrast, in the setting of COPD with emphysema, both barrier uptake and RBC transfer are diminished. See Wang et al., Quantitative Analysis of Hyperpolarized $^{129}$Xe Gas Transfer MRI. Medical Physics. 2017. Moreover, $^{129}$Xe gas exchange MRI has recently demonstrated impaired RBC transfer in pulmonary vascular disease. See Dahhan et al., Abnormalities in hyperpolarized 129Xe magnetic resonance imaging and spectroscopy in two patients with pulmonary vascular disease. *Pulmonary circulation.* 2016; 6(1):126-131. The contents of the documents cited in the Background are hereby incorporated by reference as if recited in full herein.

Patients can present with wide range of co-morbidities such as asthma-COPD overlap syndrome (ACOS), combined fibrosis and emphysema (CPFE), or secondary pulmonary hypertension (PH), and it can be important to differentiate the underlying pathophysiologies responsible for impaired gas exchange.

Pulmonary vascular diseases (PVD), such as pulmonary arterial hypertension (PAH) and pulmonary venoocclusive disease (PVOD) cause an obstruction of blood flow through the lung vasculature that results in right heart failure. Even with current therapies, PVD is associated with substantial morbidity and mortality, with 5-year survival only~50%. However, the management of PVD is significantly limited by the criteria for its diagnosis as well as non-invasive methods of monitoring disease. The most common PVD, PAH can be diagnosed only by invasive right heart catheterization (RHC). Moreover, it requires meeting specific hemodynamic and clinical criteria: pulmonary hypertension (PH), defined as a mean pulmonary artery pressure (mPAP) ≥25 mmHg, with a pulmonary capillary wedge pressure (PCWP)≤15 mmHg in the absence of significant heart, lung or specific systemic diseases. Other PVD is either diagnosed by pathology or exclusion. These strict criteria may exclude patients who actually have the pathologic lesions of PVD that could potentially benefit from treatment with pulmonary vasodilators. For example, patients with diastolic heart failure or lung disease can develop significant precapillary PH associated with a high pulmonary vascular resistance (PVR). Unfortunately, such secondary causes of increased resistance typically prevent invasive catheterization from definitively diagnosing PVD. Yet this scenario of suspected PVD in patients with concomitant disease is increasingly common in the aging population.

Thus, there is a need for non-invasive technologies that can aid in diagnosing and/or monitoring pulmonary hypertension and interstitial lung disease including PVD, particularly for many patients who may benefit from PAH-specific therapies but otherwise will likely remain untreated.

SUMMARY OF EMBODIMENTS OF THE INVENTION

Embodiments of the present invention provide non-invasive systems and methods to generate multiple dynamic spectroscopic parameters of the gas exchange region of the lung associated with three different $^{129}$Xe resonances, a $^{129}$Xe gas resonance, a $^{129}$Xe barrier resonance and $^{129}$Xe red blood cells ("RBCs" or "RBC") resonance.

Embodiments of the invention can provide non-invasive methods and systems to aid in diagnosing and/or monitoring pulmonary hypertension and interstitial lung disease including PAH.

Embodiments of the invention can use markers associated with dynamic spectroscopy of $^{129}$Xe to distinguish between pre-capillary (i.e., pulmonary arterial hypertension) and post-capillary vasculature disease.

Embodiments of the invention provide disease-specific signature patterns comprising peak-to-peak height values and/or shapes of oscillations of one or more of RBC amplitude, chemical shift and phase.

The oscillations can be associated with one or more of an inhale, breath-hold and/or exhale time period.

Embodiments of the invention provide a library of disease signature patterns that can be useful to diagnose lung diseases or injury, study or evaluate interstitial lung diseases or injury and/or the progression or abatement thereof, and/or evaluate the efficacy of directed therapies the side effects or the inadvertent negative effects of therapies or drug treatments and/or drug discovery.

Embodiments of the invention can use $^{129}$Xe MRI gas-exchange ventilation, barrier and RBC images along with dynamic spectroscopy to distinguish between pre-capillary and post capillary vasculature conditions or disease and/or may, for example, determine how much of a capillary bed is compromised or injured.

Embodiments of the invention can correct and/or adjust RBC oscillation amplitudes by stroke volume and pulmonary exchange volume.

Embodiments of the invention are directed to methods of generating dynamic spectroscopy parameters. The methods include: obtaining a $^{129}$Xe spectrum of free induction decays (FIDs) $^{129}$Xe NMR signal of a gas exchange region of a lung or lungs of a subject during a breathing maneuver comprising one or more of inspiration/inhale, breath-hold and expiration/exhale; fitting the obtained $^{129}$Xe spectrum of the FIDs with a curve fitting function; and electronically generating a plurality of dynamic $^{129}$Xe spectral parameters based on the fitting. The $^{129}$Xe spectrum is modeled with one or more non-Lorentzian line shapes and the plurality of dynamic $^{129}$Xe spectral parameters include plots over time of at least one of: (i) barrier amplitude, barrier chemical shift (ppm), one or more barrier full width at half maximum (FWHM)(ppm) parameters; (ii) gas amplitude, gas chemical shift (ppm), gas FWHM (ppm), and gas phase (degrees); and (iii) red blood cell (RBC) amplitude, RBC chemical shift (ppm), RBC FWHM (ppm), and RBC phase (degrees).

The method can include, before the fitting and generating steps, extracting temporal variations in $^{129}$Xe RBC resonance occurring at a cardiac frequency.

The fitting can be carried out with a $^{129}$Xe barrier resonance modeled as a Voigt line shape and with $^{129}$Xe RBC and $^{129}$Xe gas-phase resonances each modeled using a Lorentzian line shape. The barrier resonance can be characterized by both a Lorentzian FWHM parameter and a Gaussian FWHM (FWHM$_G$) (ppm) parameter.

The method can further include adjusting amplitude "ApRc" of the RBC amplitude plot by multiplying by: (V_stroke_ref/V_stroke)*(PEV/PEV_ref). V_stroke_ref is a reference stroke volume like 94 ml or 95 ml (adult), V_stroke is a subject's actual stroke volume, PEV_ref is a reference pulmonary exchange volume, and PEV is the subject's measured pulmonary exchange volume.

The method can further include correcting amplitude of the RBC amplitude plot of the $^{129}$Xe spectral parameter for magnetization decays caused by T1 and RF-induced depolarization during a breath-hold period of the breath-hold of the breathing maneuver by dividing the RBC amplitude "A" by a calculated apparent T1 decay constant (T1app). T1app can be quantified by fitting RBC amplitude over time "t" to $Ae^{-t/T1_{app}}$.

The method can further include detrending amplitudes of the $^{129}$Xe spectral parameters, then calculating peak-peak variation over time.

The method can further include calculating temporal changes in signal amplitude of the RBC amplitude (A) as a percentage change from baseline: (rbc_amp_percent): rbc_amp_percent=(rbc_amp−A*exp(−t/T1$_{app}$))/(A*exp(−t/T1$_{app}$)). T1$_{app}$ is a T1 decay constant and t is time (seconds).

The method can further include calculating temporal changes in signal amplitude of the RBC amplitude (A) using peak to peak analysis of a difference between a maximum and a minimum in an oscillating signal of the RBC amplitude.

The method can further include high-pass filtering each of the RBC amplitude, RBC chemical shift, RBC phase and RBC FWHM with a 0.5 Hz cutoff frequency to thereby remove residual baseline variation and provide filtered parameter plots of the RBC spectral parameters.

The method can further include fitting the filtered parameter plots to a sinusoid with phase offset:

$$\tfrac{1}{2}A_{pk\text{-}pk}\sin(2\pi f_c t+\varphi),$$

where $A_{pk\text{-}pk}$ is the peak-to-peak amplitude, $f_c$ is the cardiac frequency, t is time in seconds, and $\varphi$ is a phase off-set, and where $f_f$ is cardiac frequency that is derived from the subject's RBC amplitude oscillations.

$f_c$ can be used in temporal fits of all other RBC spectral parameters (chemical shift, linewidth, and phase).

The method can further include normalizing the RBC amplitude spectral parameter, the barrier amplitude spectral parameter and the gas amplitude spectral parameter to a barrier-phase or gas-phase $^{129}$Xe signal.

The method can further include, before the fitting and generating steps, pre-processing raw FIDs by Fourier Transforming raw data along an indirect time domain with respect to a breath hold time period of the breath hold of the breathing maneuver, retaining only coefficients that exceed a defined threshold, then Fourier transforming back along an indirect frequency domain to provide an FID with increased SNR relative to raw FIDs for the fitting to thereby filter non-dominant frequencies out of the indirect time domain to smooth temporal changes between different FIDs, while leaving spectral-frequency domain intact.

The method can further include using a FID sliding boxcar window filter and averaging a plurality of the time domain filtered FIDs to provide an FID with increased SNR for the fitting.

The obtaining can be at least partially in response to a pulse sequence with a TR in a range of 20 ms-300 ms, and a flip angle of about 20-90 degrees to thereby provide increased sensitivity to cardiogenic oscillations.

The obtaining can be at least partially in response to a pulse sequence with a TR in a range of 200-300 ms and a flip angle in a range of 20-90 degrees.

The method can further include providing a plurality of defined different disease pattern signatures of the $^{129}$Xe spectral parameters correlated to different pulmonary hypertension and interstitial lung diseases.

The method can further include electronically evaluating the generated $^{129}$Xe spectral parameters to identify whether the subject has one or more of the defined different disease pattern signatures.

The one or more of the defined different disease patterns can include oscillations of one or more of the RBC spectral parameters that exceeds a defined peak to peak threshold.

The one or more of the defined different disease patterns can include oscillations of one or more of the RBC spectral parameters that is below a defined peak to peak threshold.

The one or more of the defined different disease patterns can be based on a shape of the oscillations of one or more of the $^{129}$Xe spectral parameters.

The at least one interstitial lung disease can have a disease pattern signature with an RBC frequency shift that decreases during the breath-hold of the breathing maneuver relative to the inhale and/or exhale portion of the breathing maneuver.

The defined different disease patterns can distinguish pre-capillary vascular obstruction by diminished RBC amplitude oscillations relative to a defined norm.

The defined different disease patterns can distinguish post-capillary vascular disease from pre-capillary vascular disease by increased RBC amplitude oscillations relative to a defined norm.

One or more of the defined different disease patterns can identify combined pre- and post-capillary vascular disease, optionally by a shape of the RBC amplitude oscillations.

The method can further include comparing RBC amplitude oscillations of one or more RBC plot pre and post-administration of a pharmaceutical agent and identifying vascular reactivity and/or change based on changes in RBC amplitude oscillations.

The pharmaceutical agent can be a vasodilator, optionally the vasodilator is an inhaled vasodilator.

The pharmaceutical agent can include prostacyclin.

The method can further include comparing gas exchange $^{129}$Xe MRI images of the subject to detect pulmonary hypertension associated with diminished RBC transfer that affects a disproportionately larger fraction of the lung than can be explained by a fraction having abnormal barrier uptake.

The obtained data can be acquired between every 20 ms to every 300 ms during the breathing maneuver. The breathing maneuver can include breath-hold, full inspiration and full expiration over a time period of 10-30 seconds.

The fitting can be carried out with each resonance characterized by 4 spectral parameters: amplitude ($\alpha$), frequency (f), phase ($\varphi$), and Lorentzian linewidth (FWHM), and, for the barrier resonance, a 5$^{th}$ parameter, a Gaussian linewidth (FWHM$_G$), is also extracted, wherein the fitting is carried out with the barrier resonance initialized with equal Lorentzian and Gaussian linewidths, and wherein the fitting is carried out using the below equation:

$$s_{fit} = a_{rbc}e^{i\varphi_{rbc}+2\pi if_{rbc}t}e^{-\pi t\times FWHM_{rbc}} +$$
$$a_{bar}e^{i\varphi_{bar}+2\pi if_{bar}t}e^{-\pi t\times FWHM_{bar}}e^{-4ln2\times t^2 FWHM_{bar}^2 G_{bar}^2} +$$
$$a_{gas}e^{i\varphi_{gas}+2\pi if_{gas}t}e^{-\pi t\times FWHM_{gas}} \quad \text{EQN(1)}$$

The method can further include identifying whether the subject has IPF, wherein IPF can be characterized by a disease signature pattern with RBC amplitude oscillations that are significantly larger (at least about 1.25× or 1.5× larger) than a healthy cohort, and the RBC frequency (chemical shift/ppm) and phase oscillations are at least 1.5×, typically at least 2× above a healthy cohort.

The RBC amplitude variations can be at least 1.5 fold greater than a healthy cohort (optionally 16.8±5.2% vs 9.7±2.9%; P=0.008), the chemical shift oscillations are more than 5-fold higher than the healthy cohort (optionally 0.43±0.33 ppm vs 0.083±0.05 ppm; P<0.001), and the RBC phase oscillations are more than 5-fold higher than the healthy cohort (optionally 7.7±5.6° vs 1.4±0.8°; P<0.001).

The method can further include transmitting the obtained data from an imaging site with an MR Scanner to a remote server. The remote server can perform the fitting and generating actions. The remote server can include or be in communication with a database of defined different disease pattern signatures of the $^{129}$Xe spectral parameters correlated to pulmonary hypertension and interstitial lung diseases.

The method can further include obtaining a plurality of $^{129}$Xe imaging parameters of the lung or lungs of the subject including at least two of RBC defect percentage, ventilation defect percentage and barrier defect percentage; and identifying whether the patient has a cardiopulmonary disease based on the obtained $^{129}$Xe imaging parameters and at least two of the plurality of the dynamic $^{129}$Xe spectral parameters.

IPF can be characterized by a disease signature pattern comprising an RBC chemical shift (ppm) that is below 217 ppm.

A method of identifying a cardiopulmonary disease of a patient, comprising: obtaining a plurality of $^{129}$Xe imaging parameters including red blood cell (RBC) defect percentage, ventilation defect percentage and barrier defect percentage; obtaining a plurality of $^{129}$Xe dynamic spectroscopy parameters including RBC shift oscillation and RBC amplitude oscillation; and identifying whether the patient has a cardiopulmonary disease based on the obtained $^{129}$Xe imaging parameters and the $^{129}$Xe dynamic spectroscopy parameters.

The method can further include generating a graphic signature of patient cardiopulmonary health or disease state based on the obtained $^{129}$Xe imaging parameters and the $^{129}$Xe dynamic spectroscopy parameters, then identifying whether the patient has a cardiopulmonary disease based on the generated graphic signature.

The method can further include comparing the generated graphic signature to a library of graphic signatures which comprises unique graphic signatures for each of: chronic obstructive pulmonary disease (COPD), idiopathic pulmonary fibrosis (IPF), left heart failure (LHF), and pulmonary arterial hypertension (PAH).

The method can further include providing a diagnostic model that defines a likelihood of different diseases based on different thresholds of peaks of RBC oscillation and peaks of chemical shift (ppm) oscillation. The identifying can be carried out using the provided diagnostic model.

Yet other embodiments are directed to an MRI scanner system that includes an MRI scanner comprising a MRI receiver and at least one processor in communication with the MRI scanner and configured to carry out any of the methods of the present invention.

Other embodiments are directed to a medical evaluation system that includes a server in communication with at least one MRI scanner and having at least one processor that carries out any of the methods of the present invention.

Although described herein with respect to method aspects of the present invention, it will be understood that the present invention may also be embodied as systems and computer program products.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

The patent or application file contains at least one drawing executed in color. Copies of this patent or patent application publication with color drawings will be provided by the Office upon request and payment of the necessary fee.

Features of the present invention will be more readily understood from the following detailed description of exemplary embodiments thereof when read in conjunction with the accompanying drawings.

FIG. 4A compares peak-to-peak RBC amplitude oscillations (percent). FIG. 4B compares peak-to-peak RBC FWHM oscillations (ppm). FIG. 4C compares peak-to-peak RBC chemical shift oscillations (ppm). FIG. 4D compares peak-to-peak RBC phase (degrees) oscillations.

FIG. 5A compares peak-to-peak RBC amplitude oscillations (percent).

FIG. 5B compares peak-to-peak RBC FWHM oscillations (ppm). FIG. 5C compares peak-to-peak RBC chemical shift oscillations (ppm). FIG. 5D compares peak-to-peak RBC phase (degrees) oscillations.

FIG. 6A are graphs of dissolved phase fits for a large average of FIDs with minimal residual error for the 3-Lorentzian model (left side) and barrier Voigt model (left side) according to embodiments of the present invention.

FIG. 6B are graphs that illustrate dynamically acquired spectroscopy for a healthy volunteer which returns poor condition fits for the barrier resonances in the 3-Lorentizian model (left and middle set of panels), which is overcome by the barrier Voight model (right most panels) according to embodiments of the present invention.

FIG. 7A is set of color-coded $^{129}$Xe MRI images for a COPD patient with severe ventilation defects (ventilation images top two rows) but with barrier uptake (middle two rows) and RBC uptake (bottom two rows) relatively well-matched according to embodiments of the present invention.

FIG. 7B is set of color-coded $^{129}$Xe MRI images for a COPD patient (ventilation images top two rows) with barrier uptake (middle two rows) and RBC uptake (bottom two rows) showing RBC transfer defects disproportionately worse than barrier uptake suggesting possible pre-capillary pulmonary hypertension according to embodiments of the present invention.

FIG. 12A (left panels) illustrates RBC chemical shift (ppm), FWHM (ppm), $FWHM_G$ (ppm), and phase (degrees). FIG. 12B illustrates barrier chemical shift (ppm), FWHM (ppm), $FWHM_G$ (ppm), and phase (degrees). FIG. 12C illustrates a derived metric of RBC:barrier ratio. FIG. 12D illustrates a derived metric of RBC-barrier frequency difference for chemical shift (ppm) (i.e., the difference in chemical shift between the RBC and barrier peak) according to embodiments of the present invention.

FIG. 14 is a table of subject demographics, pulmonary function test (PFT) results, and RBC oscillation information according to embodiments of the present invention.

FIG. 15 is a table of demographic and clinical characteristics stratified by condition according to embodiments of the present invention.

FIG. 17A is a graph of ventilation defect percentage for healthy and different disease cohorts according to embodiments of the present invention.

FIG. 17B is a graph of RBC defect percentage for healthy and different disease cohorts according to embodiments of the present invention.

FIG. 17C is a graph of Barrier defect percentage for healthy and different disease cohorts according to embodiments of the present invention.

FIG. 17D is a graph of Barrier high percentage for healthy and different disease cohorts according to embodiments of the present invention.

FIG. 18A is a graph of RBC A amplitude (%) over time (s) for healthy and different disease cohorts according to embodiments of the present invention.

FIG. 18B is a graph of RBC A shift (ppm) over time (s) for healthy and different disease cohorts according to embodiments of the present invention.

FIG. 19A is a graph of RBC amplitude oscillations (%) versus healthy and different disease cohorts according to embodiments of the present invention.

FIG. 19B is a graph of RBC shift oscillations (ppm) versus healthy and different disease cohorts according to embodiments of the present invention.

FIG. 20 is an illustration of a conceptual model depicting disease phenotypes at an alveolar-capillary interface and biomarker parameters according to embodiments of the present invention.

DETAILED DESCRIPTION OF EMBODIMENTS OF THE INVENTION

Figure 1:
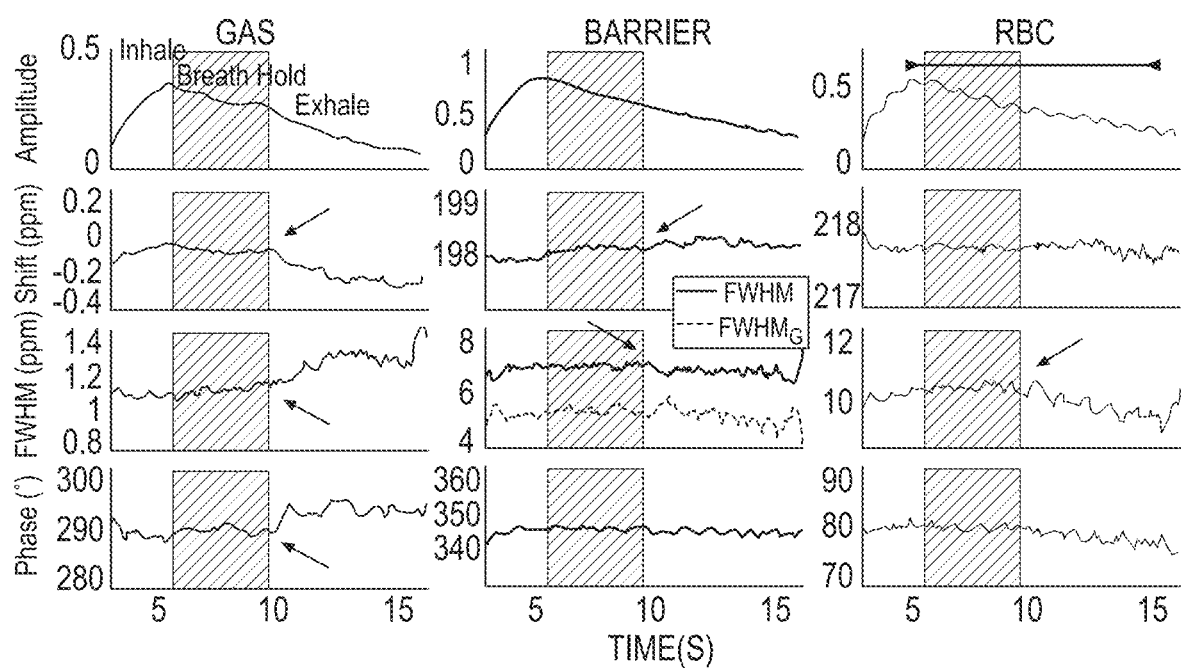
FIG. 1 are plots/graphs of temporal changes in spectroscopic parameters of the $^{129}$Xe gas (left side graphs), barrier (middle graphs) and RBC (right side graphs) resonances (normalized) in a representative healthy subject during inhalation, breath hold and exhalation according to embodiments of the present invention.

While the invention may be made in modified and alternative forms, specific embodiments thereof are shown by way of example in the drawings and will be described in detail. It should be understood, however, that there is no intent to limit the invention to the particular forms disclosed, but on the contrary, the invention is to cover all modifications, equivalents, and alternatives falling within the spirit and scope of the invention. Like reference numbers signify like elements throughout the description of the figures.

In the figures, the thickness of certain lines, layers, components, elements or features may be exaggerated for clarity. Broken lines illustrate optional features or operations unless specified otherwise. The sequence of operations (or steps) is not limited to the order presented in the claims or figures unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "MRI scanner" refers to a magnetic resonance imaging and/or NMR spectroscopy system. As is well known, the MRI scanners include a low field strength magnet (typically between about 0.1 T to about 0.5 T), a medium or a high-field strength super-conducting magnet, an RF pulse excitation system, and a gradient field system. MRI scanners are well known to those of skill in the art. Examples of commercially available clinical MRI scanners include, for example, those provided by General Electric Medical Systems, Siemens, Philips, Varian, Bruker, Marconi, Hitachi and Toshiba. The MRI systems can be any suitable magnetic field strength, such as, for example, about 1.5 T, and may be higher field systems of between about 2.0 T-10.0 T.

The term "high-field strength" refers to magnetic field strengths above 1.0 T, typically above 1.5 T, such as 2.0 T or 3.0 T. However, the present invention is not limited to these field strengths and may suitable for use with higher field strength magnets, such as, for example, 3.0 T or even greater.

The term "hyperpolarized" $^{129}$Xe refers to $^{129}$Xe that has increased polarization over natural or equilibrium levels. As is known by those of skill in the art, hyperpolarization can be induced by spin-exchange with an optically pumped alkali-metal vapor. See Albert et al., U.S. Pat. No. 5,545,396; and Cates et al, U.S. Pat. Nos. 5,642,625 and 5,809,801. These references are hereby incorporated by reference as if recited in full herein. One polarizer that is suitable for generating the hyperpolarized $^{129}$Xe is the 9800, 9810 or 9820 polarizer models made by Polarean, Imaging, plc, Durham, N.C. Thus, as used herein, the terms "hyperpolarize", "polarize", and the like mean to artificially enhance the polarization of certain noble gas nuclei over the natural or equilibrium levels.

The term "automatically" means that the operation can be substantially, and typically entirely, carried out without human or manual input, and is typically programmatically directed or carried out. The term "electronically" includes both wireless and wired connections between components. The term "programmatically" means under the direction of a computer program that communicates with electronic circuits and other hardware and/or software.

The term "3-D image" refers to visualization in 2-D what appear to be 3-D images using volume data that can represent features with different visual characteristics such as with differing intensity, opacity, color, texture and the like. For example, the 3-D image of the lung can be generated to illustrate differences in barrier thickness using color or opacity differences over the image volume. Thus, the term "3-D" in relation to images does not require actual 3-D viewability (such as with 3-D glasses), just a 3-D appearance in a 2-D viewing space such as a display. The 3-D images comprise multiple 2D slices. The 3-D images can be volume renderings well known to those of skill in the art and/or a series of 2-D slices, which can be visually paged through.

The term "detrend" and derivatives thereof means adjusting amplitude signal that decays over the course of a breath hold by correcting for the apparent T1 relaxation caused by the combination of true oxygen-induced relaxation and that caused by application of radio frequency pulses. This flattens the amplitude signal out relative to a non-detrended amplitude signal so that oscillations can be more readily identified and/or quantified.

The term "normalize" and derivatives thereof, with respect to oscillations of RBC spectra of the different spectral parameters, means normalizing RBC signal by dividing its amplitude by that of another spectral parameter (i.e., an amplitude of the barrier or gas-phase resonance) which can be carried out as normalizing for displaying the dynamics of RBC, barrier and gas, typically before detrending.

Actual RBC oscillation amplitudes can also be "normalized" for a particular patient/subject, by adjusting for the individual patient's stroke volume and/or available capillary exchange volume.

The terms "raw data", "raw FIDs" and "raw NMR signal" refer to the complex NMR signal acquired in the time-domain prior to Fourier transformation.

The term "about" with respect to flip angle means that the number can vary within +/−10%. The term "about" with respect to time means that the stated number can vary is +/−20%. The term "about" with respect to resonance frequency means 2-5 ppm (RBC chemical shift varies from about 214.5-219).

As is well known, a basic NMR spectrum line shape has amplitude, chemical shift (sometimes called frequency), linewidth (s), and phase (degrees). FID is a time domain signal (decaying oscillations). Frequency and chemical shift are one and the same. Chemical shift is a frequency referenced to some standard frequency and usually quoted in ppm rather than Hz. Similarly, FWHM/linewidth can be given in Hz or ppm. The conversion for FWHM/linewidth from Hz to ppm is carried out by dividing by the $^{129}$Xe Larmor frequency.

Embodiments of the invention may be particularly suitable for use with human patients but may also be used with animals or other mammalian subjects.

Generally stated, embodiments of the invention obtain and quantify spectral parameters of hyperpolarized $^{129}$Xe exchanging in gas exchange regions of the lung during a breathing maneuver (i.e., protocol) associated with one or all of inhale, breath-hold and exhale. The gas exchange region of the lung includes $^{129}$Xe gas exchange between airspaces, interstitial barrier, and red blood cells (RBCs) which are sensitive to pulmonary pathophysiology. Embodiments of the invention obtain and evaluate dynamics of $^{129}$Xe spectroscopy with a particular focus on quantifying cardiogenic oscillations in the RBC resonance.

As discussed in the Background, the spectral properties of $^{129}$Xe have been well-characterized in vitro and in vivo. The extraordinary sensitivity of $^{129}$Xe diffusive barrier uptake and RBC transfer to a wide range of pathologies is promising, even as it presents new challenges. Beyond characterizing the static parameters of $^{129}$Xe gas transfer spectra, their temporal dynamics provide an opportunity to gain what may be additional clinically significant insights. To this end, preliminary work has reported intriguing observations of cardiac pulsation in the amplitude of the RBC resonance. See Norquay et al. $^{129}$Xe chemical shift in human blood and pulmonary blood oxygenation measurement in humans using hyperpolarized $^{129}$Xe NMR. *Magnetic resonance in medicine*. 2017; 77(4):1399-1408; and Ruppert et al., Detecting pulmonary capillary blood pulsations using hyperpolarized xenon-129 chemical shift saturation recovery (CSSR) MR spectroscopy. *Magnetic resonance in medicine.* 2015. The contents of these documents are hereby incorporated by reference herein. However, this work was focused primarily on characterizing $^{129}$Xe uptake in the alveolar septal unit on the 0-100 ms timescale via the chemical shift saturation recovery (CSSR) method. See Qing et al., Assessment of lung function in asthma and COPD using hyperpolarized 129Xe chemical shift saturation recovery spectroscopy and dissolved-phase MRI. NMR in biomedicine 2014a; 27(12):1490-1501; and Stewart et al., Experimental validation of the hyperpolarized 129Xe chemical shift saturation recovery technique in healthy volunteers and subjects with interstitial lung disease. *Magnetic resonance in medicine.* 2015; 74(1):196-207. As such, these studies were limited by relatively low temporal resolution, did not employ robust curve fitting methods for quantification, and did not investigate the dynamics of other spectral parameters.

While 3D gas exchange MRI provides important ways of characterizing the spatial distribution of gas exchange impairment, it alone may not be sufficient to determine the underlying cause. For example, dyspnea can be caused by interstitial lung disease, or underlying cardiac or pulmonary vascular disease. Even within PVD, it can be difficult to determine whether obstruction is pre-capillary or post-capillary and this becomes more difficult in the setting of other lung disease. Moreover, existing methods of evaluating PVD require invasive right heart catheterization. These problems are uniquely addressed noninvasively, by combining 3D $^{129}$Xe gas exchange MRI with evaluating the cardiopulmonary dynamics of $^{129}$Xe spectroscopy.

However, as recently as 2017, Bier et al., Proc. Intl. Soc. Mag. Reson. Med. 25 (2017) 2152, reported RBC chemical shifts that were not physically possible given the in vitro RBC chemical shift values. That is, generally anything below 214.5 is considered not physically possible. For example, the 2017 work showed RBC frequencies as low as 212 ppm. Embodiments of the present invention provide a robust acquisition and processing framework to provide clinically relevant RBC spectral parameters for dissolved phase $^{129}$Xe with improved quantification of spectral parameters. For example, the RBC chemical shift in seven healthy volunteers changed from 213.8±0.5 to 217.6±0.6 ppm and in IPF subjects it changed from 213.7±1.3 to 216.3±0.9 ppm using the improved processing methods and systems according to the present invention.

The inventors have found that to develop robust quantification methods and algorithms, one must confront the challenges posed by the complex underlying spectral structure of the $^{129}$Xe-Barrier resonance and/or the relatively low spectral resolution dissolved phase $^{129}$Xe signal oscillations. The inventors have also found that in addition to the variations in RBC amplitude, there are other dynamic $^{129}$Xe spectroscopic parameters (4-5 per resonance) that can be analyzed to provide insights into the underlying condition and/or distinguish between different conditions.

Comparison of a healthy cohort or cohorts (i.e., a population norm) can be used to provide insight into interpretations for patients with pulmonary vascular disease. Thus, embodiments of the present invention can provide: a) a strategy to acquire the temporal dynamics of $^{129}$Xe transfer with sufficient temporal and spectral resolution allowing for clinically useful and/or statistically reliable results, b) a robust analysis framework that quantifies dynamics such as cardiogenic oscillations, and c) representative data from healthy cohorts and patients with disease in order to facilitate clinical interpretation.

The population norm can be established using one or more healthy subjects, i.e., humans, and may be provided based on age and gender or just age or just gender.

Embodiments of the present invention successively acquire $^{129}$Xe free induction decays (FIDs) about every 5-400 ms, more typically about every 20 ms to about every 300 ms over a breathing maneuver to fully characterize the dynamics of each resonance (gas, barrier and RBC). This provides "dynamic spectroscopy", i.e., $^{129}$Xe NMR signal parameters over a time period associated with a breathing maneuver that includes at least one of inhale/breath-hold and exhale. Embodiments of the invention can then apply a complex time-domain curve fitting methodology and/or algorithm that can robustly quantify each $^{129}$Xe resonance (gas, barrier and RBC) by its amplitude, chemical shift, linewidth(s), and phase.

In some particular embodiments, a signal acquisition and processing algorithm and/or methodology can be used that accommodates the lower signal to noise (SNR) and spectral resolution of such dynamically acquired data in two ways. First, it can incorporate a tailored (defined) pre-processing step or steps to remove high-frequency noise outside of a physiologically plausible realm. Second, it can provide an innovative treatment of the $^{129}$Xe spectrum using curve fitting that is modeled with one or more non-Lorentzian line shapes, preferably requiring no more than one or two additional fitting degree of freedom (relative to only Lorentzian) to preserve temporal and/or spectral resolution.

In some currently preferred embodiments, the barrier resonance line shape is fit using a Voigt spectral profile, to incorporate its known complexity, while requiring only one additional fitting degree of freedom. The terms "Voigt spectral profile" and "Voight line shape" are interchangeably described herein as a "Voigt curve fitting function".

Embodiments of the invention can generate spectral parameters sensitive to gas exchange in the lung by acquiring the NMR raw signal data over the course of a breathing maneuver that can include each of inspiration/inhale, breath-hold, and exhalation/exhale.

FIG. 1 illustrates temporal changes in the spectroscopic parameters of the $^{129}$Xe gas, barrier, and RBC resonances in a representative healthy subject during inhalation, breath hold (gray bar/medial part of plot), and exhalation. In this graph/plot, all amplitudes were normalized to a maxima/maximum $^{129}$Xe barrier signal amplitude. For example, if the maximum barrier amplitude=10, and the maximum RBC amplitude=5, then the RBC graph would show a maximum signal of 0.5 while that of the barrier would exhibit a maximum amplitude of 1. This can be performed by first determining the value of the maximum barrier signal and then dividing the gas, barrier, and RBC signal amplitudes by this value. By way of another example, the maximum raw barrier signal can be a constant value of about 3.0×10$^3$ and every amplitude can be divided by this constant value. Alternatively, the RBC amplitude can be divided by the barrier amplitude at each time point to generate a time-depended RBC:barrier ratio, which is indicative of global gas exchange efficiency. The arrows in FIG. 1 emphasize/point to some of the spectroscopic changes that accompany the breathing maneuver and the line above the RBC amplitude (FIG. 1, FIG. 2 emphasizes/highlights the cardiogenic oscillations).

It is noted that other normalization factors may be used, such as normalizing to a $^{129}$Xe gas amplitude or a $^{129}$Xe gas resonance signal value (i.e., a maximal, minimal, median or average gas amplitude) or normalizing to any of these values for the barrier resonance.

Yet another way to normalize the amplitudes of the different spectral parameters can employ the barrier/gas phase with respect to time (i.e., normalize on a time-point by time-point basis). This results in a plot of the RBC:barrier ratio or the RBC:gas ratio with respect to time.

FIG. 1 illustrates temporal changes in the spectroscopic parameters of the $^{129}$Xe gas, barrier, and RBC resonances in a subject with IPF (subject 13) during inhalation, breath hold (gray bar), and exhalation. Again, all amplitudes are normalized to the maximum $^{129}$Xe signal in the barrier compartment. Unlike the healthy volunteer, the RBC resonance exhibits notable oscillations at the heart rate not only in amplitude but also in chemical shift and phase, as indicated by the black bar.

Figure 2:
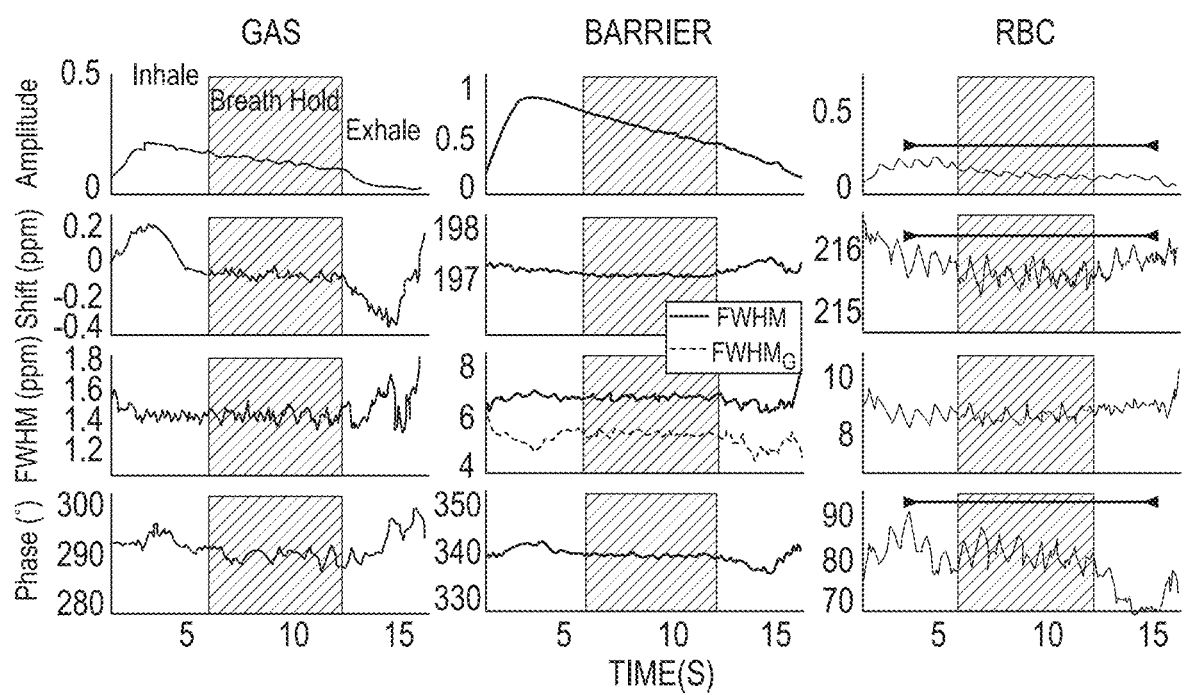
FIG. 2 are plots/graphs of temporal changes in spectroscopic parameters of the $^{129}$Xe gas (left side graphs), barrier (middle graphs) and RBC (right side graphs) resonances (normalized) in a representative subject with IPF during inhalation, breath hold and exhalation according to embodiments of the present invention FIG. 3 are plots/graphs of normalized and detrended RBC spectral parameter over time ("dynamics") during a breath hold from a healthy subject (left side graphs), two subjects with IPF, two subjects with PAH and two subjects with LHF, according to embodiments of the present invention.

FIG. 2 illustrates normalized and detrended RBC spectral parameter dynamics during a breath hold from a representative healthy volunteer and two subjects with IPF, and two subjects with PAH and one subject with left heart failure (LHF). The solid line represents the sinusoidal fit. Note larger RBC amplitude oscillations in IPF, coupled with larger RBC frequency/phase oscillations. By contrast, the PAH patients exhibit smaller RBC oscillations. The left heart (LHF) failure patient exhibits larger RBC amplitude oscillations, but decreased and/or no significant frequency (shift/ppm) and phase oscillations.

FIGS. 3A-4D illustrate peak-to-peak cardiogenic oscillations in RBC spectral parameters during the breath hold for healthy versus IPF subjects. Oscillations in the RBC amplitude, chemical shift, and phase are significantly larger for IPF subjects (red/broken line and on right side of plots) than for healthy volunteers (P=0.008, P=0.001, and P=0.002). *Statistical difference between groups (P<0.05).

FIGS. 5A-5D compare oscillations in the RBC amplitude, chemical shift, and phase between the healthy (green and left side data of each plot), IPF (red and middle of each plot) and PAH (magenta and right side data of each plot) cohort. IPF is distinguished by RBC amplitude, frequency and phase oscillations that are significantly larger than in the normal cohort. PAH is distinguished by RBC amplitude oscillations that are significantly smaller than in the normal cohort.

FIG. 6A is a set of dissolved phase fits for a large average of FIDs that exhibit minimal residual error for both 3-Lorentizan fits (left side plots) and barrier Voigt model fits (right side panels). FIG. 6B is a set of plots of dynamically acquired spectroscopy for a healthy volunteer that returns ill-condition fits for the barrier resonances in the 3-Lorentzian model (left and middle panels), but which is overcome by the barrier Voigt model (right side panels). The FWHM (ppm) panel of the barrier using the Voigt model has a $FWHM_G$ line and a Lorentzian line (the Lorentzian shown in solid line above the $FWHM_G$ line) which provides a more reliable RBC fit (FIGS. 1 and 2, for example).

In the past, Robertson et al proposed to manage the complexity of the barrier resonance by using two Lorentzian resonances rather than one. See, Robertson et al., Uncovering a third dissolved-phase $^{129}$Xe resonance in the human lung: Quantifying spectroscopic features in healthy subjects and patients with idiopathic pulmonary fibrosis. *Magnetic resonance in medicine* 2017; 78(4):1306-1315, the contents of which are hereby incorporated by reference as if recited in full herein. However, this approach yields poorly conditioned fits of dynamic spectroscopy because it requires more fitting degrees of freedom. The Voigt profile has a line shape that represents the convolution of a Lorentzian peak with a Gaussian distribution and requires only one additional fitting degree of freedom. Specifically, it returns two distinct linewidth parameters—a Lorentzian and a Gaussian parameter. See, Marshall et al., Use of Voigt lineshape for quantification of in vivo $^1$H spectra, *Magnetic resonance in medicine* 1997; 37(5):651-657, the contents of which are hereby incorporated by reference as if recited in full herein.

In other embodiments, other curve fitting functions that provide sufficient temporal and spectral resolution to yield accurate barrier resonance data can be used, i.e., the $^{129}$Xe spectrum can be modeled with one or more non-Lorentzian line shapes or a mixture of one or more non-Lorentzian and Lorentzian line shapes.

FIG. 7A is a set of color-coded images (ventilation, barrier:gas, RBC:gas) of a COPD patient with severe ventilation defects, but barrier uptake and RBC uptake are relatively well-matched. FIG. 7B is a set of corresponding color-coded images of a COPD patient in whom RBC transfer defects are disproportionately worse than the barrier uptake, suggesting possible pre-capillary pulmonary hypertension.

Figure 8A:
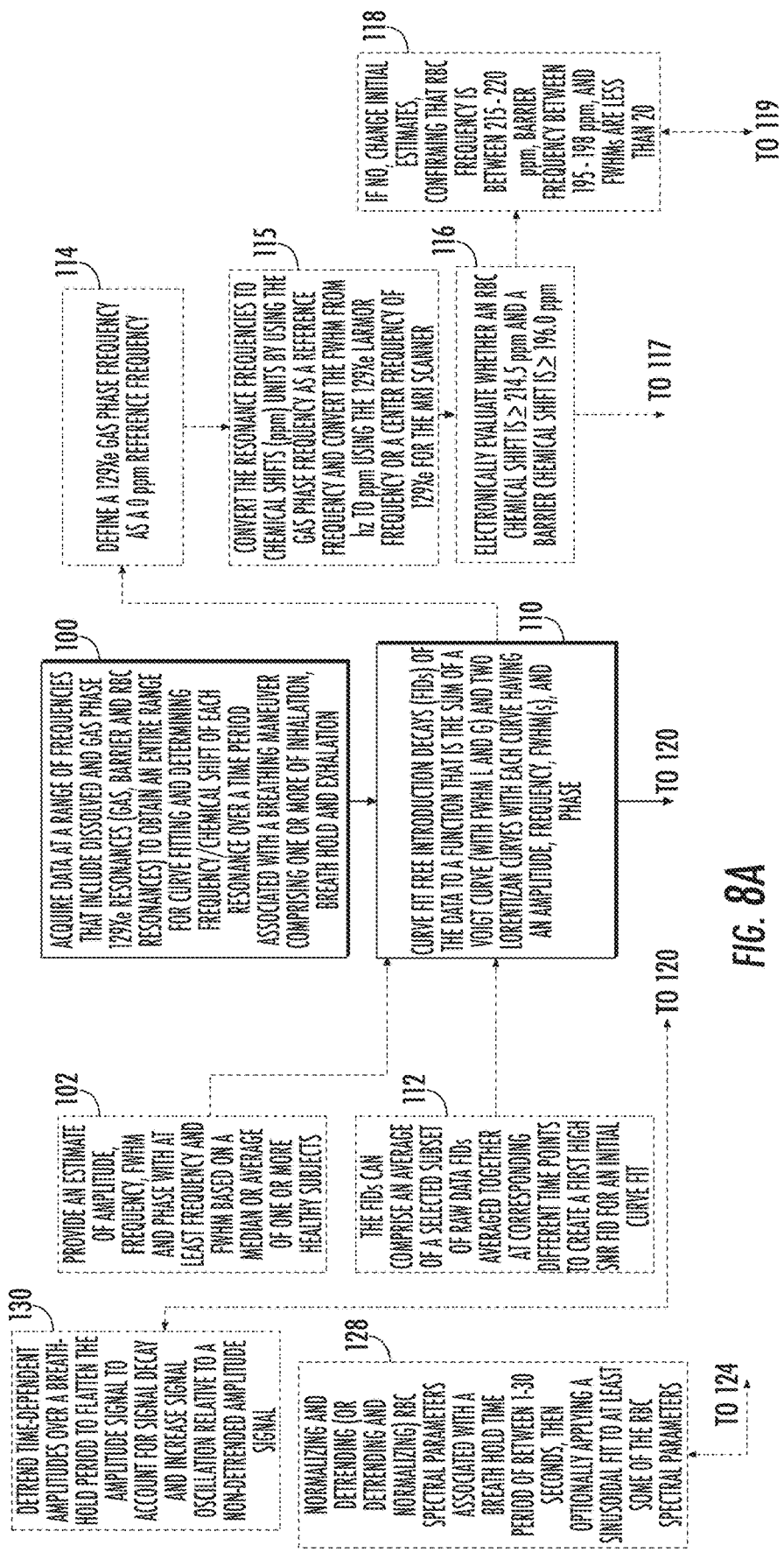
FIG. 8A is a flow chart of actions that can be used to carry out embodiments of the present invention.
Figure 8A:
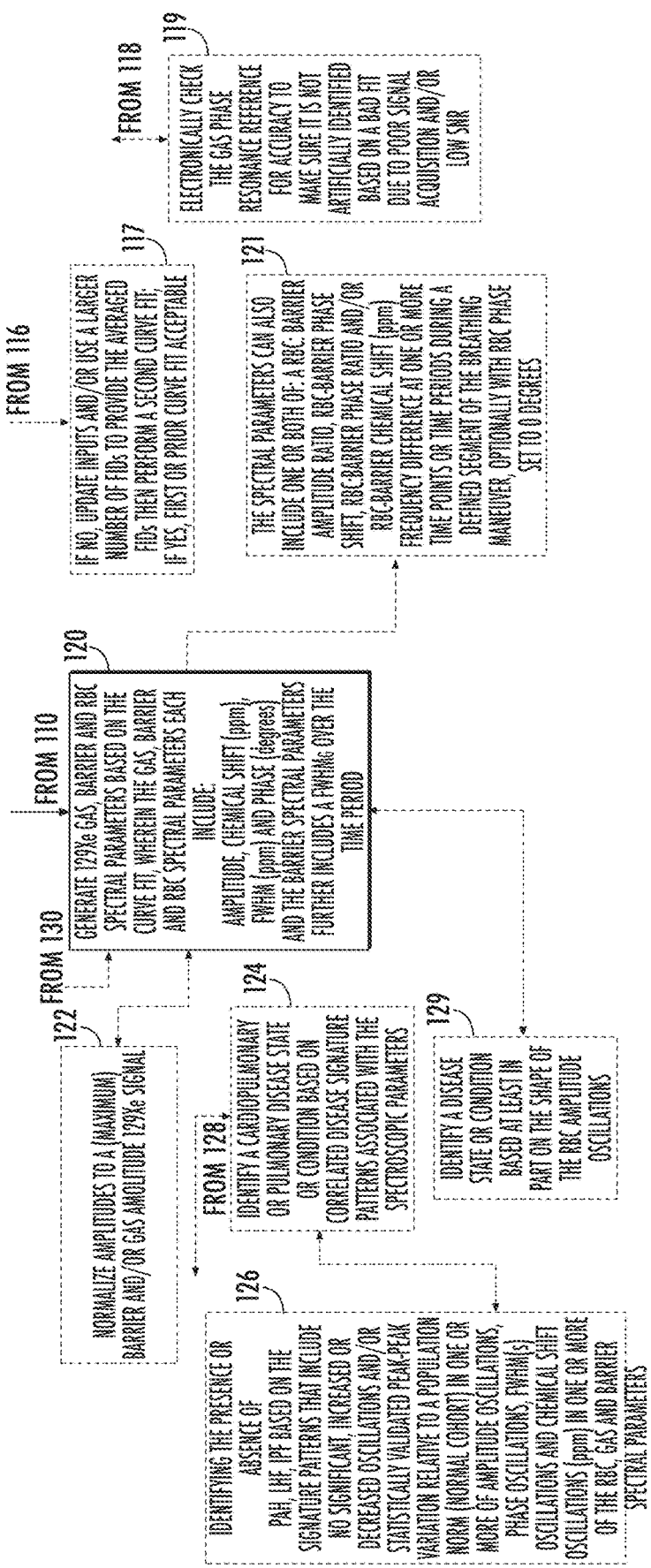

FIG. 8A is an example flow chart of signal processing actions that can be used to generate the dynamic spectral parameters according to embodiments of the present invention. Data at a range of frequencies is obtained. The data includes dissolved and gas phase $^{129}$Xe resonances (gas, barrier and RBC resonances) to obtain an entire range for curve fitting and determining frequency/chemical shift of each resonance over a time period associated with a breathing maneuver comprising one or more of inhalation, breath hold and exhalation. (block 100). Free Induction Decays (FIDs) of the obtained NMR signal over the time period are curve fit to a function that models the RBC and gas peaks as Lorenztian curves with an amplitude, frequency, FWHM, and phase, and the barrier resonances as a Voigt profile with an additional Gaussian FWHM (block 110). That is, the $^{129}$Xe barrier resonance can be modeled (or fit) using a Voigt line shape and the $^{129}$Xe-RBC and $^{129}$Xe-gas phase resonances can be modeled (fit) using (only) a respective Lorentzian line shape. The barrier resonance has only one frequency and fitting it to a Voigt function allows it to have concurrent Lorentzian and Gaussian FWHMs, but only one amplitude, frequency and phase. No independent Lorentzian and Gaussian curves are required; the barrier signal is simply fit to a single line shape that has two linewidth parameters. This accommodates the complexity of the barrier line shape while limiting the additional required fitting degrees of freedom. The curve fitting can be carried out to identify barrier versus RBC versus gas signal in a manner that minimizes error between the model functions and the data.

$^{129}$Xe gas, barrier and RBC spectral parameters are generated based on the curve fit: the gas, barrier and RBC spectral parameters each include amplitude, chemical shift (ppm), FWHM (ppm) and phase (degrees) and the barrier spectral parameter further includes a $FWHM_G$ over the time period (block 120).

An estimate of amplitude, frequency, FWHM and phase with at least frequency and FWHM based on a median or average of one or more healthy subjects can be provided and used as initial inputs for the curve fitting (block 102).

The FIDs can comprise an average of a selected subset of raw data dynamic FIDs averaged together at corresponding different time points to create a first high SNR FID for an initial curve fit (block 112). For example, 3-10 FIDs, such as 3, 4, 5, 6, 7, 8, 9 or 10 FIDs averaged together at corresponding time points during a breathing maneuver to improve SNR.

Amplitudes can be normalized to a (maximum) barrier amplitude and/or gas amplitude $^{129}$Xe signal (block 122).

A $^{129}$Xe gas phase frequency can be defined as a 0 ppm reference frequency (block 114).

The resonance frequencies can be converted to chemical shifts (ppm) units by using the gas phase frequency as a reference frequency and convert the FWHM from hertz to ppm using the $^{129}$Xe Larmor frequency or a center frequency of $^{129}$Xe for the MRI scanner (block 115). For example, if the scanner transmitter frequency is 34 MHz and gas-phase signal is detected at 0 Hz, while RBC signal is detected at 7.378 kHz, the RBC chemical shift is 7.378 kHz/34 MHz or 217 ppm.

The curve fit results can be electronically evaluated to determine whether an RBC chemical shift is ≥214.5 ppm and a barrier chemical shift is ≥196.0 ppm (block 116). If this condition is not met, then the original estimates or inputs can be updated and/or a larger number of FIDs can be used to provide the averaged FID for a revised first high SNR FID, then a second curve fit can be performed (block 117). If yes, the curve fitting is acceptable and no iterative change or further curve fitting or adjustment is required. If no, initial estimates can be updated/revised. Also, RBC frequency can be evaluated to confirm it is in a range of 215-220 ppm, and the barrier frequency can be evaluated to confirm it is in a range of 195-198 ppm, and FWHMs can be evaluated to confirm they are less than 20 (block 118).

The frequency (chemical shift) of the gas phase reference can also be electronically evaluated for accuracy to make sure it is not artificially identified based on a bad fit due to poor signal acquisition and/or low SNR (block 119).

A cardiopulmonary or pulmonary disease state or condition can be identified based on correlated disease signature patterns associated with the dynamic $^{129}$Xe spectroscopic parameters (block 124).

A likelihood of a presence or absence of PAH, LHF, IPF can be identified based on the signature patterns that include no significant, increased or decreased oscillations and/or statistically validated peak-peak variation relative to a population norm (normal cohort) in one or more of: amplitude oscillations, phase oscillations, FWHM(s) oscillations and chemical shift oscillations (ppm) in one or more of the RBC, gas and barrier spectral parameters (block 126).

Amplitudes of spectral parameters associated with a breath-hold time period of between 1-30 seconds can be normalized and detrended, then optionally a sinusoidal fit can be applied to at least some of the RBC spectral parameters (block 128).

A disease state or condition can be identified based at least in part on the shape of the RBC amplitude oscillations (block 129). Embodiments of the present application contemplate that the actual shape of the RBC oscillations can reveal information of an underlying disease state or condition. The RBC oscillations are not (always) purely sinusoidal and the way the oscillations rise and fall can provide information about the underlying disease condition.

Time-dependent amplitudes can be detrended over a breath-hold period to flatten the amplitude signal to account for signal decay and increase signal oscillation relative to a non-detrended amplitude signal (block 130). That is, the RBC spectral parameters can be normalized and detrended or detrended and normalized. The breath hold time period can be between 1-30 seconds. Optionally, a sinusoidal fit can be applied to at least some of the (adjusted) RBC spectral parameters.

Figure 8B:
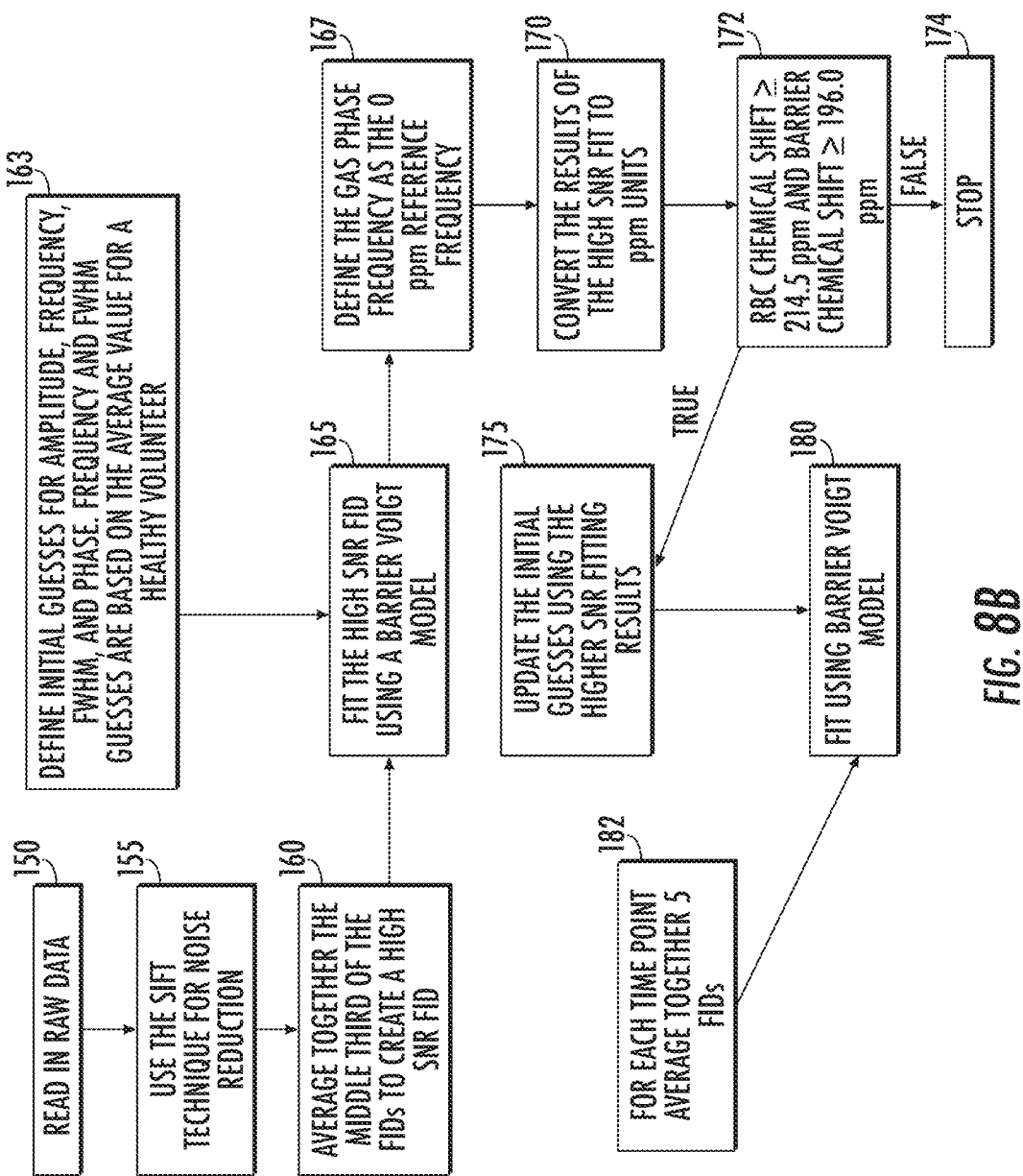
FIG. 8B is a flow chart of actions that can be used to carry out embodiments of the present invention.

FIG. 8B is another example flow chart according to embodiments of the present invention. Raw data is read in (obtained) (block 150). A SIFT technique can be applied for noise reduction (block 155). See, Doyle et al., SIFT, a postprocessing method that increases the signal-to-noise ratio of spectra which vary in time, *Journal of Magnetic Resonance, Series B*. 1994; 103(2):128-133; and Rowland et al., AP, Spectral improvement by fourier thresholding of in vivo dynamic spectroscopy data. *Magnetic resonance in medicine*. 2015, the contents of which are hereby incorporated by reference as if recited in full herein.

Optionally, the middle third of FIDs of the raw data can be averaged together to create a high SNR FID (block 160). Initial estimates (guesses) for amplitude, frequency, FWHM, $FWHM_G$, and phase are provided/defined (block 163). Initial guess/estimates for a high-SNR FID can be provided as a first curve fit iteration and the outcome of that that fit used to provide updated guesses for smaller blocks of averages that contain the dynamics.

Frequency and FWHM and $FWHM_G$ estimates can be based on an average (or median) value of a healthy cohort (block 163). The high SNR FID can be fit using a barrier Voigt model (block 165). The gas phase frequency can be defined as the 0 ppm reference frequency (block 167). The results of the high SNR fit can be converted to ppm units (block 170).

The RBC chemical shift can be evaluated to confirm it is ≥214.5 ppm and the barrier chemical shift can be evaluated to confirm it is ≥196.0 ppm (block 172). If these conditions are not met (false), the fitting can stop (block 174). For example, a stop decision can be made based on a number of tries or a defined SNR threshold. If true, the initial estimates/guesses can be updated using the results from a higher SNR fitting and/or a higher SNR FID (block 175). The high or a higher SNR FID can be fit with the updated guesses/estimates (block 180). Each time point of the high SNR FID can have 5 FIDs averaged together (block 182). While 5 FIDs are believed to provide sufficient resolution, fewer FIDs can be averaged together, such as 3 or 4 FIDs, or more than 5, such as a range of 6-10, for certain embodiments.

Figure 8C:
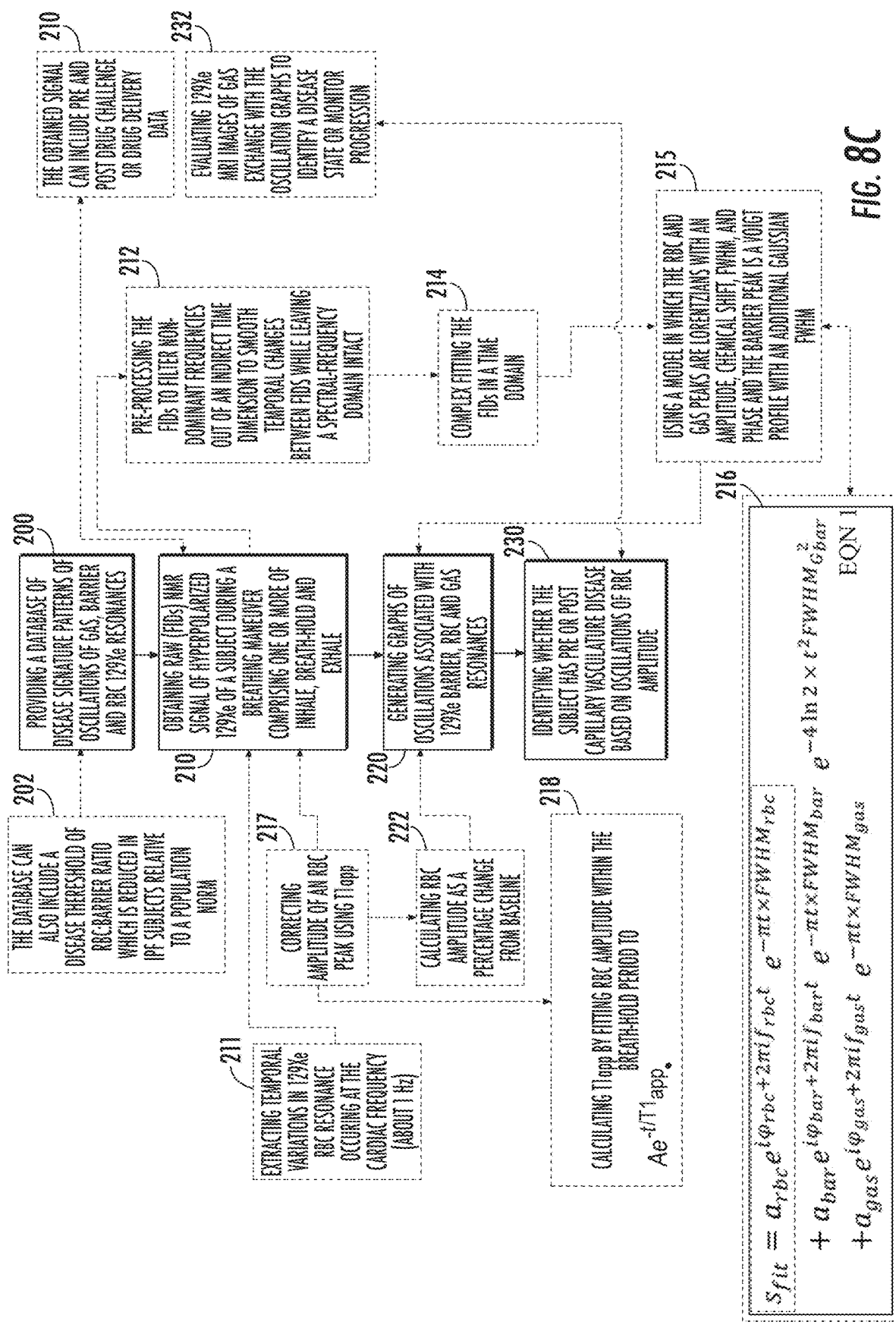
FIG. 8C is a flow chart of actions that can be used to carry out embodiments of the present invention.

FIG. 8C is another flow chart of actions that can be used to evaluate a subject according to embodiments of the present invention. A database of disease signature patterns of oscillations of gas, barrier and RBC 129Xe resonances is provided (block 200).

Raw (FIDs) of NMR signal of hyperpolarized $^{129}$Xe of a subject during a breathing maneuver comprising one or more on inhale, breath-hold and exhale are obtained (block 210).

Graphs of oscillations associated with $^{129}$Xe barrier, RBC and gas resonances are generated (block 220).

The subject can be identified as having pre or post capillary pulmonary vasculature disease based on oscillation the oscillations of RBC chemical shift and RBC amplitude (block 230). For example, only patients with pure pre-capillary disease benefit from PH medication while those with any post-capillary obstruction are contradicted from treatment using PH medication so proper characterization is important.

The database can also include a disease threshold of RBC:Barrier ratio which is reduced in IPF subjects relative to a population norm (block 202).

The FIDs or the averaged FID can be pre-processed to filter non-dominant frequencies (i.e., frequencies associated with noise) out of an indirect time dimension to smooth temporal changes between FIDs while leaving a spectral-frequency domain intact (block 212).

The FIDs or the averaged FID can be complex fitted in a time domain (block 214).

A model in which the RBC and gas peaks are Lorentzians with an amplitude, chemical shift, FWHM and phase and the barrier peak is a Voight profile with an additional Gaussian linewidth ($FWHM_G$) for the barrier resonance (block 215).

The curve fitting can be carried out using the equation $S_{fit}$, below (block 216).

$$S_{fit} = a_{rbc}e^{i\varphi_{rbc}+2\pi i f_{rbc}t}e^{-\pi t \times FWHM_{rbc}} + \quad \text{EQN(1)}$$
$$a_{bar}e^{i\varphi_{bar}+2\pi i f_{bar}t}e^{-\pi t \times FWHM_{bar}}e^{-4\ln 2 \times t^2 FWHM_{G_{bar}}^2} +$$
$$a_{gas}e^{i\varphi_{gas}+2\pi i f_{gas}t}e^{-\pi t \times FWHM_{gas}}$$

Temporal variations in $^{129}$Xe RBC resonance occurring at the cardiac frequency (about 1 Hz) can be extracted (block 211).

Amplitude of an RBC peak can be corrected using T1app (block 217).

T1app can be calculated by fitting RBC amplitude within the breath-hold period to $Ae^{-t/T1_{app}}$ (block 218).

Stated differently, the amplitude "A" of the RBC signal can be corrected by dividing the signal by $\exp(-t/T1_{app})*\exp(-t_{start}/T1_{app})$, where the second term is a scaling term to adjust the amplitude to match with the raw signal. The signal amplitude is in arbitrary units.

The RBC amplitude can be calculated as a percent change from baseline (block 222). For example, the RBC signal during the breath hold can be fit to the function of block 216. Then the value of the function at each time point, t, can be calculated and used as the baseline. The RBC baseline can be viewed as a percent change by taking the difference between the measured value and the calculated value and dividing by the calculated value. Baseline can be defined as the result of the exponential decay fitting in block 218 and is essentially a percentage change from a large average over many oscillations:

(RBC_signal−RBC_fitted)/RBC_fitted    EQN 2

The action at block 222 can use the corrected amplitude from block 217.

The obtained signal can include pre and post drug challenge or drug delivery data (block 210).

$^{129}$Xe MRI images of gas exchange can be evaluated with the oscillation graphs to identify a disease state or monitor progression (block 232).

The oscillation frequency can be used to determine a subject's heart rate.

Static values of one or more of the spectral parameters can also be evaluated to obtain information regarding different disease states and/or conditions, alone or in combination with one or more of the dynamic spectral parameters.

Figure 8D:
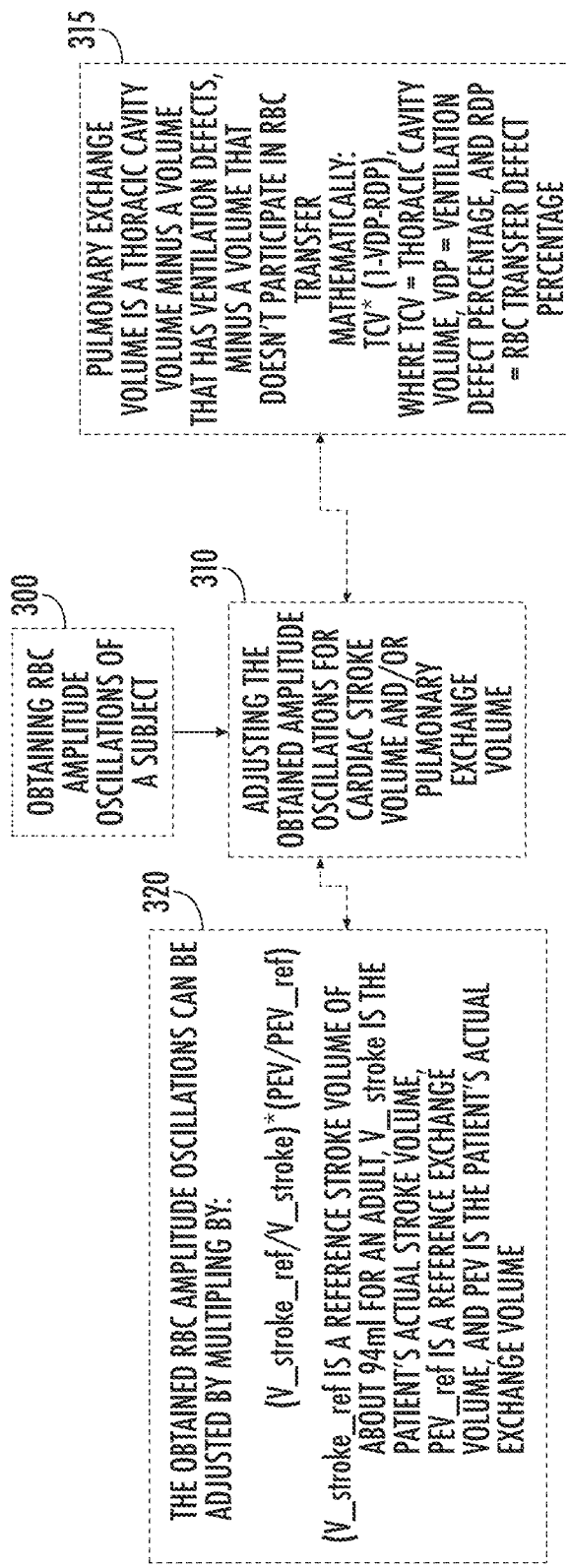
FIG. 8D is a flow chart of actions that can be carried out to adjust RBC amplitude oscillation values according to embodiments of the present invention.

FIG. 8D is a flow chart of actions that can be used to adjust amplitude of RBC oscillations which may be important to interpreting RBC amplitude oscillations. RBC amplitude oscillations of a subject are obtained (block 300). The obtained RBC oscillations can be adjusted for cardiac stroke volume and a new parameter referred to as "pulmonary exchange volume" (block 310).

Stroke volume is the volume of blood the right side of the heart pumps out with each beat. A nominal (human adult) value is commonly reported as 94 or 95 ml. All things being equal, a larger cardiac stroke volume is likely to generate larger RBC amplitude oscillations. Stroke volume can be determined invasively from right heart catheterization, measured by ventricle volumes from an echocardiogram, or determined non-invasively from a certain type of time-resolved proton cardiac MRI acquisition. See, Alfakih, Khaled, et al. "Normal human left and right ventricular dimensions for MRI as assessed by turbo gradient echo and steady-state free precession imaging sequences." *Journal of Magnetic Resonance Imaging* 17.3 (2003): 323-329. Absent such data, it may be estimated from alometric scaling principles. See, de Simone, Giovanni, et al. "Stroke volume and cardiac output in normotensive children and adults: assessment of relations with body size and impact of overweight." *Circulation* 95.7 (1997): 1837-1843. The contents of these articles are hereby incorporated by reference as if recited in full herein.

Information from the shape of the RBC oscillation amplitude can be used to potentially help differentiate pure pre-capillary disease from post-capillary disease versus combined post- and pre-capillary pulmonary hypertension (Cpc-PH).

"Pulmonary exchange volume" is a measure of the lung volume receiving blood from the stroke volume. For a given stroke volume, a larger pulmonary exchange volume will attenuate the RBC amplitude oscillations.

Pulmonary exchange volume ("PEV") can be derived from $^{129}$Xe gas exchange MRI. It can be modeled as a thoracic cavity volume minus the volume that consists of ventilation defects, minus the volume that doesn't participate in RBC transfer.

Mathematically:

$$PEV=TCV*(1-VDP-RDP), \quad \text{EQN 3}$$

where TCV=thoracic cavity volume, VDP=ventilation defect percentage, and RDP=RBC transfer defect percentage. VDP and RDP can be calculated from the gas exchange $^{129}$Xe MRI images (see, FIGS. 7A, 7B). (block 315)

For example, a subject with 4 liter thoracic cavity, with 10% VDP+10% RDP has 80%×4 liter=3.2 liters of pulmonary exchanging volume.

Embodiments of the invention contemplate that the dynamic spectroscopic RBC amplitude oscillations can be multiplied by a pulmonary exchange volume and divided by cardiac stroke volume.

Cardiac stroke volume can also be measured by ventricle volumes from an echocardiogram. Alternatively, published normative values of 94 or 95 mL or other defined normative values based on allometric scaling can be used. For example, stroke volume is calculated by dividing cardiac output by heart rate. Cardiac output scales with body mass to the power of ¾, while heart rate scales to the power of −¼. Thus, stroke volume is expected to scale linearly with body mass.

A larger blood volume will naturally diminish RBC amplitude oscillations, whereas a larger cardiac stroke volume would enhance the RBC amplitude oscillations. This suggests that in patients with IPF, who often have a very small restricted thoracic cavity, enhanced RBC oscillations are likely a natural consequence of reduced exchangeable blood volume.

The "adjusted" RBC amplitude oscillations can multiply the obtained (i.e., originally measured) RBC amplitude oscillations $A_{RBC}$ by:

(V_stroke_ref/V_stroke)*(PEV/PEV_ref).    EQN 4 where V_stroke_ref is a reference stroke volume like 94 ml or 95 ml (adult), V_stroke is the patient's actual stroke volume, PEV_ref is a reference exchange volume, and PEV is the patient's measured exchange volume (block 320).

Referring again to FIG. 3, for example, a subject can be identified as having IPF which is characterized by RBC amplitude oscillations that are significantly larger (i.e., about 1.5-2× larger) than in healthy volunteers. In IPF patients, the RBC frequency (chemical shift/ppm) and phase oscillations are also significantly larger than in the healthy cohort, typically at least 2×, 3×, 4× or 5× above a healthy cohort. In the IPF versus healthy cohort, RBC amplitude variations were nearly twice as high (16.8±5.2% vs 9.7±2.9%; P=0.008), chemical shift oscillations were more than 5-fold higher (0.43±0.33 ppm vs 0.083±0.05 ppm; P<0.001), and RBC phase oscillations were more than 5-fold higher (7.7±5.6° vs 1.4±0.8°; P<0.001).

In IPF, the RBC amplitude oscillations are thought to be large because the pulmonary exchange volume, PEV, is so small. It is contemplated that when RBC oscillations are corrected for PEV, they will potentially significantly decrease. Thus, more specific diagnostic features of dynamic spectroscopy in patients with IPF are the chemical shift and phase oscillations, which do not require correction for PEV. To date, such oscillations have only been seen in patients with IPF.

It is contemplated that the larger RBC amplitude oscillations are either the result of post-capillary obstruction caused by fibrosis, or cardiac output being delivered to a significantly smaller capillary blood volume. Importantly, the RBC frequency and phase oscillations are expected to be caused by delayed oxygenation associated with interstitial lung disease. This is uniquely detectable by virtue of the sensitivity of the $^{129}$Xe-RBC resonance to blood oxygenation. The observation that this frequency oscillates in the IPF cohort is a measure of interstitial thickening that causes delayed diffusion of oxygen.

Figure 3:
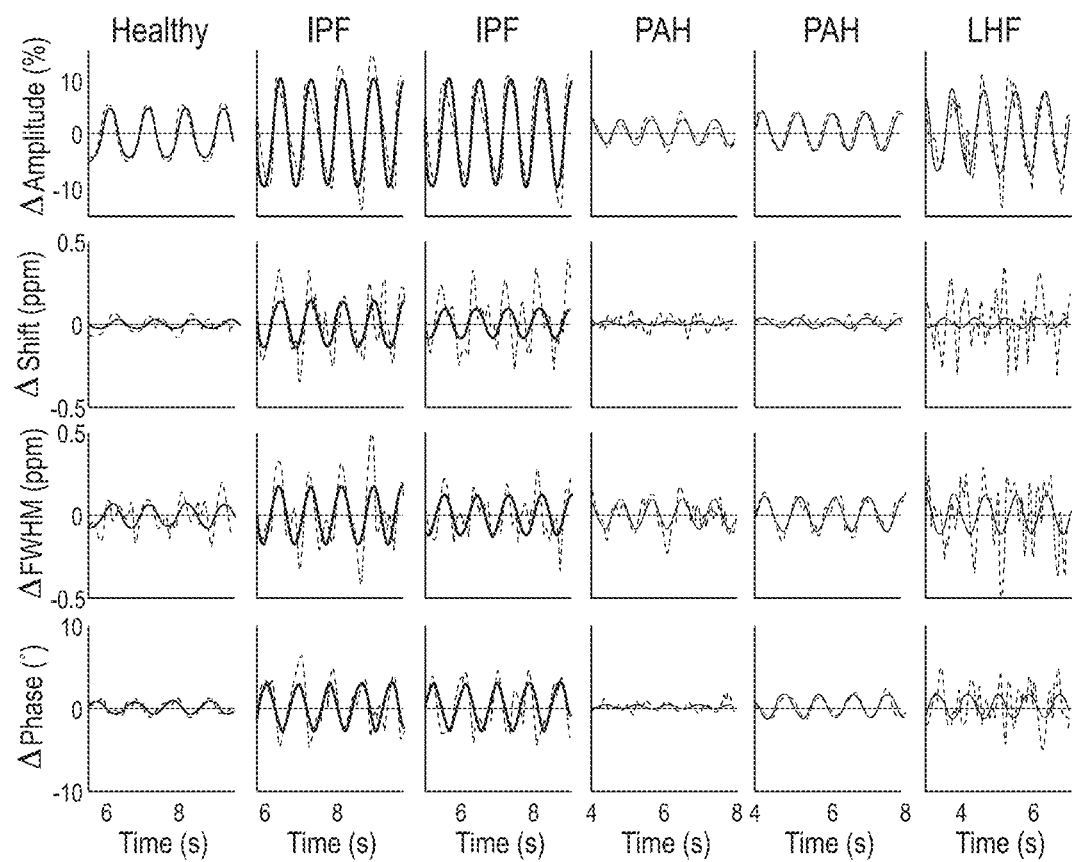
Figure 4A:
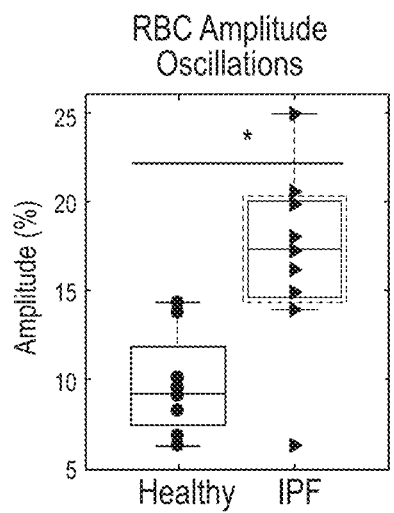
FIGS. 4A-4D are plots/graphs that compare peak-to-peak cardiogenic oscillations in RBC spectral parameters during a breath hold for healthy versus IPF subjects according to embodiments of the present invention.
Figure 4C:
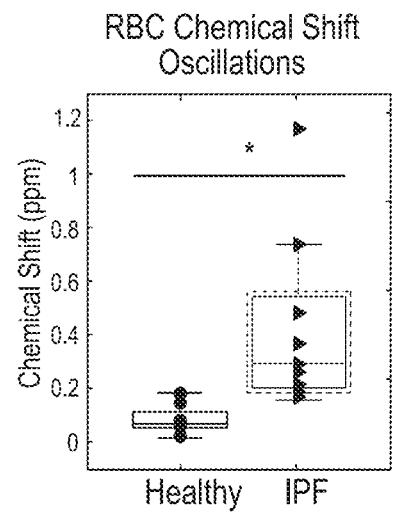
Figure 4B:
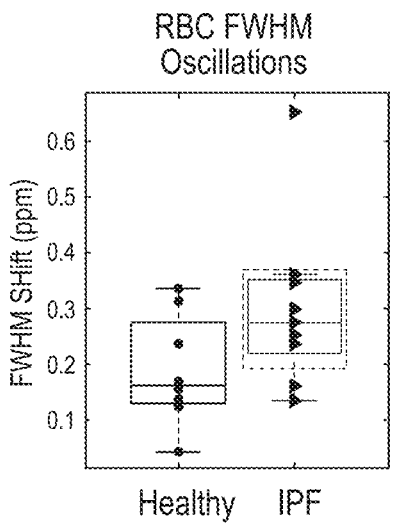
Figure 4D:
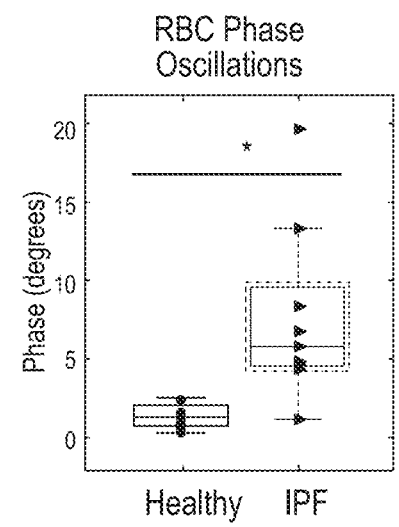
Figure 5A:
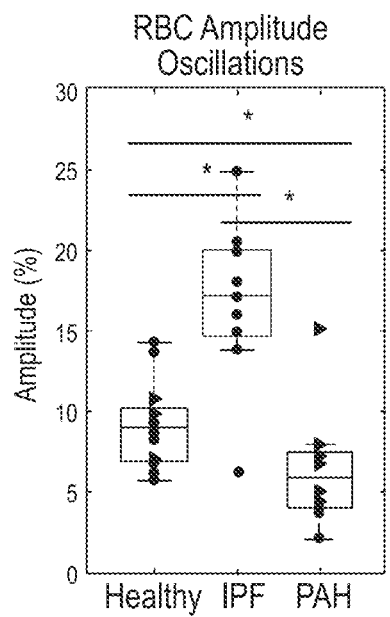
FIGS. 5A-5D are plots/graphs that compare oscillations in RBC spectral parameters for healthy versus IPF and PAH cohorts/subjects according to embodiments of the present invention.
Figure 5C:
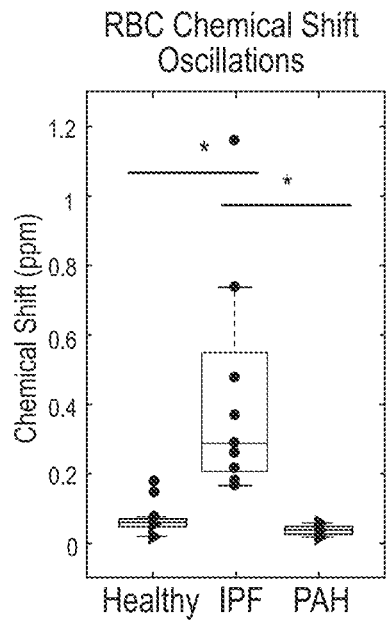
Figure 5B:
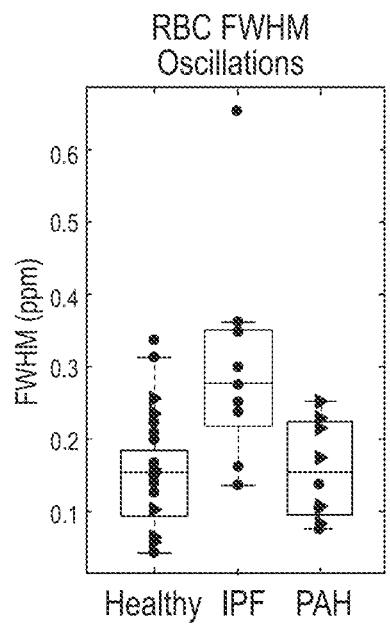
Figure 5D:
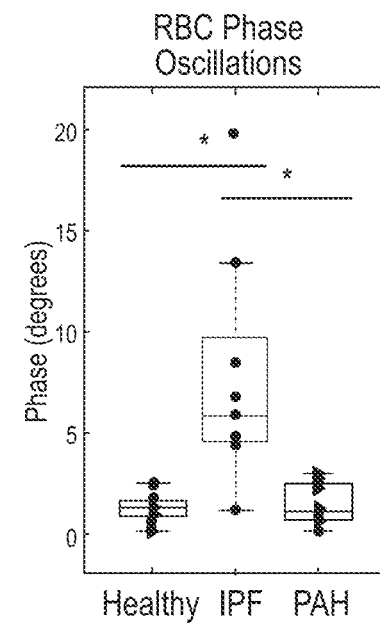

The PAH cohort can be characterized as exhibiting RBC oscillations that are significantly smaller than the normal cohort (FIG. 3). Moreover, Group 1 PH does not exhibit RBC chemical shift or phase oscillations that are significantly different from normal.

These findings are particularly noteworthy in the small population used to generate the dynamic spectroscopy parameters for patients with the noted conditions (i.e., IPF, PAH and LHF) because these patients are on medication and are relatively well-controlled compared to patients who would present for diagnosis.

Although not wishing to be bound by any particular theory, the smaller RBC amplitude oscillations are explained by higher impedance in the pulmonary arteries and arterioles, which serves to attenuate the changes in capillary blood volume that occur at diastole.

PH can exhibit large RBC amplitude oscillations, but with little or no RBC frequency/phase oscillations. The enhanced RBC amplitude oscillations are thought to be a marker of post-capillary obstruction.

RBC frequency/phase oscillations appear to be uniquely associated with delayed oxygenation that occurs in interstitial lung disease, particularly IPF.

It is not yet known if the RBC frequency/phase oscillations are associated with non-specific interstitial pneumonia, but it is contemplated that this form of pneumonia can be differentiated from IPF based on the $^{129}$Xe spectral parameters, dynamic, static or dynamic and static $^{129}$Xe spectral parameters relative to a patient population and "healthy cohort" or population norm.

In some particular embodiments, it is contemplated that the defined different disease patterns can distinguish post-capillary vascular disease from pre-capillary vascular disease by variations above or below a healthy cohort or population norm.

Embodiments of the invention can use decreased peak to peak RBC amplitude oscillations relative to a defined norm to indicate PAH.

Embodiments of the invention can evaluation the shape of the RBC amplitude oscillations to indicate a combined pre- and post-capillary vascular disease state.

Diminished RBC amplitude oscillations appear to be a unique signature of pre-capillary, arterial disease, and patients exhibiting these may benefit from PAH medications.

Enhanced RBC amplitude oscillations are likely a signature of post-capillary disease and these patients would be harmed by receiving PAH medications.

It is contemplated that there are several potential ways to acquire dynamic spectroscopy data that improve upon standard acquisition.

Embodiments of the invention may be able to detect potentially treatable pre-capillary PH in patients who have existing lung disease (like COPD, IPF, etc. . . . ) based on gas exchange MRI (i.e., FIGS. 7A, 7B). That is, patients with impaired RBC transfer that affects a disproportionately larger percentage of the lung than can be explained by poor barrier condition (low barrier in COPD, or high barrier in IPF) and gas exchange $^{129}$Xe MRI can be used to identify additional feature characteristics.

Embodiments of the invention can acquire gas exchange MRI and/or dynamic spectroscopy before and after administration of a pharmaceutical agent, such as a vasodilator, hyperoxia, diuretic or prostacyclins. Comparison of changes in oscillations in the spectral parameters of $^{129}$Xe dynamic spectroscopy, for example, can be detected to determine impact of the agent on function. For example, delivery of inhaled nitric oxide or inhaled prostacyclins may be able to reveal areas in gas exchange images of the lung that are susceptible to vasodilation which would show restored RBC transfer. Similarly, dynamic spectroscopy can show enhanced/increased RBC oscillation amplitudes relative to prior to such administration.

A hyperoxia challenge may also reveal similar improvements in restoring regional RBC transfer and RBC oscillation amplitudes.

In some COPD patients, massively diminished RBC amplitude oscillations are present even after correcting for the relatively large exchangeable capillary blood volumes. This could indicate pre-capillary pulmonary hypertension.

Figure 9:
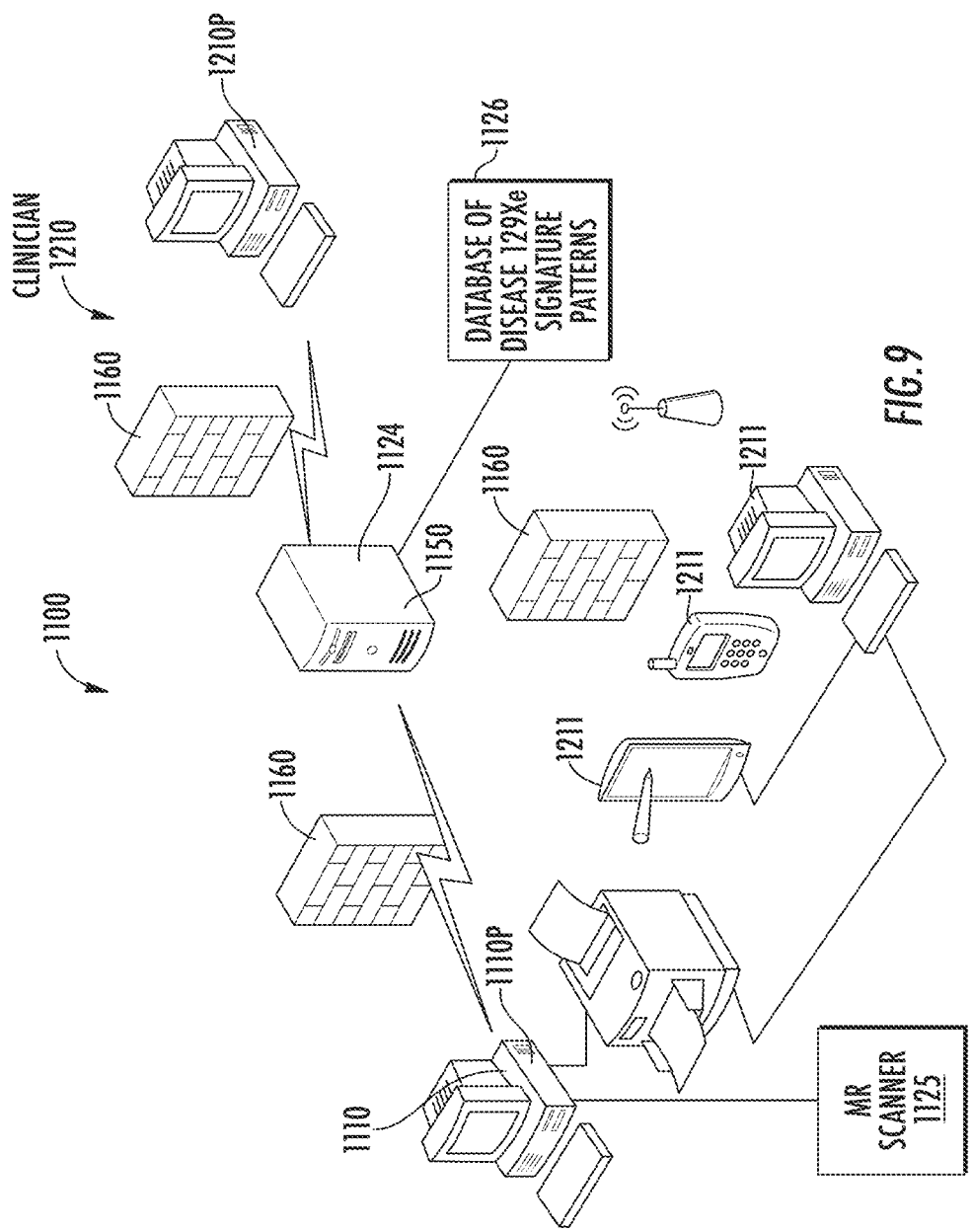
FIG. 9 is a block diagram of data processing systems that may be used to identify different disease states using defined signatures of multiple $^{129}$Xe spectroscopic parameters associated with oscillations of RBC and/or barrier plots accordance with some embodiments of the present invention.

Turning now to FIG. 9, an example medical system 1100 is shown. The medical system 1100 can comprise at least one server 1150. The at least one server 1150 can be configured with a dynamic $^{129}$Xe spectroscopy analysis module 1124 and/or be configured with a database of $^{129}$Xe disease signature patterns 1126.

The at least one server 1150 can communicate with an imaging site 1110 and/or a clinician site 1210, typically via at least one respective digital processor 1110p, 1210p. The imaging site 1110 can be a hospital or other facility (mobile or permanent) with an MRI Scanner 1125. The clinician site 1210 can be remote from or at the imaging site 1110. The server 1150 can be remote from both the imaging site 1110 and the clinician site 1210. Alternatively, the server 1150 can be onsite either the clinician or imaging site 1210, 1110, respectively.

The server 1150 can be integrated into a single server or may be distributed into one or more servers or other circuits or databases at a single physical site or at spatially separate locations. Similarly, the dynamic $^{129}$Xe spectroscopy analysis module 1124 held by the one or more servers 1150 can be distributed in multiple processors or databases or integrated into one. The $^{129}$Xe dynamic spectra can be electronically transmitted using a DICOM system to the 1150 server for the automated image analysis.

The server 1150 may be embodied as a standalone server or may be contained as part of other computing infrastructures. The server 1150 may be embodied as one or more enterprise, application, personal, pervasive and/or embedded computer systems that may be standalone or interconnected by a public and/or private, real and/or virtual, wired and/or wireless network including the Internet, and may include various types of tangible, non-transitory computer-readable media. The server 1150 may also communicate with a computer network via wired or wireless connections, and may include various types of tangible, non-transitory computer-readable media.

The server 1150 can be provided using cloud computing which includes the provision of computational resources on demand via a computer network with appropriate firewalls 1160 and privacy protocols to comply with HIPPA or other regulatory requirements. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

A plurality of the imaging sites 1110 can be in communication with the server 1150 and one or more clinician sites 1210. The server 1150 can receive and analyze NMR data of respective patients from different sites 1110 at any one time. It is contemplated that the server 1150 can analyze and generate patient reports in a FIFO (first in first out) manner, optionally with rush or ranked priority reviews. Multiple analyses can be performed concurrently or serially at the server 1150 or other devices in communication with the server 1150 and associated reports can be generated and transmitted to one or more devices of clinician users 1211.

An imaging site 1110 and/or a clinician site 1210 can communicate with the server 1150 via a computer network, such as one or more of local area networks (LAN), wide area networks (WAN) and can include a private intranet and/or the public Internet (also known as the World Wide Web or "the web" or "the Internet."

The server 1150 can be configured to send analysis reports or subject-test or evaluation data to one or more clinician devices 1211 such as computers, tablets or smartphones (shown as at the imaging site but one or more may be remote from the imaging site).

Figure 10:
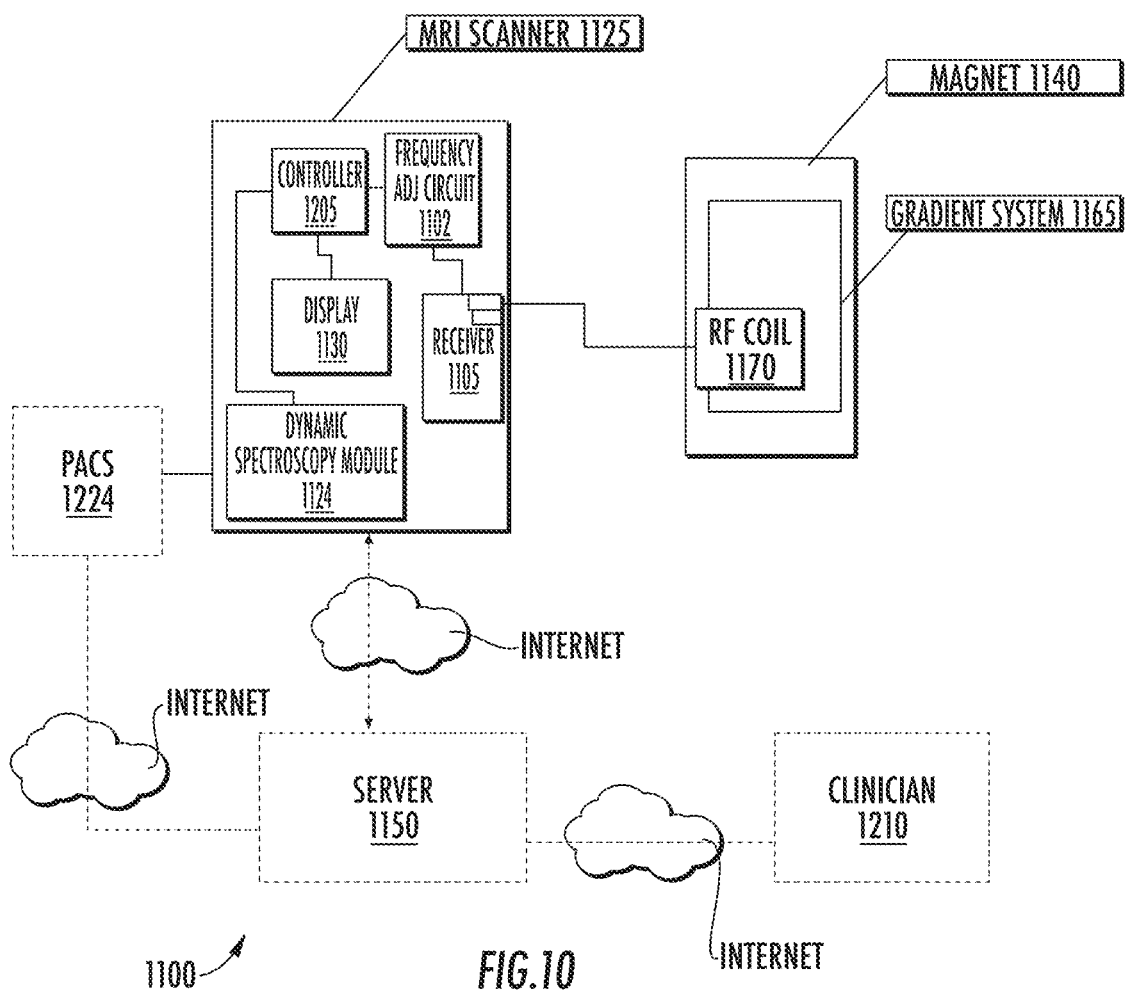
FIG. 10 is a schematic illustration of a medical evaluation system in communication with an MRI imaging system according to embodiments of the present invention.

FIG. 10 is a schematic diagram of an MRI scanner 1125 with a superconducting magnet 1140, a gradient system 1165 and an RF coil 1170 that communicates with an RF amplifier (not shown) associated with the MRI scanner as is well known to those of skill in the art. Signal from the RF coil 1170 may be transmitted to the receiver 1205 via a cable (typically a BNC cable). The MRI scanner 1125 also includes a controller 1105, a frequency adjustor circuit 1102 that can tune the MRI scanner to generate a desired RF excitation frequency for exciting hyperpolarized dissolved phase $^{129}$Xe, and a display 1130. The display 1130 may be local or remote and may be provided as part of a clinician workstation. The display 1130 can be configured to display the RBC and barrier images substantially concurrently with plots of oscillation of $^{129}$Xe to provide clinical data of the gas-exchange regions of the lung.

The MRI scanner 1125 can also include or be in communication with a Dynamic Spectroscopy module 1224, which can programmatically communicate with the frequency adjustor circuit 1102 and receiver 1205 to electronically (automatically) switch operational modes, frequencies, phases and/or electronically direct the excitation and acquisition of appropriate signals, and generate the cardiopulmonary spectroscopic parameters according to some embodiments of the invention. Alternatively, the NMR signal data of respective subjects can be collected and transmitted to the server 1150 for post-acquisition processing. The NMR signal data can be transmitted from a PACS (picture archiving and communication system) 1224 to the server 1150.

Figure 11:
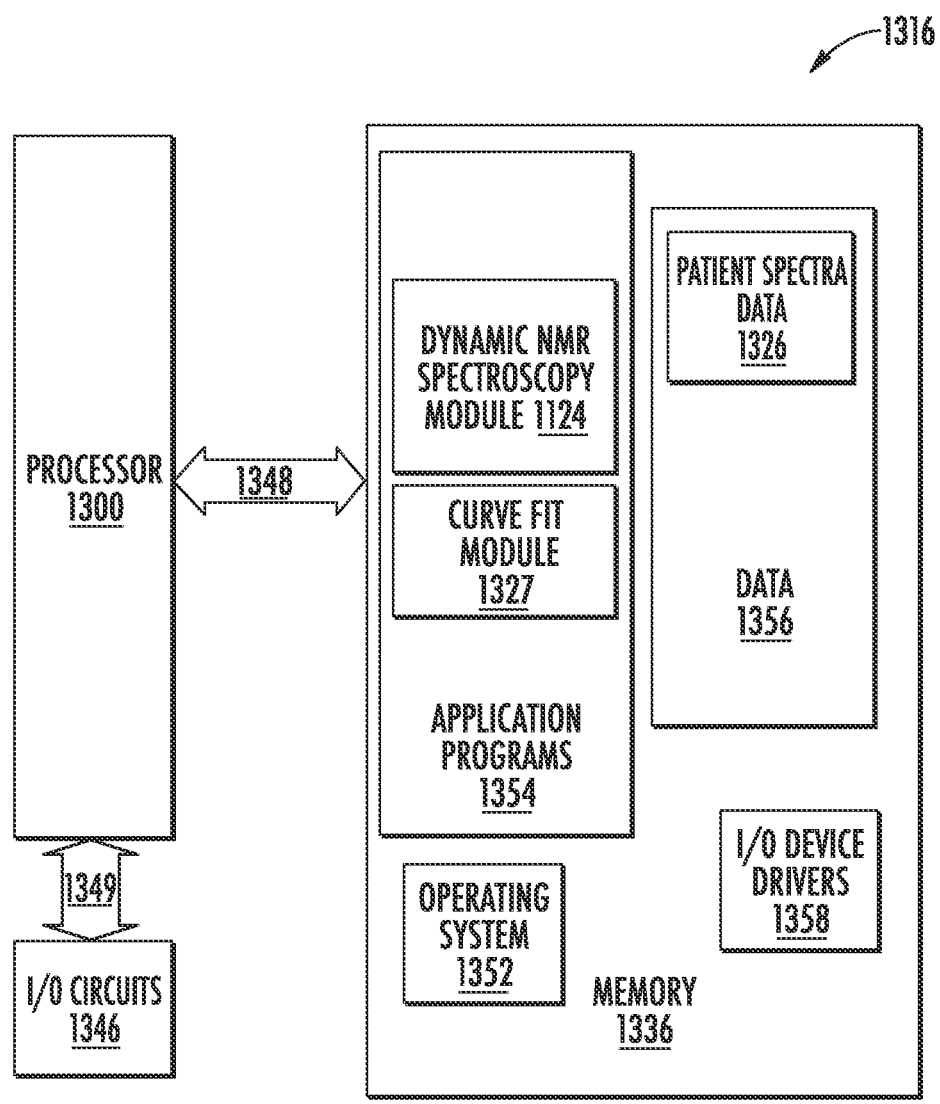
FIG. 11 is a block diagram of data processing systems according to embodiments of the present invention.

Referring now to FIG. 11, a data processing system 1316 is shown that may be used to provide the $^{129}$Xe dynamic spectroscopy module 1124 (which can provide dissolved phase $^{129}$Xe of gas exchange for NMR signal decomposition), and a curve fit module 1327. Thus, in accordance with some embodiments of the present invention, the system 1316 comprises a memory 1336 that communicate with a processor 1300. The data processing system 1316 may further include an input/output (I/O) circuits and/or data port(s) 1346 that also communicate with the processor 1300. The system 1316 may include removable and/or fixed media, such as floppy disks, ZIP drives, hard disks, or the like, as well as virtual storage, such as a RAMDISK. The I/O data port(s) 1346 may be used to transfer information between the data processing system 1316 and another computer system or a network (e.g., the Internet). These components may be conventional components, such as those used in many conventional computing devices, and their functionality, with respect to conventional operations, is generally known to those skilled in the art.

FIG. 11 illustrates a processor 1300 and memory 1336 that may be used in embodiments of systems in accordance with some embodiments of the present invention. The processor 1300 communicates with the memory 1336 via an address/data bus 1348. The processor 1300 may be, for example, a commercially available or custom microprocessor. The memory 1336 is representative of the one or more memory devices containing the software and data used for providing $^{129}$Xe MRI image data or $^{129}$Xe NMR spectra data in accordance with some embodiments of the present invention. The memory 1336 may include, but is not limited to, the following types of devices: cache, ROM, PROM, EPROM, EEPROM, flash, SRAM, and DRAM.

As shown in FIG. 11, the memory 1336 may contain up to two or more categories of software and/or data: an operating system 1352, I/O Device Drivers 1358, data 1356 and application programs 1354. FIG. 11 illustrates that the data 1356 can include patient NMR spectra data 1326.

As will be appreciated by those of skill in the art, the operating system 1352 may be any operating system suitable for use with a data processing system, such as IBM®, OS/2®, AIX® or zOS® operating systems or Microsoft® Windows-based operating systems (e.g., Windows XP, Windows NT, Windows 10, Windows Server 2016) or Unix or Linux™ IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. Virtualized platforms supporting one or more operating systems may also be used (i.e., VMWARE). The input/output device drivers 1358 typically include software routines accessed through the operating system 1352 by the application programs 1354 to communicate with devices such as the input/output circuits 1346 and certain memory 1336 components. The application programs 1354 are illustrative of the programs that implement the various features of the circuits and modules according to some embodiments of the present invention. Finally, the data 1356 represents the static and dynamic data used by the application programs 1354 the operating system 1352 the input/output device drivers 1358 and other software programs that may reside in the memory 1336.

While the present invention is illustrated in FIG. 11 with reference to the application programs 1354 with Modules 1124 and 1327, as will be appreciated by those of skill in the art, other configurations fall within the scope of the present invention. For example, rather than being application programs 1354 these circuits and modules may also be incorporated into the operating system 1352 or other such logical division of the data processing system. Furthermore, while the application program(s) 1354 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated but may be provided by other arrangements and/or divisions of functions between data processing systems. For example, although FIG. 11 is illustrated as having various modules, one or more of these modules may be combined or separated without departing from the scope of the present invention.

Although FIG. 11 illustrates exemplary hardware/software architectures that may be used, it will be understood that the present invention is not limited to such a configuration but is intended to encompass any configuration capable of carrying out operations described herein. Moreover, the functionality of the data processing systems and the hardware/software architectures may be implemented as a single processor system, a multi-processor system, or even a network of stand-alone computer systems, in accordance with various embodiments of the present invention.

Computer program code for carrying out operations of data processing systems discussed above with respect to the figures may be written in a high-level programming language, such as PYTHON, Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

The present invention is described herein with reference to flowchart and/or block diagram illustrations of methods, systems, and computer program products in accordance with exemplary embodiments of the invention. These flowchart and/or block diagrams further illustrate exemplary operations for administering and/or providing calendar-based time limited passcodes, in accordance with some embodiments of the present invention. It will be understood that each block of the flowchart and/or block diagram illustrations, and combinations of blocks in the flowchart and/or block diagram illustrations, may be implemented by computer program instructions and/or hardware operations. These computer program instructions may be provided to a processor of a general purpose computer, a special purpose computer, or other programmable data processing apparatus to produce a machine, such that the instructions, which execute via the processor of the computer or other programmable data processing apparatus, create means and/or circuits for implementing the functions specified in the flowchart and/or block diagram block or blocks.

These computer program instructions may also be stored in a computer usable or computer-readable non-transient memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

The flowcharts and block diagrams illustrate the architecture, functionality, and operations of some embodiments of methods, systems, and computer program products. In this regard, each block represents a module, segment, or portion of code, which comprises one or more executable instructions for implementing the specified logical function(s). It should also be noted that in other implementations, the function(s) noted in the blocks might occur out of the order noted. For example, two blocks shown in succession may, in fact, be executed substantially concurrently or the blocks may sometimes be executed in the reverse order, depending on the functionality involved.

The present invention may be embodied as systems, methods, and/or computer program products. Accordingly, the present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any non-transient medium that can contain, store, communicate, propagate, or transport the program for use by or in connection with the instruction execution system, apparatus, or device.

The computer-usable or computer-readable medium may be, for example, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Furthermore, the user's computer, a remote computer (i.e., server) or both, may be integrated into or communicate with other systems, such as control cabinets of MRI scanner systems, hospital PACS (picture archiving and communication system) and/or clinician workstations, for example.

Non-Limiting Examples will be discussed below.

EXAMPLES

Example 1

Subject Recruitment

This study was approved by the Duke University Institutional Review Board, and written informed consent was provided by all subjects prior to participation. Dynamic $^{129}$Xe spectra were acquired in 8 healthy volunteers (7 males and 1 female; 26.4±4.9 years old) and 9 subjects with IPF (7 males and 2 females; 66.1±5.6 years old). Healthy volunteers had no known pulmonary disorders, no cardiac arrhythmias, and no history of smoking. Subjects with IPF were diagnosed according to ATS criteria, confirming a UIP pattern on CT or from surgical lung biopsy. See Raghu et al. An official ATS/ERS/JRS/ALAT statement: idiopathic pulmonary fibrosis: evidence-based guidelines for diagnosis and management. *American journal of respiratory and critical care medicine.* 2011; 183(6):788-824.

Xenon Polarization and Delivery

Using a commercially available polarizer (Model 9810, Polarean, Inc, Durham, N.C., USA), 300 mL of isotopically enriched $^{129}$Xe (85%) was hyperpolarized to approximately 20% via rubidium vapor spin-exchange optical pumping. Hyperpolarized $^{129}$Xe was cryogenically accumulated and thawed into 1 L Tedlar bag (Jensen Inert Products, Coral Springs, FL). This provided a 51-mL dose equivalent (the product of polarization, enrichment and xenon volume) of hyperpolarized $^{129}$Xe. See He et al. Dose and pulse sequence considerations for hyperpolarized $^{129}$Xe ventilation MRI. *Magnetic resonance imaging.* 2015; 33(7):877-885; the contents of which is hereby incorporated by reference as if recited in full herein. The bag volume was expanded to 1 L using ultra-high-purity $N_2$.

After two preparatory breaths, subjects inhaled $^{129}$Xe from functional residual capacity (FRC), then held their breath for 8 seconds, and then slowly exhaled. See Kaushik et al. Measuring diffusion limitation with a perfusion-limited gas-hyperpolarized $^{129}$Xe gas-transfer spectroscopy in patients with idiopathic pulmonary fibrosis. *Journal of Applied Physiology.* 2014; 117(6):577-585; the contents of which is hereby incorporated by reference as if recited in full herein. Data acquisition began during inhalation before the subject began their breath hold. During MRI, each subject's heart rate and oxygen saturation were monitored using an MR-compatible monitoring system (Expression Model 865214; Invivo Corporation, Orlando, FL).

$^{129}$Xe Spectroscopy

Dissolved-phase spectra were acquired using a 1.5 T GE scanner running the 15M4 EXCITE platform (GE Healthcare, Waukesha, WI). Subjects were fitted with a quadrature vest coil (Clinical MR Solutions, Brookfield, WI) tuned to 17.66 MHz. Spectra were acquired with the transmit frequency tuned to selectively excite the dissolved-phase $^{129}$Xe using a 1.2 ms 2-lobe sinc pulse, applied at a frequency 3,832 Hz (217 ppm) above the gas-phase. Over the course of the 16 second breathing maneuver, 802 free induction decays (FIDs) were acquired with 512 samples per FID, echo time (TE)=0.932 ms, repetition time (TR)=20 ms, dwell time per point=32 μs, flip angle≈20°.

However, it is contemplated that the temporal resolution may be diminished from 20 ms to about 300 ms. Assuming that the highest heart rate likely to me encountered is 100 beats per minute (BPM), samples would need to be taken at twice this frequency or 3.33 Hz to meet Nyquist criterion. This means that signals can be acquired about every 300 ms. Reducing the temporal resolution (increasing TR) may provide several advantages. For example, spectral resolution can be increased by sampling the FID for a longer period (increasing the sampling rate). With a reduced temporal resolution, there is the opportunity to reduce the bandwidth (or increase the dwell time) which will increase SNR.

Also, or alternatively, the spectra can be acquired with a larger flip angle (i.e., about 90 degrees vs about 20 degrees). This can enhance signal to noise ratio and result in more faithful spectral analysis. Also, by using 90 degree pulses all the dissolved phase magnetization will be destroyed after each read-out. Thus, the signals will be sensitive to freshly diffused magnetization and will likely enhance sensitivity to delayed oxygenation in interstitial lung disease.

Spectroscopic Processing

Prior to fitting the spectra, two filtering steps were applied to improve spectral SNR while minimizing the need to sacrifice the temporal resolution that was needed to capture the cardiopulmonary dynamics. First, the raw FIDs were processed using the Spectral Improvement by Fourier Thresholding (SIFT) method. This involves Fourier transforming the raw data along the indirect time dimension (time with respect to the breath hold) and retaining only the coefficients that exceed a predetermined threshold. The data are then Fourier transformed back along the indirect frequency dimension to undergo spectral curve fitting. This preprocessing thus filters the non-dominant frequencies out of the indirect time dimension to smooth temporal changes between FIDS, while leaving the spectral-frequency domain intact. The time-domain SIFT-filtered FIDS were then averaged using a 5 FID sliding boxcar window filter and subsequently underwent complex fitting in the time domain, using a custom MATLAB toolkit. See Robertson et al. Uncovering a third dissolved-phase $^{129}$Xe resonance in the human lung: Quantifying spectroscopic features in healthy subjects and patients with idiopathic pulmonary fibrosis. *Magnetic resonance in medicine.* 2017; 78(4):1306-1315; the contents of which is hereby incorporated by reference as if recited in full herein.

Although much prior literature has treated the dissolved phase $^{129}$Xe spectra as consisting of two simple Lorentzian RBC and barrier resonances, recent work has shown that the barrier resonance is more structured. See Robertson et al. Uncovering a third dissolved-phase 129Xe resonance in the human lung: Quantifying spectroscopic features in healthy subjects and patients with idiopathic pulmonary fibrosis. *Magnetic resonance in medicine.* 2017; 78(4):1306-1315; the contents of which is hereby incorporated by reference as if recited in full herein. This was addressed by Robertson et al. by allowing the barrier to consist of two independent resonances. However, this requires fitting with 4 additional degrees of freedom, which the SNR and spectral resolution of dynamically acquired data did not support. This was evidenced by the approach returning ill-conditioned fits for dynamically acquired spectra. Instead, to allow for the extra, non-Lorentzian structure of the barrier resonance, it was fit to a Voigt model. This lineshape represents the convolution of a Lorentzian peak with a Gaussian distribution and requires only one additional fitting degree of freedom. Specifically, it returns 2 distinct linewidth parameters—the Lorentzian linewidth (FWHM) and Gaussian linewidth (FWHM). See, Marshall I, Higinbotham J, Bruce S, Freise A. Use of voigt lineshape for quantification of in vivo1H spectra. *Magnetic resonance in medicine.* 1997; 37(5):651-657, the contents of which are hereby incorporated by reference as if recited in full herein.

The overall fitted signal can be calculated using Equation 1. Each resonance is characterized by 4 spectral parameters: amplitude ($\alpha$), frequency ($f$), phase ($\varphi$), and Lorentzian linewidth. For the barrier resonance, a $5^{th}$ parameter, the Gaussian linewidth (FWHM$_G$), was also extracted. Fitting of the barrier resonance was initialized with equal Lorentzian and Gaussian linewidths.

$$S_{fit} = a_{rbc} e^{i\varphi_{rbc} + 2\pi i f_{rbc} t} e^{-\pi t \times FWHM_{rbc}} +$$
$$a_{bar} e^{i\varphi_{bar} + 2\pi i f_{bar} t} e^{-\pi t \times FWHM_{bar}} e^{-4\ln 2 \times t^2 FWHM_{G,bar}^2} +$$
$$a_{gas} e^{i\varphi_{gas} + 2\pi i f_{gas} t} e^{-\pi t \times FWHM_{gas}}$$

EQN(1)

All frequencies (Hz) were reported as chemical shifts (in ppm) above the frequency of the gaseous $^{129}$Xe resonance.

Normalizing and Quantifying Cardiogenic Spectroscopic Changes in the RBC Resonance Although numerous quantitative parameters can be analyzed and extracted from the 3 resonances during the 3 periods of the breathing maneuver, we focused specifically on characterizing temporal variations in $^{129}$Xe RBC resonance occurring at the cardiac frequency (~1 Hz). To extract these parameters, the amplitude of the RBC peak was first corrected for magnetization decays caused by T1, and RF-induced depolarization during the breath-hold. These were incorporated into an apparent T1 decay constant T1$_{app}$ that was quantified by fitting the RBC amplitude within the breath-hold period to $Ae^{-t/T1_{app}}$. The mean T1$_{app}$ for all subjects was 13.6±2.7 s. This was then used to correct the RBC signal and the remaining temporal changes in signal amplitude were expressed as a percentage change from baseline. Each of the RBC spectral parameters were further high-pass filtered with 0.5 Hz cutoff frequency to remove any residual baseline variation. The corrected and filtered parameter plots were then fit to a sinusoid with phase offset:

$$\tfrac{1}{2} A_{pk-pk} \sin(2\pi f_c t + \varphi),$$

EQN(5)

where $A_{pk-pk}$ is the peak-to-peak amplitude, $f_c$ is the cardiac frequency, t is time in seconds, and $\varphi$ is a phase off-set. The cardiac frequency $f_c$ was derived from each subject's RBC amplitude oscillations and was used in the temporal fits of all other RBC spectral parameters (chemical shift, linewidth, and phase).

Statistical Analysis

Statistical analysis was performed in MATLAB. A Mann-Whitney-Wilcox U-test was used to determine if the differences between healthy normal and IPF subjects were statistically significant (P<0.05).

Example 1 Results

For each subject, the age, sex, pulmonary function test results, and the magnitude of the oscillations in the RBC spectral parameters are summarized in Table 1 (FIG. 14).

Quantifying Static Spectral Parameters

Figure 12A:
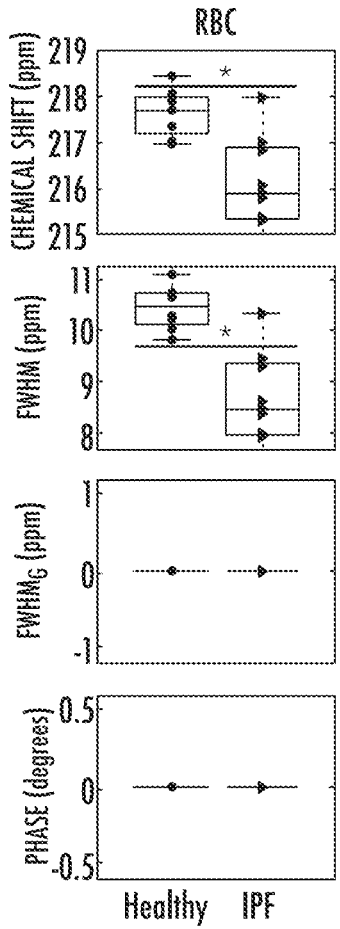
FIGS. 12A-12D are plots of comparisons of static parameters for healthy and IPF subjects during a first second of a breath-hold with RBC phase set to zero degrees according to embodiments of the present invention.
Figure 12B:
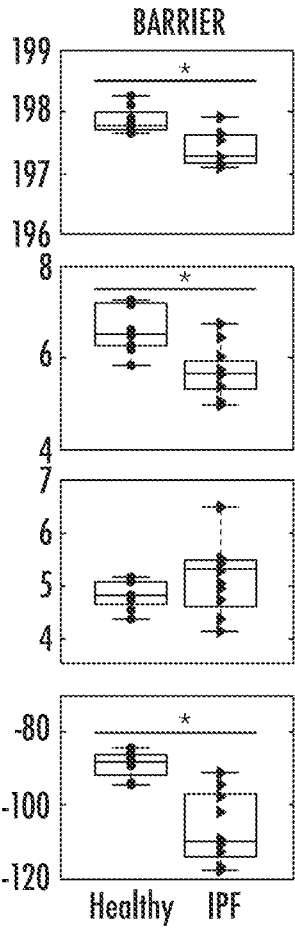
Figure 12C:
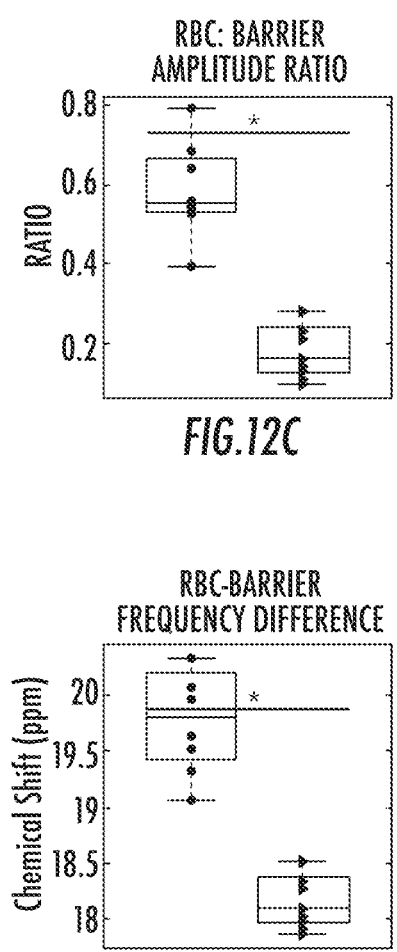
Figure 12D:
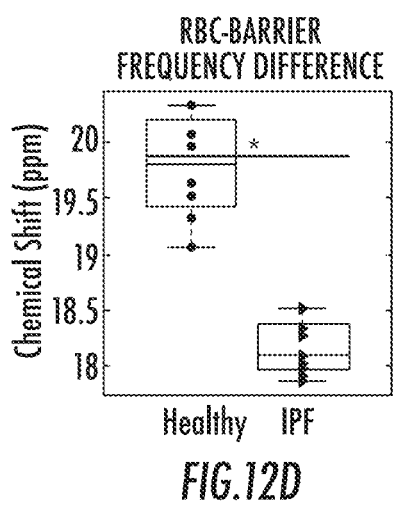

Prior to analyzing the $^{129}$Xe spectral dynamics, the static parameters, averaged over the first second of the breath-hold, were determined. The resulting RBC and barrier fit parameters, as well as relevant derived ratios, are compared between the healthy and IPF cohorts in FIGS. 12A-12D. The mean RBC:Barrier amplitude ratio (FIG. 12C) for healthy volunteers was 0.58±0.12, which was significantly reduced in IPF patients to 0.18±0.07 (P<0.001). The RBC frequency (FIG. 12A) was 1.5 ppm lower in the IPF cohort (P=0.004) and its Lorentzian line width was 1.7 ppm narrower (P=0.001). The barrier frequency (FIG. 12B) was also 0.5 ppm lower in IPF (P=0.0025), and the Lorentzian component of its linewidth 0.9 ppm smaller (P=0.006); the Gaussian linewidth did not differ from the healthy cohort (P=0.2). These differences contributed to the phase difference between barrier FIG. 12B and RBC (FIG. 12A) resonances being 17.0° smaller compared to the healthy cohort (P=0.006).

$^{129}$Xe Spectral Changes Over the Course of the Breathing Maneuver

The spectral dynamics of all three $^{129}$Xe resonances are displayed for a representative healthy volunteer (subject 6) in FIG. 1. The breathing maneuver is reflected in each of the fit parameters, readily demarking the inhalation, breath-hold, and exhalation periods. As the subject exhales, the gas resonance frequency shifts negatively by 0.11 ppm and its linewidth broadens by 0.1 ppm. In contrast, exhalation causes the barrier resonance to shift positively by 0.06 ppm and its Lorentzian linewidth to narrow by 0.29 ppm. The RBC resonance appears to be influenced by both inhalation and exhalation, primarily in its linewidth, which, like the barrier, narrows slightly (0.37 ppm) during exhalation. The RBC amplitude also exhibits a prominent periodicity at a frequency of 58 cycles per minute, which is consistent with the subject's heart rate, recorded by pulse oximetry immediately prior to and after the acquisition (61 and 65 bpm, respectively). These dynamics are also present, although more faintly, at the same frequency in the RBC chemical shift and phase.

FIG. 2 displays the same spectral dynamics, plotted for a subject with IPF (subject 13). Like in the healthy volunteer, the gas-phase parameters reflect both the inhale and exhale dynamics, which are also clearly seen in the barrier resonance through an increasing chemical shift but narrowing of both linewidth parameters upon exhalation. The RBC resonance subtly shows the inhalation, while exhalation is well demarked by its increasing chemical shift and Lorentzian linewidth, coupled with decreasing phase. In this IPF patient, the RBC amplitude is also periodic at a frequency near subject's heart rate pre- and post-scan (71 cycles per minute compared to 70 and 72 bpm, respectively). Interestingly, this cardiac periodicity is also prominent in both the RBC chemical shift and phase.

Figure 13:
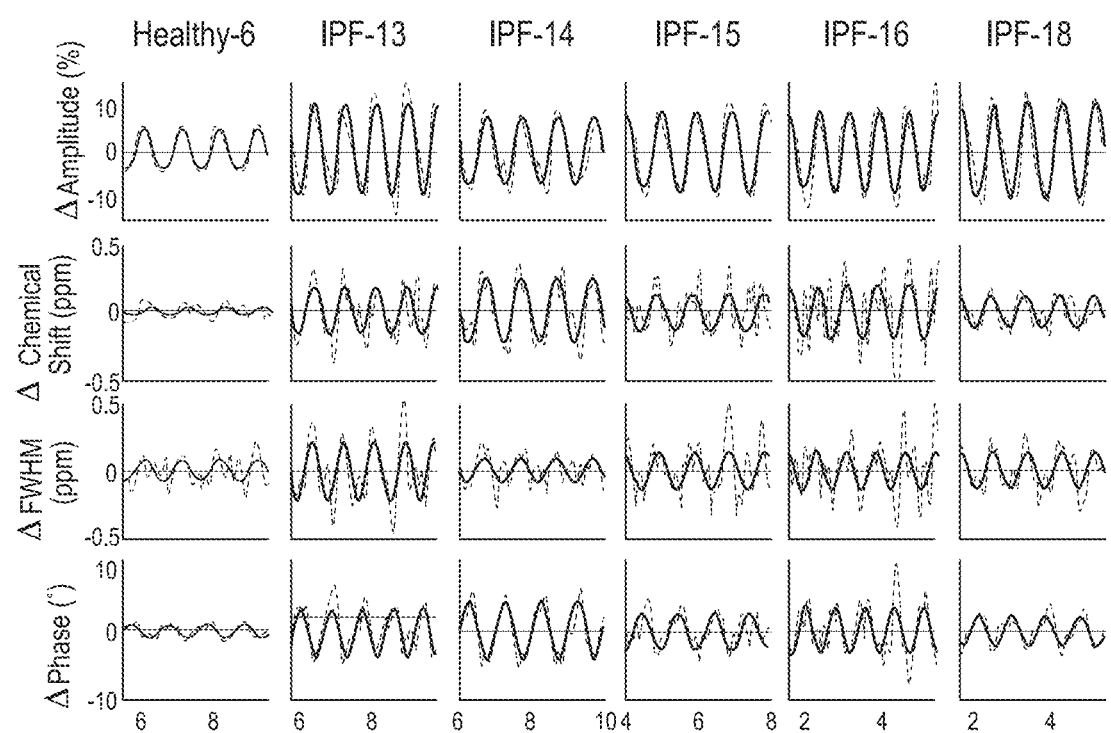
FIG. 13 are normalized and detrended RBC spectral parameter dynamics during a breath hold from a representative healthy volunteer (left side panels) and 5 subjects with IPF according to embodiments of the present invention. The solid line represents a sinusoidal fit.

These cardiac dynamics affecting the RBC spectral parameters are better appreciated in the normalized and detrended plots as shown for a representative healthy volunteer and several IPF patients in FIG. 13. In the healthy volunteer, the RBC amplitude varied peak-to-peak (pk-pk) at 9.1%, while oscillations in the RBC chemical shift and phase remained below 0.05 ppm and 1.5° respectively. By contrast, the first subject with IPF (IPF-13) not only exhibited more than 2-folder larger RBC amplitude variations (19.9% pk-pk), but also exhibited oscillations in RBC chemical shift that were nearly 6-fold larger at 0.29 ppm, while phase varied nearly 4-fold more at 5.80. Such oscillations in RBC amplitude, frequency and phase were also notable in the other IPF subjects depicted.

Amplitude of Oscillations Varies Between IPF and Healthy Subjects

The magnitude of the cardiogenic oscillations in the RBC spectral parameters are compared between healthy volunteers and IPF patients in FIG. 4. In the IPF versus healthy cohort, RBC amplitude variations were nearly twice as high (16.8±5.2% vs 9.7±2.9%; P=0.008), chemical shift oscillations were more than 5-fold higher (0.43±0.33 ppm vs 0.083±0.05 ppm; P<0.001), and RBC phase oscillations were more than 5-fold higher (7.7±5.6° vs 1.4±0.8°; P<0.001). Only the RBC linewidth was not statistically different between the two cohorts (0.3±0.2 ppm vs 0.2±0.1 ppm, P=0.1).

Discussion

Benefits of Using a Barrier Voigt

The Voigt lineshape model was found to more robustly fit the $^{129}$Xe-barrier resonance dynamics than the "3-Lorentzian" fit (one RBC, two barrier). Although, the 3-Lorentzian model returns a lower residual error than barrier Voigt when fitting high-resolution, high SNR spectra[8], it is not well suited for the lower SNR and spectral resolution present in the dynamic $^{129}$Xe acquisition. See Robertson et al. Uncovering a third dissolved-phase 129Xe resonance in the human lung: Quantifying spectroscopic features in healthy subjects and patients with idiopathic pulmonary fibrosis. *Magnetic resonance in medicine.* 2017; 78(4):1306-1315. This is evidenced by highly variable fits for the two barrier resonances seen in FIG. 6B. By contrast, the barrier Voigt model was able to capture the additional structure of the barrier resonance, while remaining stable over the course of the acquisition. This is likely attributable to it requiring only one additional degree of freedom rather than the four required to fit the barrier to two Lorentzian resonances. Moreover, the 2-component dissolved-phase fitting of RBCs to a Lorentzian and barrier to a Voigt model leaves intact the current 3-compartment model of gas-exchange that forms the basis of gas exchange imaging methods and CSSR analysis. See Chang, Y V MOXE: a model of gas exchange for hyperpolarized $^{129}$Xe magnetic resonance of the lung. *Magnetic resonance in medicine.* 2013; 69(3):884-890.

Importantly, comparing the fits of a large average of data found the barrier Voigt model to return similar RBC parameters as the 3-Lorentzian fit. The barrier Voigt model returned an RBC:Barrier ratio of 0.59±0.11 for healthy volunteers that is reasonably consistent with previous 2- and 3-peak Lorentzian fitting of the dissolved resonances which are 0.55±0.13 and 0.44±0.07 respectively, and correctly captures the striking reduction in this ratio in subjects with IPF. See Kaushik et al., Measuring diffusion limitation with a perfusion-limited gas—hyperpolarized 129Xe gas-transfer spectroscopy in patients with idiopathic pulmonary fibrosis. *Journal of Applied Physiology.* 2014; 117(6):577-585; Robertson et al. Uncovering a third dissolved-phase 129Xe resonance in the human lung: Quantifying spectroscopic features in healthy subjects and patients with idiopathic pulmonary fibrosis. *Magnetic resonance in medicine.* 2017; 78(4):1306-1315.

Origins of Temporal Dynamics

The temporal changes in the $^{129}$Xe spectra directly report on the physiological dynamics of gas exchange in the lung and pulmonary capillaries. It is striking to find that nearly all the spectral parameters reflect dynamics associated with the breathing maneuver. This is particularly well defined during exhalation, which is accompanied by an increasing gas-phase linewidth, combined with a corresponding narrowing of both dissolved-phase peaks. This narrowing, which is inversely related to the apparent transverse relaxation time, $T_2^g$, could suggest improving local field inhomogeneity, which, in the lung, is dominated by the bulk susceptibility difference of $\Delta\chi \approx 9$ ppm between air and tissue[22]. See Chen et al. Spatially resolved measurements of hyperpolarized gas properties in the lung in vivo. Part I: diffusion coefficient. *Magnetic resonance in medicine.* 1999; 42(4):721-728. During exhalation, the passive compression of the lung moves air out of the alveolar sacs and reduces aggregate alveolar volume. See Hajari et al. Morphometric changes in the human pulmonary acinus during inflation. *Journal of Applied Physiology.* 2012; 112(6):937-943. This, in turn, increases the volume fraction of tissue relative to air while mean capillary diameter increases along with the average alveolar wall thickness. See Glazier et al. Measurements of capillary dimensions and blood volume in rapidly frozen lungs. *Journal of Applied Physiology.* 1969; 26(1):65-76; Tsunoda et al. Lung volume, thickness of alveolar walls, and microscopic anisotropy of expansion. *Respiration physiology.* 1974; 22(3):285-296. Thus, during exhalation, fewer dissolved-phase xenon atoms reside near the air-tissue boundaries causing RBC and barrier linewidths to narrow. By contrast, gas-phase xenon atoms are now more likely to reside near a tissue interface, and therefore the gas-phase linewidth increases.

The high-frequency dynamics of $^{129}$Xe-RBC transfer provide an intriguing window on how the cardiac cycle affects gas exchange. The RBC signal in these acquisitions arises predominantly from $^{129}$Xe nuclei interacting with RBCs in the pulmonary capillary bed. This strong localization stems from using a relatively large flip angle (~20°), combined with a repetition time that is short (TR=20 ms) in relation to the RBC transit time (~750 ms). Thus, the magnetization of $^{129}$Xe atoms in the dissolved phase is quickly destroyed by RF pulses and can only be replenished through continued diffusive gas transfer from the airspaces[26]. However, once $^{129}$Xe atoms move to larger vessels beyond the gas exchange units, such replenishment no longer occurs, and any residual magnetization is quickly destroyed by RF pulsing. Therefore, the fluctuations detected in the RBC resonance provide evidence that $^{129}$Xe-RBC transfer at the alveolar-capillary interface is temporally dependent on capillary pressure and blood volume oscillations driven by the cardiac cycle.

The oscillations in the RBC signal amplitude reflect a cyclic change in the number of polarized $^{129}$Xe atoms interacting with the RBCs over the course of the cardiac cycle. This observation is likely caused by cardiogenic fluctuations in capillary blood volume. The pulmonary capillaries experience slightly elevated blood pressure at systole, with a concomitant decrease at diastole. See Rossvoll et al. Pulmonary venous flow velocities recorded by transthoracic Doppler ultrasound: relation to left ventricular diastolic pressures. *Journal of the American College of Cardiology.* 1993; 21(7):1687-1696. Such pressure changes likely affect capillary blood volume, as recently demonstrated by synchrotron imaging over the course of a respiratory cycle. See Porra et al. Synchrotron Imaging Shows Effect of Ventilator Settings on Intra-breath Cyclic Changes in Pulmonary Blood Volume. *American Journal of Respiratory Cell and Molecular Biology.* 2017(ja). Here, the relative RBC amplitude fluctuations were found to be nearly two-fold larger in subjects with IPF, suggesting that in these patients, the relative change in capillary blood volume over the cardiac cycle is larger than in healthy volunteers. This is likely the result of these patients having significant regions of capillary destruction where RBC transfer is absent. See Wang et al. Using hyperpolarized $^{129}$Xe MRI to quantify regional gas transfer in idiopathic pulmonary fibrosis. *Thorax.* 2017:thoraxjnl-2017-210070; the contents of which is hereby incorporated by reference as if recited in full herein. Thus, the additional capillary blood volume at systole is distributed to a relatively smaller effective capillary volume.

The observation of cardiogenic oscillations in the RBC chemical shift in patients with IPF is particularly intriguing given that in vitro studies have shown that the RBC frequency depends non-linearly on blood oxygenation level, $sO_2$. See Norquay et al. $^{129}$Xe chemical shift in human blood and pulmonary blood oxygenation measurement in humans using hyperpolarized 129Xe NMR. *Magnetic resonance in medicine.* 2017; 77(4):1399-1408; Wolber et al. Hyperpolarized 129Xe NMR as a probe for blood oxygenation. *Magnetic resonance in medicine.* 2000; 43(4):491-496. Over the physiologically relevant range of $sO_2$=0.6-0.98, the RBC chemical shift increases sigmoidally by more than 4 ppm. This would suggest that the observed pulsations in the RBC chemical shift of 0.43 ppm reflect global $sO_2$ changes of order 0.07 in the pulmonary capillaries, assuming a maximum $sO_2$ of 0.95. The fact that RBC frequency pulsations are seen in IPF, but not healthy subjects suggests this is a potentially unique signature of retarded diffusive transfer of oxygen across the alveolar-capillary barrier. That is, as deoxygenated blood enters the capillary beds at systole, it is slower to oxygenate in patients with significant interstitial thickening. In a healthy normal volunteer, capillary RBCs reach full oxygenation in about 250 ms, or a third of the total capillary transit time. See West et al. *Respiratory physiology: the essentials.* Lippincott Williams & Wilkins; 2012. Thus, in healthy volunteers the average $sO_2$ in RBCs experienced by $^{129}$Xe is skewed towards full oxygenation. In contrast, the thicker interstitial barrier tissues present in patients with IPF slow the diffusion of gases and consequently, $sO_2$ levels in the pulmonary capillary beds are more broadly distributed. Hence, while a healthy volunteer and subject with IPF may have the same distal $O_2$ saturation level, $^{129}$Xe spectroscopy detects differences in the capillary $sO_2$ variation by probing the alveolar-capillary interface.

From a technical perspective, the cardiac pulsations are even more prominent in the phase of the $^{129}$Xe-RBC resonance. This metric, which is linearly related to chemical shift, provides a relatively clean signal that may prove to be more robust. The observation of pulsations in $^{129}$Xe RBC frequency and phase may eventually prove to help differentiate the causes of dyspnea attributable to interstitial disease from other causes of gas exchange impairment such as pulmonary vascular disease. See Dahhan et al. Abnormalities in hyperpolarized $^{129}$Xe magnetic resonance imaging and spectroscopy in two patients with pulmonary vascular disease. *Pulmonary circulation.* 2016; 6(1):126-131; the contents of which is hereby incorporated by reference as if recited in full herein Example 1 Conclusion In this study, a method of acquiring, processing and analyzing $^{129}$Xe spectra over a simple 16 second spectroscopic acquisition and breathing maneuver was successfully identified that yielded a series of novel parameters which can be used to further characterize gas exchange. The collected FIDs were fit to a Lorentzian for the RBC and gas resonances and a Voigt lineshape for the barrier resonance. This accommodated the additional structure of the barrier resonance, while limiting the degrees of freedom such that the fitting algorithm converged even for the lower SNR and spectral resolution of dynamic acquisitions. Spectroscopic fit parameters for each $^{129}$Xe resonance were determined with 20 ms temporal resolution. Analysis of the static spectral parameters found features differentiating the IPF and healthy cohorts that were largely consistent with previous studies. Their dynamics showed all three resonances to be sensitive to the breathing maneuver, with distinct changes in the RBC and gas linewidths. Most notably, the RBC amplitude, chemical shift, and phase were found to oscillate at the cardiac frequency. These oscillations were significantly larger in patients with IPF than in healthy controls. Thus, careful analysis of one or both static and dynamic $^{129}$Xe spectra can potentially provide a wide array of additional information that can help further discern the different underlying causes of gas exchange impairment.

Example 2

As an increasing number of patients exhibit concomitant cardiac and pulmonary disease, limitations of standard diagnostic criteria are more frequently encountered. In this Example 2, noninvasive $^{129}$Xenon MR imaging and spectroscopy are used to identify patterns of regional gas transfer impairment and hemodynamics that are uniquely associated with chronic obstructive pulmonary disease (COPD), idiopathic pulmonary fibrosis (IPF), left heart failure (LHF), and pulmonary arterial hypertension (PAH).

While $^{129}$Xe imaging provides useful quantification of regional functional burden, it is believed that a more detailed characterization of whole-lung $^{129}$Xe spectroscopic indices provide additional metrics that may help to further discriminate the underlying pathologies. This array of non-invasive imaging and spectroscopic markers of pulmonary gas transfer and hemodynamics derived from hyperpolarized $^{129}$Xe can provide a comprehensive and non-invasive phenotyping of cardiopulmonary physiology in individual patients.

In this Example 2, a comprehensive panel of non-invasive $^{129}$Xe MR imaging and spectroscopy is applied to a cohort of patients with known heart and lung disease in order to identify features that could differentiate signatures of COPD, IPF, left heart failure (LHF), or pulmonary arterial hypertension (PAH). Hyperpolarized $^{129}$Xe freely diffuses from airspace to interstitial barrier tissues to RBCs. In these compartments, the $^{129}$Xe atom exhibits distinct frequency shifts of 0 ppm, 198 ppm, and 217 ppm, respectively. These properties can be exploited to allow 3D imaging and quantification of $^{129}$Xe distribution in airspace (ventilation), its barrier uptake and RBC transfer to generate maps. These maps can be color coded to represent different signal intensity levels with the central (green) bins representing voxels in the normal reference range. $^{129}$Xe spectra can be acquired dynamically, such as about every 20 ms, revealing cardiogenic oscillations of RBC amplitude (%) and frequency shift (ppm).

In this Example 2, healthy volunteers (n=23) and patients with COPD (n=8), IPF (n=12), LHF (n=6), and PAH (n=10) underwent $^{129}$Xe gas transfer imaging and dynamic spectroscopy. For each patient, 3D maps were generated to depict ventilation, barrier uptake, and red blood cell (RBC) transfer. Dynamic $^{129}$Xe spectroscopy was used to quantify cardiogenic oscillations in the RBC signal amplitude and frequency shift.

Compared to healthy volunteers, all patient groups exhibited decreased ventilation and RBC transfer (p≤0.01, p≤0.01). Patients with COPD demonstrated more ventilation and barrier defects compared to all other groups (p≤0.02, p≤0.02). In contrast, IPF patients demonstrated elevated barrier uptake compared to all other groups (p≤0.007) and increased RBC amplitude and shift oscillations compared to healthy volunteers (p=0.007, p≤0.01). Patients with COPD and PAH both exhibited decreased RBC amplitude oscillations (p=0.02, p=0.005) compared to healthy volunteers. LHF was distinguishable from PAH by enhanced RBC amplitude oscillations (p=0.01).

COPD, IPF, LHF, and PAH each exhibit unique $^{129}$Xe MR imaging and dynamic spectroscopy "signatures". Each of the signatures can be described as a unique metric or graphic marker of a combination of different $^{129}$Xe imaging and $^{129}$Xe spectroscopy parameters, typically at least two of each, shown as using six such parameters. These metrics may help with diagnostic challenges in cardiopulmonary disease and increase understanding of regional lung function and hemodynamics at the alveolar-capillary level.

FIG. 15 provides a table of Demographic and Clinical Characteristics stratified by Condition: IPF=idiopathic pulmonary fibrosis; COPD=chronic obstructive pulmonary disease; PAH=pulmonary arterial hypertension; 6MWD=6-minute walk distance; PFT=pulmonary function test; PCWP=pulmonary capillary wedge pressure; PVR=pulmonary vascular resistance; RVSP=right ventricular systolic pressure. Continuous variables presented as median (IQR); categorical variables presented as frequency (proportion)

Subject Recruitment

The protocol was approved by the Institutional Review Board of Duke University Medical Center. Healthy volunteers, and patients with either COPD, IPF, LHF, or PAH were recruited, and all provided written, informed consent. All healthy volunteers had no smoking history or known respiratory conditions. COPD was diagnosed using spirometry with a post-bronchodilator forced expiratory volume in one second (FEV$_1$)/forced vital capacity (FVC)≤70% predicted. See Celli et al., *Standards for the diagnosis and treatment of patients with COPD: a summary of the ATS/ERS position paper.* Eur Respir J, 2004. 23(6): p. 932-46. The diagnosis of IPF was established according to ATS/ERS criteria, either from a confirmed pattern of usual interstitial pneumonia (UIP) pattern on CT or from surgical lung biopsy. See Raghu et al., *An official ATS/ERS/JRS/ALAT statement: idiopathic pulmonary fibrosis: evidence-based guidelines for diagnosis and management.* Am J Respir Crit Care Med, 2011. 183(6): p. 788-824. LHF was confirmed by echocardiogram. See Lang, *Recommendations for Cardiac Chamber Quantification by Echocardiography in Adults: An Update from the American Society of Echocardiography and the European Association of Cardiovascular Imaging* (vol 28, pg 1, 2015). Journal of the American Society of Echocardiography, 2016. 29(6): p. 521-521. PAH was defined according to the World Health Organization criteria and diagnosed by right heart catheterization with a resting mean pulmonary arterial pressure (mPAP)≥25 mmHg and a pulmonary capillary wedge pressure (PCWP)≤15 mmHg. See Simonneau, et al., *Updated Clinical Classification of Pulmonary Hypertension.* Journal of the American College of Cardiology, 2009. 54(1): p. S43-S54. All clinical tests were performed as a part of routine care. Pulmonary function tests (PFTs) were performed on all patients and 83% of healthy volunteers to assess baseline pulmonary function.

MRI Acquisition $^{129}$Xe imaging and spectroscopy were acquired on either a 1.5 T (GE 15M4 EXCITE) or a 3 T (SIEMENS MAGNETOM Trio) scanner. For each subject, 3D images were acquired using an interleaved radial acquisition of gas- and dissolved-phase data during a 15 second breath-hold. See Kaushik, S. S., et al., *Probing the regional distribution of pulmonary gas exchange through single-breath gas-and dissolved-phase Xe-129 MR imaging.* Journal of Applied Physiology, 2013. 115(6): p. 850-860, the contents of which are hereby incorporated by reference as if recited in full herein. Data were acquired at an echo time that allowed the two-dissolved phase compartments to be decomposed using the 1-point Dixon method. See Kaushik et al., *Single-breath clinical imaging of hyperpolarized (129)Xe in the airspaces, barrier, and red blood cells using an interleaved 3D radial 1-point Dixon acquisition.* Magn Reson Med, 2016. 75(4): p. 1434-43, the contents of which are hereby incorporated by reference as if recited in full herein. This generated 3D images of the gas, barrier, and RBC components with 2.8 mm isotropic voxels. Subjects also underwent dynamic spectroscopy during which $^{129}$Xe free induction decays (FIDs) were collected every 20 ms (TE=0.932 ms, flip angle≈20°, dwell time=32 μs, 512/1024 points) during a breath-hold. See Bier et al., *A protocol for quantifying cardiogenic oscillations in dynamic (129) Xe gas exchange spectroscopy: The effects of idiopathic pulmonary fibrosis.* NMR Biomed, 2018: p. e4029, the contents of which are hereby incorporated by reference as if recited in full herein.

Quantitative Processing and Analysis 3D images of each compartment were rendered into quantitative maps and cast into color clusters using thresholds derived from a healthy reference cohort. See Wang, Z., et al., *Quantitative analysis of hyperpolarized 129 Xe gas transfer MRI.* Med Phys, 2017. 44(6): p. 2415-2428; He, M., et al., *Using Hyperpolarized 129Xe MRI to Quantify the Pulmonary Ventilation Distribution.* Acad Radiol, 2016. 23(12): p. 1521-1531, the contents of which are hereby incorporated by reference as if recited in full herein. The resulting binning maps depict $^{129}$Xe ventilation, barrier tissue uptake, and RBC transfer. Each of these maps were quantified by calculating the percentage of the lung exhibiting signal defects and high signal. See Wang, Z., et al., *Quantitative analysis of hyperpolarized 129 Xe gas transfer MRI.* Med Phys, 2017. 44(6): p. 2415-2428, the contents of which are hereby incorporated by reference as if recited in full herein. The dynamically acquired FIDs were fit in the time domain to determine the gas, barrier, and RBC spectral parameters. See Bier, E. A., et al., *A protocol for quantifying cardiogenic oscillations in dynamic (129) Xe gas exchange spectroscopy: The effects of idiopathic pulmonary fibrosis.* NMR Biomed, 2018: p. e4029, the contents of which are hereby incorporated by reference as if recited in full herein. The time dependent RBC signal was detrended and the cardiogenic oscillations in its amplitude and frequency shift were quantified by their peak-to-peak value relative to the mean. See, again, Bier, E. A., et al., *A protocol for quantifying cardiogenic oscillations in dynamic (129) Xe gas exchange spectroscopy: The effects of idiopathic pulmonary fibrosis.* NMR Biomed, 2018: p. e4029. Imaging and spectroscopic findings were compared across all cohorts.

Statistical Methods

Imaging and spectroscopic features were compared between cohorts. All computations were performed using JMP 14 (SAS Institute Inc, Cary, N.C.). First, a one-way analysis of variance was performed using the non-parametric Kruskal-Wallis. When a significant difference was detected, the Mann Whitney U-test was further used for pairwise analysis. Statistical significance was claimed for p<0.05.

Study Cohort

This study included 23 healthy volunteers, 8 patients with COPD, 12 with IPF, 6 with LHF, and 10 with PAH. Subject demographics and PFT results are summarized in FIG. 15.

3D-isotropic images of $^{129}$Xe in the gas, barrier, and RBC compartments were acquired on 19 healthy volunteers and all patients. Dynamic spectroscopy was acquired on 13 healthy volunteers, 6 patients with COPD, 8 with IPF, 5 with LHF, and 10 with PAH. Subjects were excluded from either imaging or spectral analysis if the acquisition did not achieve adequate SNR required for reliable quantification.

Identifying Disease-Specific Imaging-Derived Metrics

Figure 16:
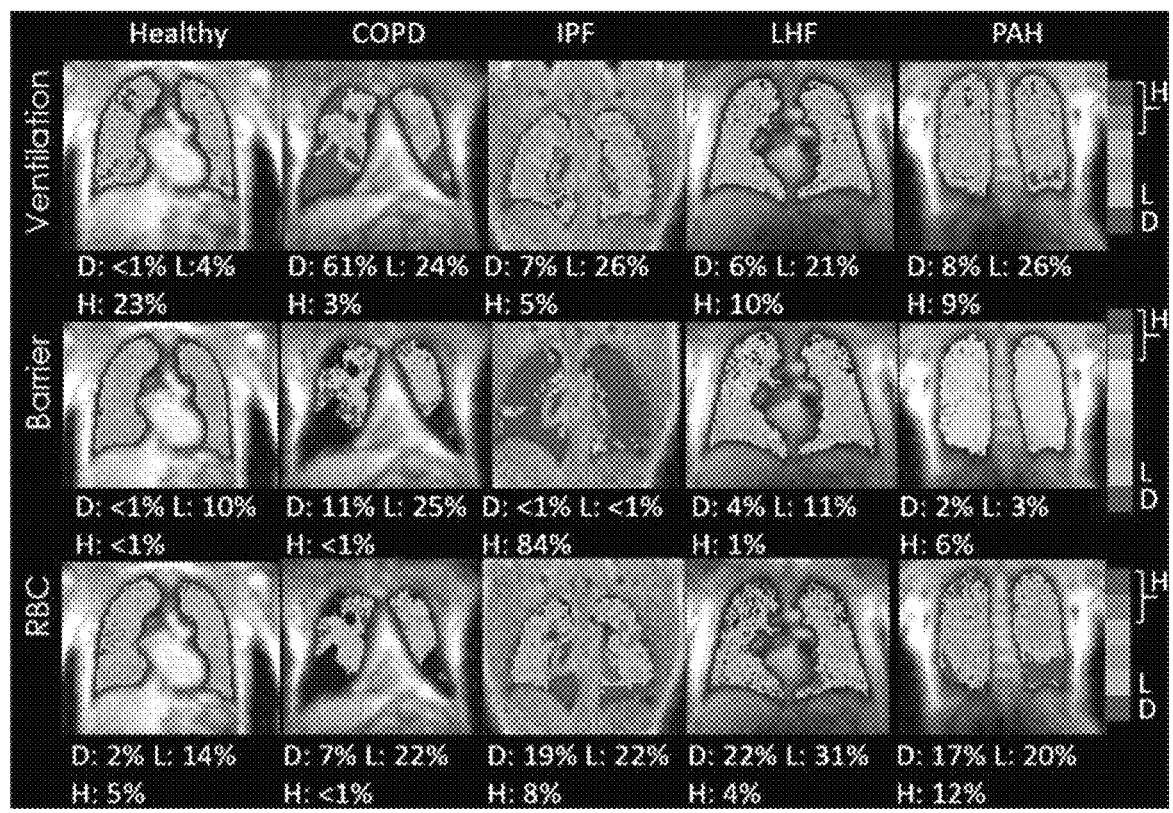
FIG. 16 is set of color-coded $^{129}$Xe MRI images (maps) for of representative subjects from each cohort (healthy, COPD, IPF, LHF and PAH), with ventilation mages top rows, barrier middle row and RBC uptake/transfer bottom row according to embodiments of the present invention.

Representative ventilation and gas transfer maps from subjects in each group are depicted in FIG. 16 along with the derived quantitative metrics. For each map, the percentages of voxels falling in the defect, low, and high bins are reported. In the healthy volunteer, the majority of the $^{129}$Xe signal in all three compartments fell within ±1 standard deviation from the mean of the reference distribution and thus, in the "normal" green color bins. In contrast, the COPD subject exhibited significant defects in all 3 compartments —ventilation, barrier, and RBC, indicated by the red color bins. The IPF subject exhibited relatively normal ventilation, but significant areas of high barrier uptake, accompanied by defects in RBC transfer in the lower lobes. Both the LHF and PAH subjects exhibited slight ventilation defects, relatively normal barrier, but more significant deficits in RBC transfer. Ventilation, barrier uptake, and RBC transfer maps of representative subjects from each cohort. The color bins represent signal intensity, with red for the lowest and blue/purple for the highest and green representing voxels in the healthy reference range. Each map is quantified by the defect (D), low (L), and high (H) percentage, calculated respectively as the voxel fraction of the lowest, second lowest, and the highest two bins for each map.

FIGS. 17A-17D evaluate these imaging features quantitatively across the cohorts, comparing the percentages of ventilation defects, RBC defects, barrier defects and high barrier. Ventilation defect (FIG. 17A), RBC defect (FIG. 17B), Barrier defect (FIG. 17C) and Barrier high percentage comparisons for all cohorts (FIG. 17D). Asterisks mask a significantly increased (red-R) or decreased (green-G) value compared to all other cohorts. Compared to healthy subjects, all disease cohorts showed increased ventilation defect ($p \leq 0.01$) and RBC defect ($p \leq 0.01$). COPD was characterized by significantly elevated percentages of ventilation defects ($p \leq 0.02$) and barrier defects ($p \leq 0.02$). IPF uniquely exhibited reduced barrier defects ($p \leq 0.02$) but elevated percentages of high barrier ($p \leq 0.007$). PAH and LHF exhibited slightly elevated ventilation defects and modestly elevated RBC defects. Compared to healthy subjects, all patient groups exhibited a larger percentage of defects in ventilation ($p \leq 0.01$ for all comparisons) and RBC transfer ($p \leq 0.01$ for all comparisons). The COPD cohort stood out for exhibiting the largest percentages of ventilation defects (41.5±22.6%, $p \leq 0.02$ for all comparisons) and was the only one to show defects in barrier uptake (10.4±7.1%, $p \leq 0.02$ for all comparisons). By contrast, IPF patients were distinguished from the other groups by the largest percentage of voxels with high $^{129}$Xe uptake in the barrier tissue (39.8%, $p \leq 0.007$ for all comparisons). IPF subjects exhibited only modest ventilation defects (11.5±6.7%, p=0.0003 vs healthy) but substantial RBC defects (11.3±6.7%, p=0.0001 vs healthy). LHF and PAH patients presented with similar imaging characteristics with mildly elevated ventilation defects (LHF: 11.7±6.2%, p=0.01 vs healthy; PAH: 8.4±4.7%, p=0.01 vs healthy) and increased RBC transfer defects (LFH: 13.3±10.2%, p=0.01 vs healthy; PAH: 14.5±9.3%, p=0.002 vs healthy).

Disease-Specific Spectroscopy-Derived Metrics

FIGS. 18A and 18B show the detrended RBC signal amplitude and shift oscillations for representative subjects from each group demonstrate cardiogenic oscillations. Notably, the RBC signal amplitudes (FIG. 18A) for each patient oscillate at a frequency identical to his/her heart rate. The IPF patient also exhibits such cardiogenic oscillations prominently in the RBC frequency shift. Both the IPF and LHF patient exhibit enhanced RBC amplitude oscillations. By contrast, RBC signal oscillations are diminished in both the PAH and COPD patients. Only the IPF patient exhibits oscillations in the RBC shift (FIG. 18B).

FIGS. 19A and 19B show the group-wise comparison of the cardiogenic RBC amplitude and shift metrics. In healthy subjects, the RBC amplitude (FIG. 19A) oscillated at a height of 10.0±2.6% peak-to-peak with very little RBC shift oscillation (0.07±0.05 ppm). The RBC shift (FIG. 19B) only oscillates significantly in the IPF cohort (0.46±0.33 ppm, $p \leq 0.01$ for all comparisons). IPF patients also exhibited larger RBC amplitude oscillations (16.7±5.5%, p=0.007) compared to healthy volunteers. RBC amplitude oscillations were diminished in both COPD and PAH compared to healthy volunteers (COPD: 5.5±4.7%, p=0.02; PAH: 6.0±3.6%, p=0.005). In subjects with LHF, the RBC amplitude oscillations were larger than in healthy volunteers, but this did not reach statistical significance (13.0±5.1%, p=0.2). However, these oscillations were significantly higher compared to subjects with PAH (p=0.01). Thus, FIGS. 19A and 19B show RBC amplitude and frequency shift oscillations, respectively, compared across cohorts. Gray (G) asterisks mark a significant difference between cohorts and red (R) asterisk marks increased value compared to all other cohorts. Compared to healthy subjects, COPD (p=0.02) and PAH (p=0.005) exhibited decreased RBC amplitude oscillations, while they were increased in IPF (p=0.007). Moreover, in LHF the RBC amplitude oscillations were significantly increased compared to PAH (p=0.01). IPF patients exhibited significantly increased RBC shift oscillations compared to all other cohorts ($p \leq 0.01$)

Discussion $^{129}$Xe Biomarkers Distinguish Different Disease Phenotypes

In this study, unique $^{129}$Xe MR imaging and spectroscopy signatures for patients with COPD, IPF, PAH, and LHF were identified. COPD was characterized by significantly elevated ventilation and barrier defect percentages compared to all other disorders, as well as diminished RBC amplitude oscillations. However, in COPD ventilation defect percentage varied widely within the cohort, consistent with the heterogeneity of the disease. See, Pike et al., *Regional Heterogeneity of Chronic Obstructive Pulmonary Disease Phenotypes: Pulmonary He-3 Magnetic Resonance Imaging and Computed Tomography*. Copd-Journal of Chronic Obstructive Pulmonary Disease, 2016. 13(5): p. 601-609, the contents of which are hereby incorporated by reference as if recited in full herein. In contrast, IPF was characterized primarily by elevated barrier uptake, virtually absent barrier defect percentage, elevated RBC amplitude oscillations, and prominent oscillations in RBC shift. PAH and LHF presented with similar imaging characteristics (slight elevations in ventilation, barrier, and RBC defect percentages compared to healthy volunteers). However, PAH was distinguished from LHF by RBC amplitude oscillations that were lower than in healthy subjects, whereas in LHF such oscillations were enhanced. All four disease cohorts showed significant RBC transfer defects.

These imaging findings are consistent with previous studies that have identified increased ventilation defects in patients with COPD. See Wang et al., *Hyperpolarized* (129) *Xe gas transfer MRI: the transition from* 1.5*T to* 3*T*. Magn Reson Med, 2018; Qing et al., *Assessment of lung function in asthma and COPD using hyperpolarized* 129*Xe chemical shift saturation recovery spectroscopy and dissolved-phase MRI*. NMR Biomed, 2014. 27(12): p. 1490-501; and Virgincar et al., *Quantitative analysis of hyperpolarized* 129*Xe ventilation imaging in healthy volunteers and subjects with chronic obstructive pulmonary disease*. NMR Biomed, 2013. 26(4): p. 424-35, the contents of which are hereby incorporated by reference as if recited in full herein.

The observation that in COPD barrier uptake is also diminished is a new finding, likely reflecting emphysematous lung destruction and loss of surface area for gas exchange. This loss further leads to diminished RBC transfer. In IPF, the disease is characterized by increased barrier uptake with defects in RBC transfer primarily in the lung bases. See Kaushik et al., *Single-breath clinical imaging of hyperpolarized* (129)*Xe in the airspaces, barrier, and red blood cells using an interleaved* 3*D radial* 1-*point Dixon acquisition*. Magn Reson Med, 2016. 75(4): p. 1434-43; Kaushik et al., *Measuring diffusion limitation with a perfusion-limited gas—hyperpolarized* 129*Xe gas-transfer spectroscopy in patients with idiopathic pulmonary fibrosis*. J Appl Physiol, 2014. 117(6): p. 577-85; Wang et al., *Hyperpolarized* (129) *Xe gas transfer MRI: the transition from* 1.5*T to* 3*T*. Magn Reson Med, 2018; Wang et al., *Using hyperpolarized* (129)*Xe MRI to quantify regional gas transfer in idiopathic pulmonary fibrosis*. Thorax, 2018. 73(1): p. 21-28; and Kaushik et al., *Probing the regional distribution of pulmonary gas exchange through single-breath gas-and dissolved-phase Xe-*129 *MR imaging*. Journal of Applied Physiology, 2013. 115(6): p. 850-860, the contents of which are hereby incorporated by reference as if recited in full herein. Furthermore, the study provides important context for prior work showing that cardiogenic oscillations in $^{129}$Xe RBC amplitude and shift are significantly enhanced in patients with IPF relative to healthy controls. See Kaushik et al., *Measuring diffusion limitation with a perfusion-limited gas—hyperpolarized* 129*Xe gas-transfer spectroscopy in patients with idiopathic pulmonary fibrosis*. J Appl Physiol, 2014. 117(6): p. 577-85; and Bier et al., *A protocol for quantifying cardiogenic oscillations in dynamic* (129) *Xe gas exchange spectroscopy: The effects of idiopathic pulmonary fibrosis*. NMR Biomed, 2018: p. e4029, the contents of which are hereby incorporated by reference as if recited in full herein. Having now acquired such data in this broader cohort suggests that the RBC shift oscillations are, thus far, unique to IPF, and are not observed COPD, LHF, and PAH. Moreover, the enhanced RBC amplitude oscillations seen in in IPF are only additionally seen in LHF, suggesting that this is a marker of post-capillary PH.

Alveolar-Capillary Interface Models Depicting Disease Phenotypes

FIG. 20 illustrates diagrammatic conceptual architectures of the alveolar-capillary interface to aid in interpreting the $^{129}$Xe imaging and spectroscopic biomarkers across disease states. The diagrams illustrate the alveoli, capillary blood vessel, interstitial barrier tissues, RBCs, and $^{129}$Xe atoms. For each disease state the anticipated effect on the $^{129}$Xe biomarker (ventilation, barrier and RBC) is shown. These conceptual diagrams may aid in interpreting the patterns of $^{129}$Xe MRI and spectroscopic signatures of each disease in the context of gas transfer physiology, without limitation to the invention. In a healthy subject, $^{129}$Xe atoms freely diffuse into the alveoli and into the alveolar-capillary interface, translating into images reflecting a normal range of ventilation, barrier uptake and RBC transfer. In COPD, chronic airway inflammation and small airway obstruction create ventilation defects, while the loss of alveolar surface area associated with emphysema results in diminished uptake of $^{129}$Xe in the interstitial barrier tissues. See Barnes et al. *Systemic manifestations and comorbidities of COPD*. European Respiratory Journal, 2009. 33(5): p. 1165-1185, the contents of which are hereby incorporated by reference as if recited in full herein. This is associated with a concomitant decrease in RBC transfer, although many patients exhibit disproportionately worse RBC transfer that may reflect an additional loss of vasculature. See Rahaghi, F. N., E. J. R. van Beek, and G. R. Washko, *Cardiopulmonary Coupling in Chronic Obstructive Pulmonary Disease The Role of Imaging*. Journal of Thoracic Imaging, 2014. 29(2): p. 80-91, the contents of which are hereby incorporated by reference as if recited in full herein. By contrast, in IPF, interstitial fibrosis causes $^{129}$Xe uptake in barrier tissues to increase. See Lederer et al. *Idiopathic Pulmonary Fibrosis*. N Engl J Med, 2018. 379(8): p. 797-798, the contents of which are hereby incorporated by reference as if recited in full herein. This, in turn, causes diffusion limitation, which in addition to likely perfusion deficits, serves to decrease RBC transfer. See Wang, J. M., et al., *Using hyperpolarized* (129)*Xe MRI to quantify regional gas transfer in idiopathic pulmonary fibrosis*. Thorax, 2018. 73(1): p. 21-28, the contents of which are hereby incorporated by reference as if recited in full herein. When such destruction is accompanied by a preserved stroke volume, it will produce larger relative capillary blood volume oscillations between systole and diastole; this can manifest as larger RBC amplitude oscillations. In the setting of pulmonary hypertension (PH), left heart failure (LHF) is characterized by post-capillary impedance (predominantly from pulmonary venous PH). Because the high impedance originates downstream of the capillary beds, it is associated with larger capillary blood volume oscillations during the cardiac cycle, again resulting in larger spectroscopic RBC amplitude oscillations. It is less clear what causes the defects in RBC transfer, but it is known that LHF patients can develop gas exchange abnormalities including a decrease in DLCO that is thought to be secondary to chronic damage from pulmonary venous congestion. See Olson et al. *Impaired Pulmonary Diffusion in Heart Failure With Preserved Ejection Fraction*. Jacc-Heart Failure, 2016. 4(6): p. 490-498; and Guazzi, M., *Alveolar Gas Diffusion Abnormalities in Heart Failure*. Journal of Cardiac Failure, 2008. 14(8): p. 695-702, the contents of which are hereby incorporated by reference as if recited in full herein. And finally, it is contemplated that PAH can be characterized by increased pre-capillary impedance resulting from, inter alia, remodeling and obliteration of the pulmonary arterioles, which can result in a loss of alveolar membrane diffusing capacity and pulmonary capillary blood volume. See Farha et al., *Loss of alveolar membrane diffusing capacity and pulmonary capillary blood volume in pulmonary arterial hypertension*. Respiratory Research, 2013, 14, the contents of which are hereby incorporated by reference as if recited in full herein. While these features in PAH may not be expected to directly impact ventilation or diffusive barrier uptake, they can cause RBC transfer defects and increase impedance to flow occurring upstream of the capillary bed. This, in turn, can reduce the pulmonary capillary blood volume and the cardiogenic blood volume oscillations in the capillary bed. This can result in diminished RBC signal amplitude oscillations, which appears, at least at the present time, to be the feature that most strongly differentiates pre-capillary from post-capillary PH.

Differentiating Cardiopulmonary Diseases in the Clinical Setting

Figure 21:
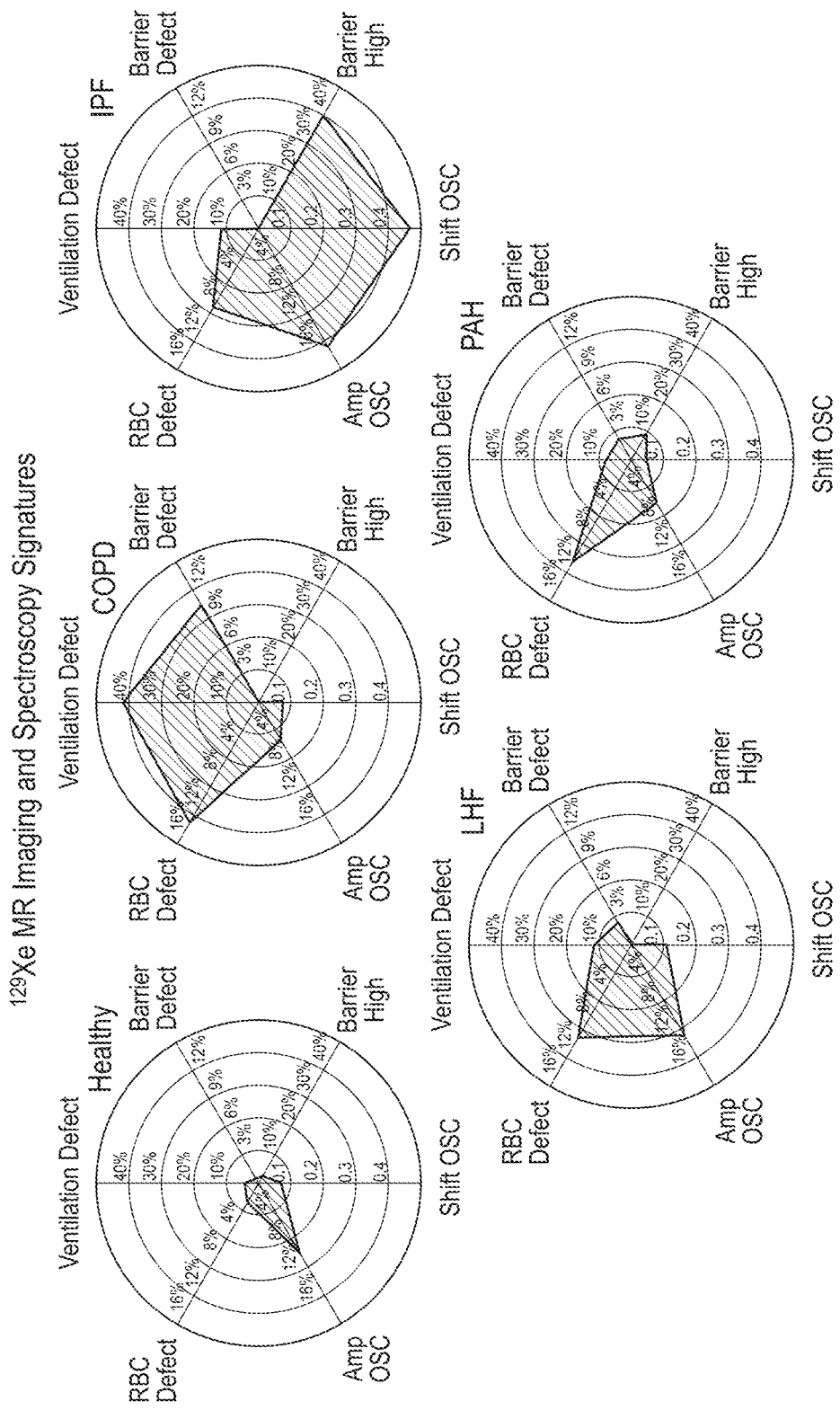
FIG. 21 is a set of radar plots illustrating $^{129}$Xe disease state and healthy signatures for patients with COPD, IPF, LHF and PAH based on $^{129}$Xe imaging and spectroscopic parameters/markers according to embodiments of the present invention.

Taken together, this combination of non-invasive $^{129}$Xe MR imaging and spectroscopic parameters allows interrogation of gas transfer at the alveolar capillary level that appears useful, not only for characterizing and quantifying disease burden, but identifying signatures that may help differentiate cardiopulmonary disorders, states or diseases. A potential output of this approach this is shown in FIG. 21, which shows radar plots (charts) of 4 key imaging features and 2 key spectroscopic features—ventilation defect, barrier defect, high barrier uptake, RBC defects, and RBC amplitude and shift oscillations. Integrating these features for each disease group can provide an initial graphic output of displaying these phenotypes in a visually distinct way. Generating such plots for individual patients can provide a powerful protocol to identify the primary phenotypes that should be considered. The radar chart is a graphical method of displaying multivariate $^{129}$Xe data in the form of a two-dimensional chart of three or more quantitative variables, with one or more different measurement units, such as percentage and ppm represented on axes starting from the same point. Of course, other outputs may be used such as, but not limited to, to a parallel coordinates plot, with the axes arranged radially.

In FIG. 21, the radar plots display the primary $^{129}$Xe MR imaging and spectroscopic signatures associated with patients with COPD, IPF, LHF, and PAH. Here the mean cohort values of the key markers are plotted on one of the 6 radials—ventilation defect, barrier defect, barrier high, RBC defect percentages derived from imaging, and RBC shift oscillation and amplitude oscillation from spectroscopy.

In addition to differentiating between various cardiopulmonary conditions, $^{129}$Xe MRI may be useful in determining the underlying cause of dyspnea in patients with mixed cardiopulmonary disease, e.g., in patients who have concomitant diseases. This is a common clinical situation in an aging population, where many individuals may have concomitant COPD and LHF that complicate ILD or PAH. See Hoeper et al., *Elderly patients diagnosed with idiopathic pulmonary arterial hypertension: results from the COMPERA registry*. Int J Cardiol, 2013. 168(2): p. 871-80, the contents of which are hereby incorporated by reference as if recited in full herein. Furthermore, as early diagnosis is increasingly emphasized in disorders such as ILD and PAH (see Cosgrove, G. P., et al., *Barriers to timely diagnosis of interstitial lung disease in the real world: the INTENSITY survey*. BMC Pulm Med, 2018. 18(1): p. 9; and Lau et al. *Early detection of pulmonary arterial hypertension*. Nat Rev Cardiol, 2015. 12(3): p. 143-55), $^{129}$Xe spectroscopic indices may provide a sensitive probe for early diagnosis and disease progression, the contents of which are hereby incorporated by reference as if recited in full herein. Furthermore, the RBC transfer signal depicts the ultimate disease burden for gas transfer function, and therefore might be used in evaluation of disease progression and therapy response. See Mammarappallil, J. G., et al., *New Developments in Imaging Idiopathic Pulmonary Fibrosis With Hyperpolarized Xenon Magnetic Resonance Imaging*. J Thorac Imaging, 2019. 34(2): p. 136-150, the contents of which are hereby incorporated by reference as if recited in full herein. Given the limitations of current diagnostic testing, the information provided by $^{129}$Xe gas transfer imaging and dynamic spectroscopy has the potential to improve patient care.

Study Comments

Several limitations apply to study of Example 2 when comparing $^{129}$Xe MR imaging and spectroscopic signatures across cardiopulmonary conditions. First, the heterogeneity and possible comorbidities of patients in each disease cohort may have limited the ability to identify patterns in $^{129}$Xe imaging and spectroscopy and contribute to variations in each group. For example, all PAH patients were undergoing PAH targeted treatment, and many did not have a recent right heart catheterization, which may have limited the severity of their PAH at the time of the $^{129}$Xe study. Furthermore, while this study aimed to recruit patients with isolated LHF as a model for post-capillary impedance, several may have also had right heart failure given the common pathogenic evolution from left heart dysfunction to right heart dysfunction over time. See Rosenkranz et al., *Left ventricular heart failure and pulmonary hypertension*. Eur Heart J, 2016. 37(12): p. 942-54, the contents of which are hereby incorporated by reference as if recited in full herein. In fact, this phenotypic evolution may partly explain the large variation in RBC amplitude oscillation exhibited by our LHF cohort (Max: 21.5%, Min: 8.0%, SD: 5.1%). Another limitation is that the subject scans were conducted at different platforms with two field strengths. The quantification method, using a healthy reference group constructed under the same acquisition protocol, was designed to incorporate the potential factors such as $T_1$ and $T_2^*$ decay, which may affect the gas transfer measurements. See Wang et al. *Quantitative analysis of hyperpolarized* 129 *Xe gas transfer MRI*. Med Phys, 2017. 44(6): p. 2415-2428, the contents of which are hereby incorporated by reference as if recited in full herein. However, these and other factors constrained the size of the healthy reference cohorts, which were also significantly younger than the typical patients in the cohorts. Since the aging lung is reported to undergo physiological changes that could impact gas transfer functions, future studies will benefit from constructing a larger and age-controlled healthy population. See Janssens, J. P., J. C. Pache, and L. P. Nicod, *Physiological changes in respiratory function associated with ageing*. Eur Respir J, 1999. 13(1): p. 197-205, the contents of which are hereby incorporated by reference as if recited in full herein.

Conclusions

In this Example 2 study, we applied $^{129}$Xe gas transfer imaging and spectroscopy on healthy subjects and patients with COPD, IPF, LHF, and PAH. As a non-invasive and non-ionizing tool, hyperpolarized $^{129}$Xe gas-transfer MRI provides a fundamentally new approach to directly image regional function while also capturing hemodynamics at the alveolar-capillary level. The identified unique imaging and spectroscopic signatures for each of these diseases may help overcome some of the diagnostic challenges faced by clinicians treating patients with cardiopulmonary disease. $^{129}$Xe gas transfer imaging and spectroscopy is a promising technology in characterizing cardiopulmonary disease pathophysiology and with further validation in larger studies, it is believed that this can contribute to a comprehensive understanding of the multifactorial pathogenesis of dyspnea and/or developing personalized treatment approaches.

Example 3

In this Example 3, experiments were carried out to evaluate whether pre-capillary (PAH) versus post-capillary (PHpost) origins of PH can be distinguished while accounting for concomitant lung disease like ILD or COPD.

In this study, regional gas exchange and hemodynamics with hyperpolarized $^{129}$Xe MRI were obtained. The study obtained single-breath 3D MRI images of ventilation, barrier and blood (RBC compartment) that identify defects in the gas exchange region of the lungs and single breath-dynamic spectroscopy of RBC peak amplitude and chemical shift (ppm) over time.

Experiment Subject Recruitment

Healthy: 22; ILD: 12: PAH: 10, Left Heart Failure: 6 (surrogate for post-capillary PH): COPD: 8.

Methods: Acquired $^{129}$Xe gas exchange imaging and dynamic spectroscopy for each subject.

Figures 22, 23, 24:
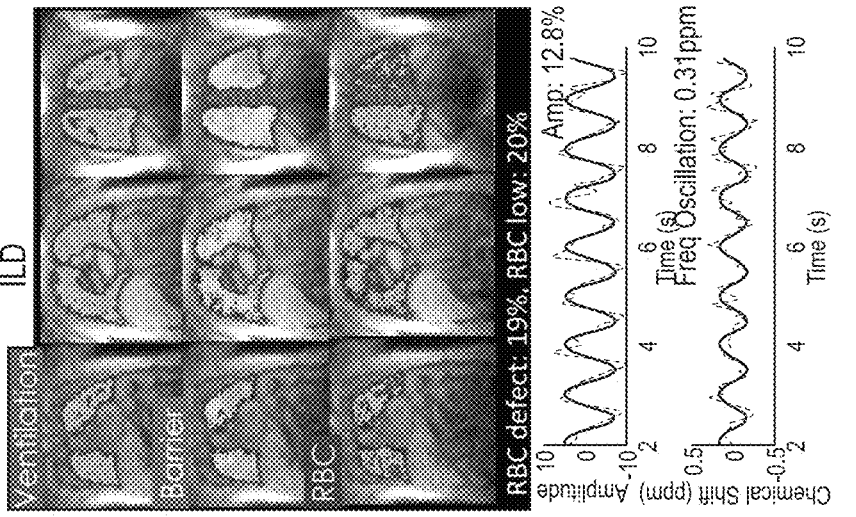
FIG. 22 are representative of ventilation, barrier and RBC images and associated amplitude and chemical shift spectra of healthy lungs according to embodiments of the present invention.
FIG. 23 are representative of ventilation, barrier and RBC images and associated amplitude and chemical shift spectra of a subject with PAH according to embodiments of the present invention.
FIG. 24 are representative of ventilation, barrier and RBC images and associated amplitude and chemical shift spectra of a subject with ILD according to embodiments of the present invention.

FIG. 22 are representative ventilation, barrier and RBC images and associated amplitude and chemical shift spectra of healthy lungs. The RBC defect was 2%, the RBC low: 5%. The peak amplitude was at 10.3% while the frequency oscillation was at 0.02 ppm.

FIG. 23 are representative of ventilation, barrier and RBC images and associated amplitude and chemical shift spectra of a subject with PAH. The RBC defect was 11%, the RBC low: 33%. The peak amplitude was at 4.3% while the frequency oscillation was at 0.06 ppm.

FIG. 24 are representative of ventilation, barrier and RBC images and associated amplitude and chemical shift spectra of a subject with ILD. The RBC defect was 19%, the RBC low: 20%. The peak amplitude was at 12.8% while the frequency oscillation was at 0.31 ppm.

Figure 25:
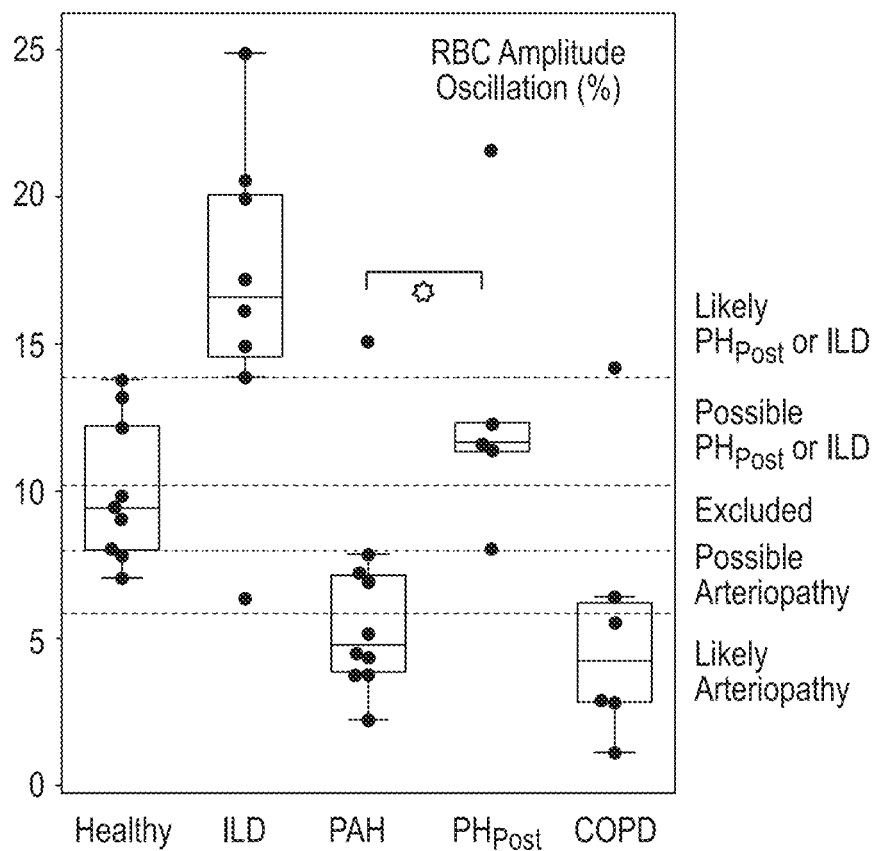
FIG. 25 is a graph of RBC amplitude oscillation (%) for healthy and different disease states of the lung(s) according to embodiments of the present invention.

RBC amplitude oscillations were used to identify healthy, pre- and post-capillary PH. FIG. 25 is a graph of RBC amplitude oscillation (%) for healthy and different disease states of the lung(s) including ILD, PAH, PHpost and COPD. As shown by the appended text at the right side of the graph, the various lines, from top (hightst RBC amplitude oscillation) to bottom (lowest), indicate likely PHpost or ILD, possible PHpost or ILD, excluded, possible arteriopathy, and likely ateriopathy.

Figure 26:
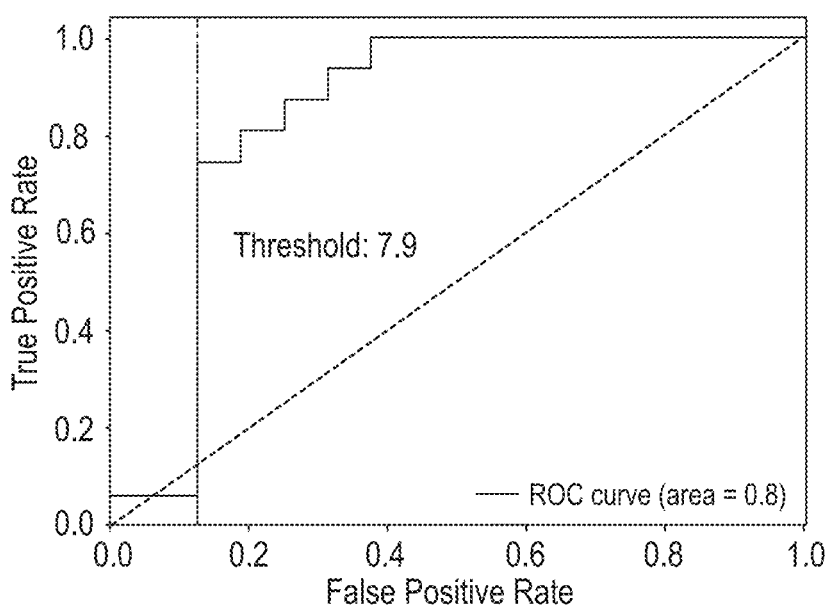
FIG. 26 is a graph of True Positive Rate versus False Positive Rate using ROC curve of RBC amplitude oscillation according to embodiments of the present invention.

FIG. 26 is a graph of True Positive Rate versus False Positive Rate using ROC curve of RBC amplitude oscillation to determine thresholds to separate/distinguish healthy, pre- and post-capillary PH. The ROC curve area is shown with best thresholds: 7.9

Figure 27:
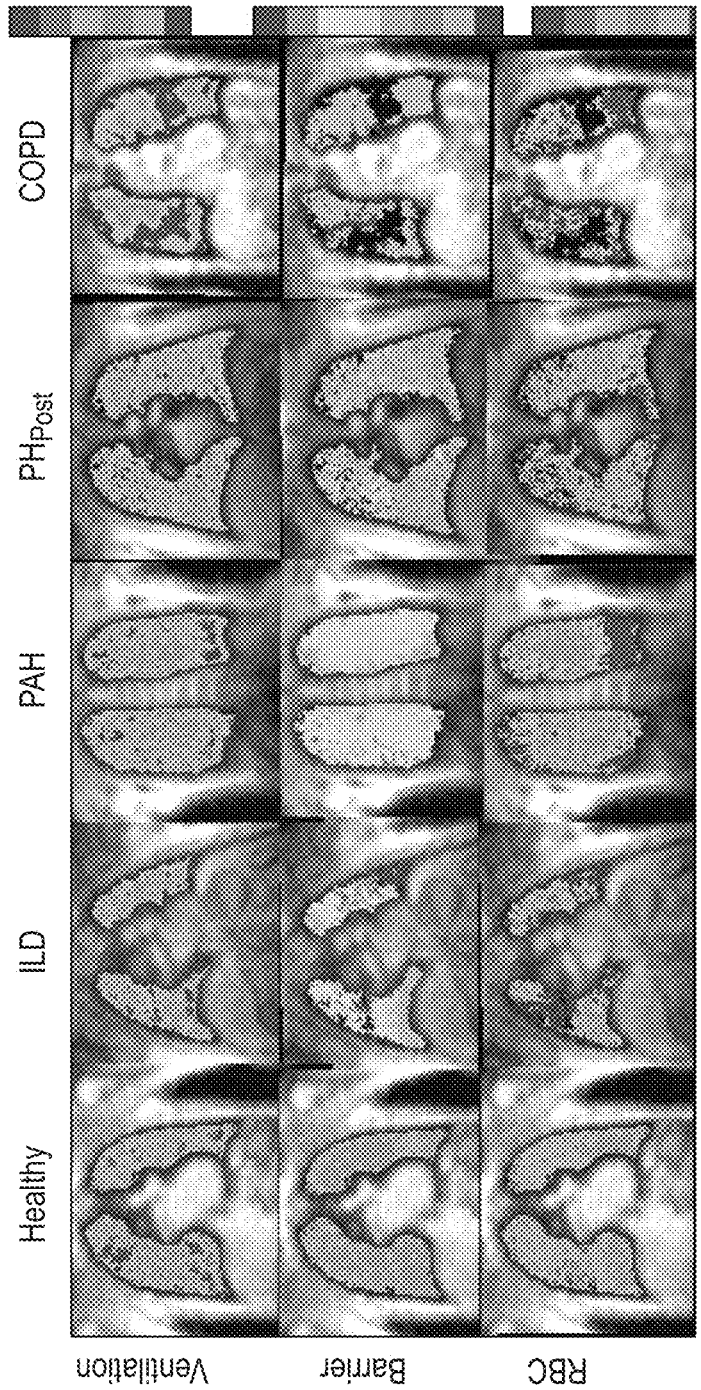
FIG. 27 is a set of 3D images (ventilation, barrier and RBC) of healthy and different disease cohorts illustrating metrics that can further distinguish the different disease cohorts according to embodiments of the present invention.

FIG. 27 is a set of 3D images (ventilation, barrier and RBC) of healthy and different disease cohorts illustrating lung maps showing metrics that can further distinguish the different disease cohorts (ILD, PAH, PHpost, COPD).

Figure 28:
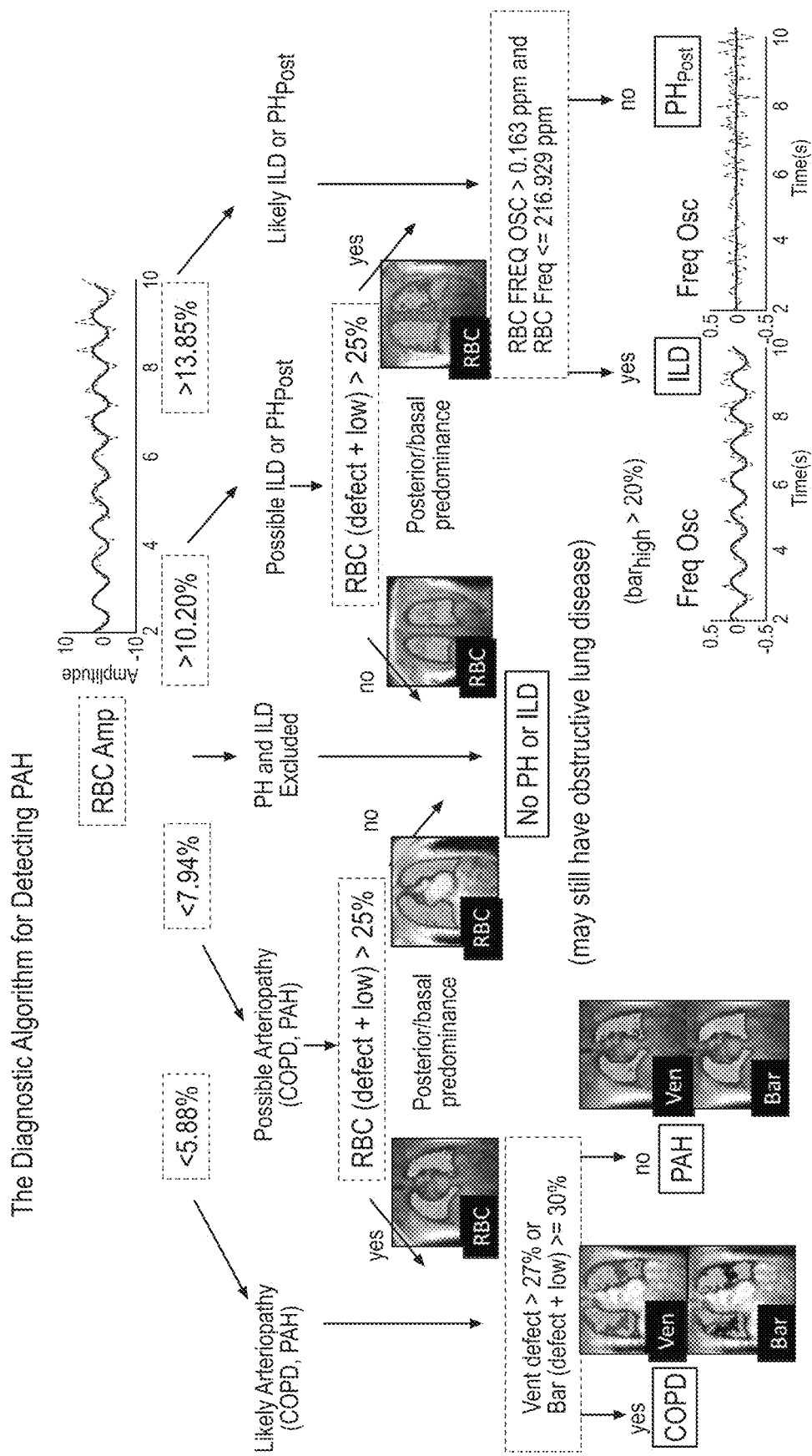
FIG. 28 is a schematic illustration of a diagnostic analysis protocol of defined parameters that can be used to identify a disease state according to embodiments of the present invention.

FIG. 28 is a schematic illustration of a diagnostic analysis protocol (i.e., model) of defined parameters that can be used to identify a disease state with ventilation, barrier and RBC defect percentages from the 3-D lung maps along with the dynamic spectroscopy parameters of RBC amplitude and frequency oscillations. The model correctly classified 34 of 40 subjects (85%) who had both imaging and spectroscopy data.

Figure 29:
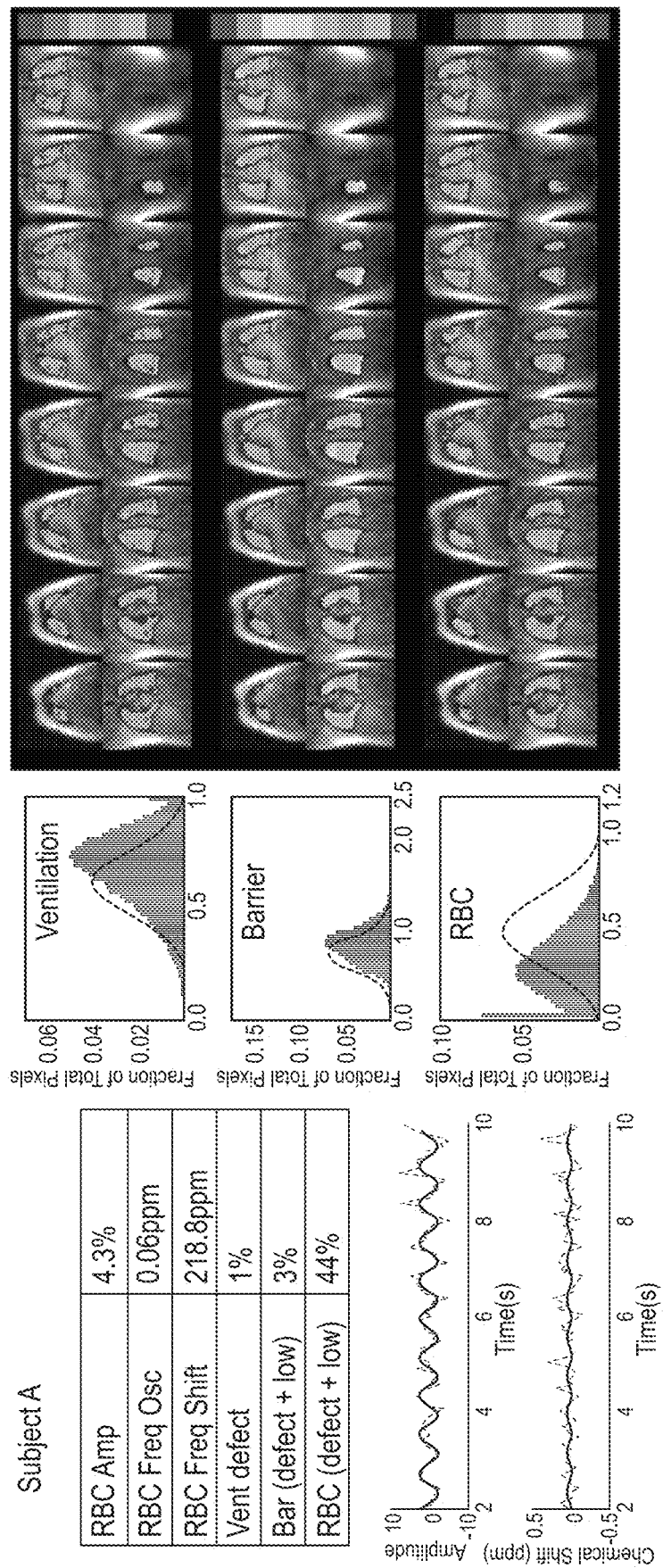
FIG. 29 is an example application of image and spectra metric parameters of Subject A that can be used for a diagnostic analysis protocol according to embodiments of the present invention.

FIG. 29 is an example application of image and spectra metric parameters of Subject A that was used for a diagnostic analysis protocol with ventilation, barrier and RBC defect percentages from the 3-D lung maps along with the dynamic spectroscopy parameters of RBC amplitude and RBC frequency oscillation.

Figure 30:
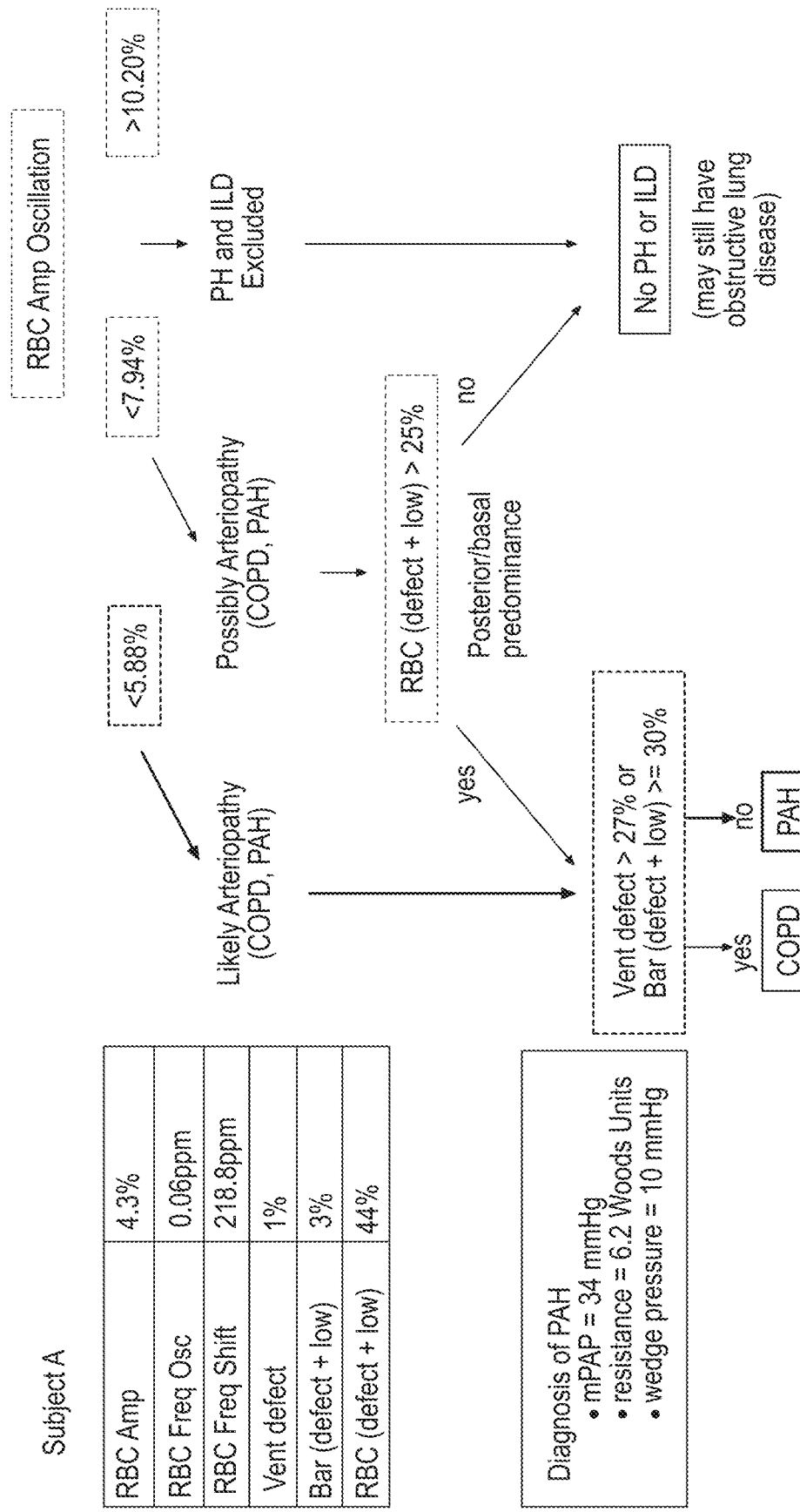
FIG. 30 illustrates the diagnostic analysis applied to the metric parameters of Subject A according to embodiments of the present invention.

FIG. 30 illustrates the diagnostic analysis applied to the metric parameters of Subject A illustrating various diagnostic decisions made based on RBC amplitude oscillation, RBC defect percentage, and ventilation and barrier defect percentages.

Figure 31:
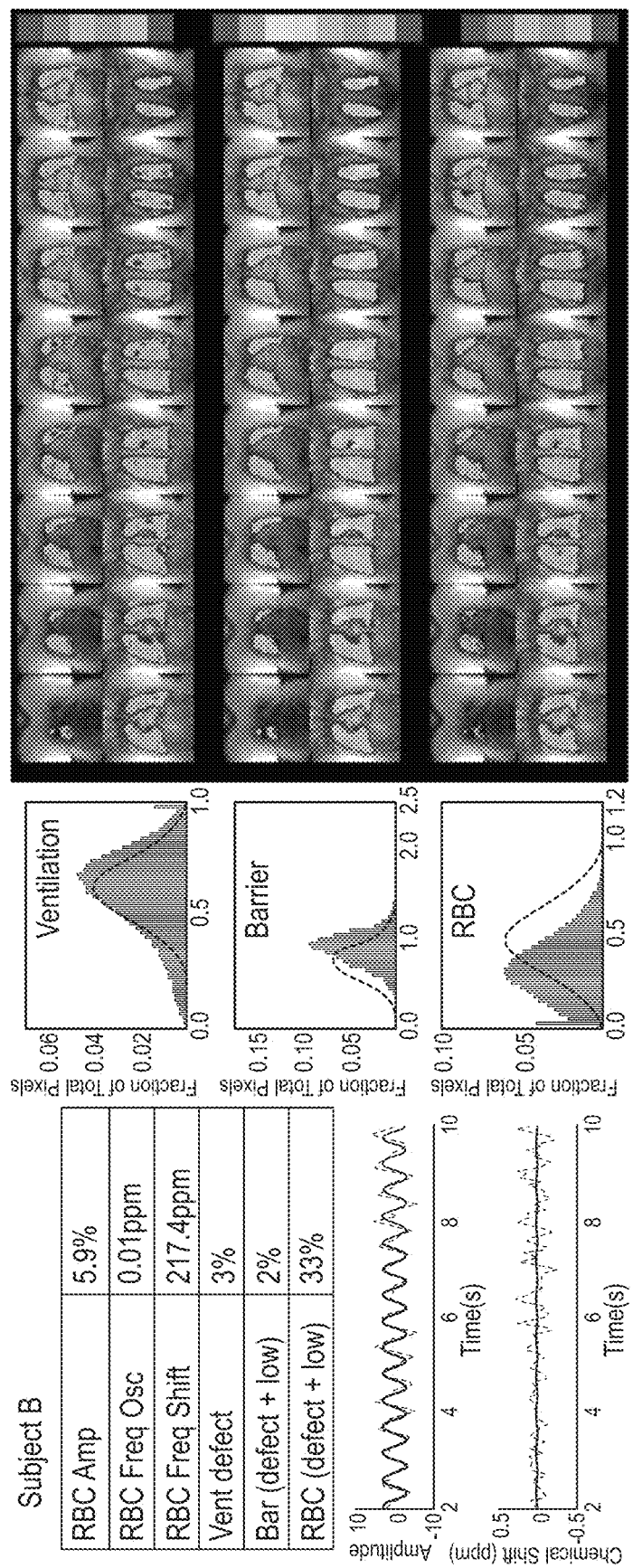
FIG. 31 is an example application of image and spectra metric parameters of Subject B that can be used for a diagnostic analysis protocol according to embodiments of the present invention.

FIG. 31 is an example application of image and spectra metric parameters of Subject B that used the diagnostic analysis protocol with ventilation, barrier and RBC defect percentages from the 3-D lung maps along with the dynamic spectroscopy parameters of RBC amplitude and RBC frequency oscillation.

Figure 32:
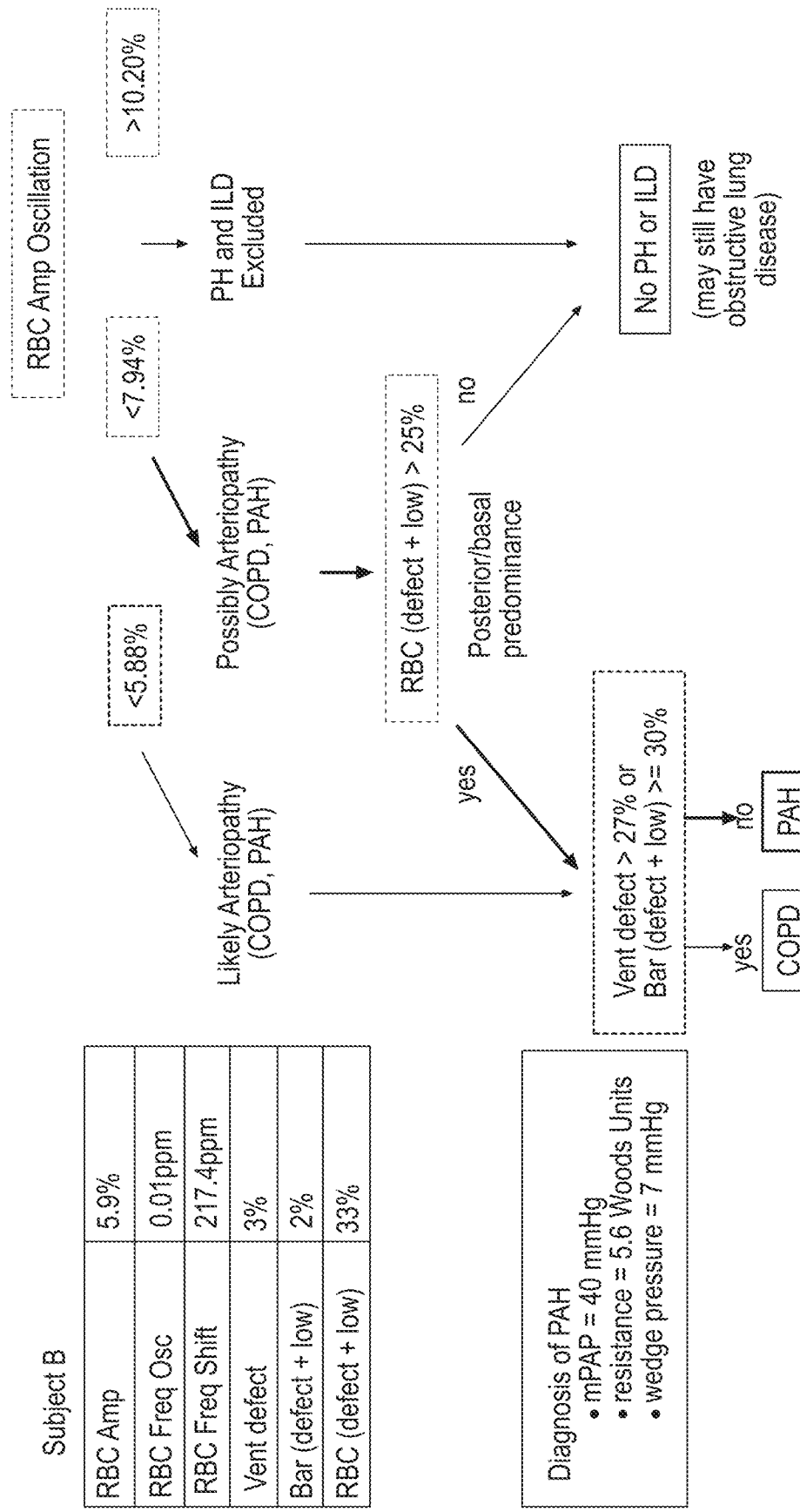
FIG. 32 illustrates the diagnostic analysis applied to the metric parameters of Subject B according to embodiments of the present invention.

FIG. 32 illustrates the diagnostic analysis applied to the metric parameters of Subject B illustrating various diagnostic decisions made based on RBC amplitude oscillation, RBC defect percentage, and ventilation and barrier defect percentages.

Conclusion, Example 3

The diagnostic analysis model shows promise to distinguish pre-capillary (PAH) versus post-capillary (PHpost) origins of PH, while accounting for concomitant lung disease such as ILD or COPD. It is noted that PAH patients were all on standard therapy, PH was not specifically ruled out from the ILD and COPD cohorts. In the future, prospective testing on a larger cohort undergoing same-day right heart catheterization as a gold standard to measure sensitivity and specificity for the ability of $^{129}$Xe metrics to detect PAH may be desireable.

In some embodiments of the present invention have been illustrated herein by way of example. Many variations and modifications can be made to the embodiments without substantially departing from the principles of the present invention. All such variations and modifications are intended to be included herein within the scope of the present invention, as set forth in the following claims.

That which is claimed:

1. A method of generating spectroscopy parameters for medical evaluation of a subject, comprising:
    obtaining a series of $^{129}$Xe free induction decays (FIDs) of a gas exchange region of a lung or lungs of the subject during a breathing maneuver;
    fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes; and
    electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:
    (i) barrier amplitude, barrier chemical shift (ppm), and one or more barrier FWHM (ppm) parameters; and
    (ii) the RBC amplitude, the RBC chemical shift (ppm), the RBC FWHM (ppm), and the RBC phase (degrees),
    wherein the static and dynamic $^{129}$Xe spectral parameters comprise RBC amplitude oscillations, RBC chemical shift oscillations, RBC FWHM oscillations and RBC phase oscillations, and
    correcting peak-to-peak amplitude of the RBC amplitude oscillations based at least in part on an estimated pulmonary exchange volume of the subject;
    wherein the method further comprises diagnosing a medical condition of the subject based on the static and dynamic $^{129}$Xe spectral parameters.

2. The method of claim 1, wherein the fitting is carried out with the $^{129}$Xe barrier resonance curve fitted as a Voigt line shape characterized by both a Lorentzian FWHM parameter and a Gaussian FWHM (FWHMG) (ppm) parameter and the $^{129}$Xe RBC resonance curve fitted using a Lorentzian line shape, wherein the diagnosing is carried out so that when RBC transfer defects are above a defined threshold along with when ventilation defects and/or barrier defects are below a defined threshold, in combination with when the corrected peak-to-peak amplitude of RBC amplitude oscillations is 7.9% or less, the subject is diagnosed as likely to have pre-capillary pulmonary hypertension, wherein the RBC transfer defects, the ventilation defects and the barrier defects are electronically automatically calculated from $^{129}$Xe Magnetic Resonance Imaging (MRI) gas exchange images of the lung or lungs of the subject, and wherein the corrected peak to peak amplitude of the RBC amplitude oscillations is carried out using the calculated RBC transfer defects.

3. The method of claim 1, further comprising detrending amplitudes of the $^{129}$Xe spectral parameters, then calculating peak-peak variation over time.

4. The method of claim 1, further comprising calculating temporal changes in signal amplitude of the RBC amplitude (A) as a percentage change from baseline (rbc_amp_percent) to generate the RBC amplitude oscillations:

$$rbc\_amp\_percent = (rbc\_amp - A^* \exp(-t/T1_{app}))/(A^* \exp(-t/T1_{app}))$$

where $T1_{app}$ is a T1 decay constant and t is time (seconds).

5. The method of claim 1, further comprising calculating temporal changes in signal amplitude of the RBC amplitude (A) using peak to peak analysis of a difference between a maximum and a minimum in the RBC amplitude oscillations.

6. The method of claim 1, further comprising normalizing the RBC amplitude oscillations to a barrier-phase or gas-phase $^{129}$Xe signal before or after the correcting step.

7. The method of claim 1, wherein the obtaining is at least partially in response to a pulse sequence with a repetition time (TR) in a range of about 20 ms-300 ms, and a flip angle of about 20-90 degrees to thereby provide increased sensitivity to cardiogenic oscillations.

8. The method of claim 1, wherein the obtaining is at least partially in response to a pulse sequence with a repetition time (TR) in a range of 200-300 ms and a flip angle in a range of 20-90 degrees.

9. The method of claim 1, further comprising obtaining gas exchange $^{129}$Xe Magnetic Resonance Imaging (MRI images of the lung or lungs of the subject and electronically calculating RBC transfer defect percentage, ventilation defect percentage and barrier defect percentage and high barrier uptake percentage from the gas exchange $^{129}$Xe MRI images,
wherein when the corrected RBC amplitude oscillations are at 7.9% or less, the subject is diagnosed as likely having pre-capillary pulmonary hypertension, and
wherein when the corrected RBC amplitude oscillations are at least 1.5X larger than a healthy cohort and/or the high barrier uptake percentage is at or above 20%, the subject is diagnosed as likely having Idiopathic pulmonary fibrosis (IPF).

10. The method of claim 1, wherein data from the obtained series of $^{129}$Xe FIDs is acquired between every 20 ms to every 300 ms during the breathing maneuver, and wherein the breathing maneuver includes a breath-hold over a time period of about 10-30 seconds.

11. The method of claim 1, wherein the fitting is carried out with each of the $^{129}$Xe RBC resonance, the $^{129}$Xe barrier resonance and the $^{129}$Xe gas-phase resonance characterized by 4 spectral parameters: amplitude ($\alpha$), frequency ($f$), phase ($\varphi$), and Lorentzian linewidth (FWHM), and, for the barrier resonance, a 5th parameter, a Gaussian linewidth (FWHMG), is also extracted, and wherein the fitting is carried out with the barrier resonance initialized with respective initial Lorentzian and Gaussian linewidths, and wherein the fitting is carried out using the below equation:

$$S_{fit} = a_{rbc} e^{i\varphi_{rbc} + 2\pi i f_{rbc} t} e^{-\pi t \times FWHM_{rbc}} + \\ a_{bar} e^{i\varphi_{bar} + 2\pi i f_{bar} t} e^{-\pi t \times FWHM_{bar}} e^{-4ln2 \times t^2 FWHMG_{bar}^2} + \\ a_{gas} e^{i\varphi_{gas} + 2\pi i f_{gas} t} e^{-\pi t \times FWHM_{gas}} \quad \text{EQN(1)}$$

12. The method of claim 1, further comprising transmitting data of the obtained series of $^{129}$Xe free induction decays (FIDs) from an imaging site with a Magnetic Resonance Imaging (MRI) scanner to a remote server, wherein the remote server performs the fitting and generating actions, and wherein the remote server comprises or is in communication with a database of defined different disease pattern signatures of the $^{129}$Xe spectral parameters correlated to pulmonary hypertension and interstitial lung diseases.

13. The method of claim 1, further comprising:
electronically obtaining a plurality of $^{129}$Xe imaging parameters of the lung or lungs of the subject including RBC defect percentage, ventilation defect percentage, barrier defect percentage and high barrier uptake percentage;
generating at least one radar plot illustrating a disease state of the subject, wherein the radar plot comprises ventilation defect percentage, barrier defect percentage, RBC defect percentage, high barrier uptake percentage, RBC amplitude oscillation and chemical shift oscillation, based on the plurality of $^{129}$Xe imaging parameters and the $^{129}$Xe spectral parameters; and
identifying whether the subject has a cardiopulmonary disease based on the at least one radar plot.

14. The method of claim 1, wherein, before the obtaining step, the method further comprises providing gas phase hyperpolarized $^{129}$Xe to the subject.

15. The method of claim 1, further comprising electronically evaluating a value of one or more of the static $^{129}$Xe spectral parameters in combination with one or more of the dynamic $^{129}$Xe spectral parameters to evaluate one or more different disease states and/or conditions, wherein one or more of the static $^{129}$Xe spectral parameters is derived from spectra obtained over only a first portion of a breath hold of the breathing maneuver.

16. The method of claim 1, further comprising treating a medical condition identified based on a plurality of the generated $^{129}$Xe spectral parameters.

17. The method of claim 1, wherein a static $^{129}$Xe spectral parameter is an RBC/barrier ratio and has a mean value for a healthy subject of 0.58±0.12.

18. The method of claim 1, further comprising, before and/or during the fitting step, extracting temporal variations in $^{129}$Xe RBC resonance occurring at a cardiac frequency.

19. The method of claim 18, wherein the breathing maneuver comprises a breath-hold action, the method further comprising correcting amplitude of the plot of RBC amplitude for magnetization decays caused by T1 and radio frequency (RF)-induced depolarization during a breath-hold period of the breath-hold action of the breathing maneuver by dividing the RBC amplitude "A" by a calculated apparent T1 decay constant (T1app), wherein T1app is quantified by fitting RBC amplitude over time "t" to $e^{-t/T1app}$.

20. The method of claim 1, further comprising, before the fitting and generating steps, pre-processing raw FIDs by Fourier transforming raw data along an indirect time domain with respect to a breath hold time period of a breath hold of the breathing maneuver, retaining only coefficients that exceed a defined threshold, then Fourier transforming back along an indirect frequency domain to provide an FID with increased SNR relative to raw FIDs for the fitting to thereby filter non-dominant frequencies out of the indirect time domain providing time domain filtered FIDs to smooth temporal changes between different FIDs, while leaving spectral-frequency domain intact.

21. The method of claim 20, further comprising using a FID sliding boxcar window filter and averaging a plurality of the time domain filtered FIDs to provide an FID with increased SNR for the fitting.

22. The method of claim 1, further comprising electronically comparing oscillations of one or more of the RBC amplitude oscillations, the RBC chemical shift oscillations, the RBC FWHM oscillations and the RBC phase oscillations pre and post-administration of a pharmaceutical agent and identifying vascular reactivity and/or change based on changes in corresponding RBC oscillations.

23. The method of claim 22, wherein the pharmaceutical agent comprises prostacyclin.

24. The method of claim 22, wherein the pharmaceutical agent is a vasodilator.

25. The method of claim 24, wherein the vasodilator is an inhaled vasodilator.

26. An MRI scanner system, comprising:
a Magnetic Resonance Imaging (MRI) scanner; and
at least one processor in communication with the MRI scanner and configured to carry out a method of generating spectroscopy parameters for medical evaluation of a subject, comprising:
obtaining a series of $^{129}$Xe free induction decays (FIDs) of a gas exchange region of a lung or lungs of the subject during a breathing maneuver;
fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes; and
electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:
(i) barrier amplitude, barrier chemical shift (ppm), and one or more barrier FWHM (ppm) parameters; and
(ii) the RBC amplitude, the RBC chemical shift (ppm), the RBC FWHM (ppm), and the RBC phase (degrees),
wherein the static and dynamic $^{129}$Xe spectral parameters comprise RBC amplitude oscillations, RBC chemical shift oscillations, RBC FWHM oscillations and RBC phase oscillations, and
correcting peak-to-peak amplitude of the RBC amplitude oscillations based at least in part on an estimated pulmonary exchange volume of the subject;
wherein the method further comprises diagnosing a medical condition of the subject based on the static and dynamic $^{129}$Xe spectral parameters.

27. A medical evaluation system comprising a server in communication with at least one Magnetic Resonance Imaging (MRI) scanner and having at least one processor that carries out a method of generating spectroscopy parameters for medical evaluation of a subject, comprising:
obtaining a series of $^{129}$Xe free induction decays (FIDs) of a gas exchange region of a lung or lungs of the subject during a breathing maneuver;
fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes; and
electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:
(i) barrier amplitude, barrier chemical shift (ppm), and one or more barrier FWHM (ppm) parameters; and
(ii) the RBC amplitude, the RBC chemical shift (ppm), the RBC FWHM (ppm), and the RBC phase (degrees),
wherein the static and dynamic $^{129}$Xe spectral parameters comprise RBC amplitude oscillations, RBC chemical shift oscillations, RBC FWHM oscillations and RBC phase oscillations, and
correcting peak-to-peak amplitude of the RBC amplitude oscillations based at least in part on an estimated pulmonary exchange volume of the subject;
wherein the method further comprises diagnosing a medical condition of the subject based on the static and dynamic $^{129}$Xe spectral parameters.

28. A method of generating spectroscopy parameters, comprising:
providing an inhalable hyperpolarized $^{129}$Xe gas to a subject;
obtaining, from a Magnetic Resonance Imaging (MRI) scanner, a series of $^{129}$Xe free induction decays (FIDs) of a gas exchange region of a lung or lungs of the subject during a breathing maneuver while the subject is held in a bore of a magnet of the MM scanner;
electronically fitting the FIDs with a curve fitting function modeled with one or more non-Lorentzian line shapes;
electronically generating a plurality of $^{129}$Xe spectral parameters based on the fitting, wherein the plurality of $^{129}$Xe spectral parameters include static and/or dynamic $^{129}$Xe spectral parameters using plots over time of:
(i) barrier amplitude, barrier chemical shift (ppm), and one or more barrier full width at half maximum (FWHM)(ppm) parameters; and (ii) red blood cell (RBC) amplitude, RBC chemical shift (ppm), RBC FWHM (ppm), and RBC phase (degrees); and electronically adjusting amplitude "ARBc" of the RBC amplitude plot by multiplying by:

(V_stroke_ref/V_stroke)*(PEV/PEV_ref), where V stroke ref is a reference stroke volume, V stroke is a subject's actual stroke volume, PEV ref is a reference pulmonary exchange volume, and PEV is the subject's measured pulmonary exchange volume.

29. A computer system for electronic medical evaluation of lungs of a plurality of different subjects, the computer system comprising at least one processor configured to:

obtain a series of $^{129}$Xe free induction decays (FIDs) of a gas exchange region of a lung or lungs of a respective subject during a breathing maneuver;

fit the FIDs with a curve fitting function modeled with one or more non-Lorentzian line shapes;

electronically generate a plurality of $^{129}$Xe spectral parameters based on the curve fitting, wherein the plurality of $^{129}$Xe spectral parameters include static and/or dynamic $^{129}$Xe spectral parameters using plots over time of:

(i) barrier amplitude, barrier chemical shift (ppm), and one or more barrier full width at half maximum (FWHM)(ppm) parameters; and (ii) red blood cell (RBC) spectral parameters comprising RBC amplitude, RBC chemical shift (ppm), RBC FWHM (ppm), and RBC phase (degrees);

high-pass filter each of the RBC amplitude, RBC chemical shift, RBC phase and RBC FWHM with a 0.5 Hz cutoff frequency to thereby remove residual baseline variation and provide filtered parameter plots of the RBC spectral parameters; and provide the filtered parameter plots of the RBC spectral parameters to an image processing circuit configured to analyze the filtered parameter plots of the RBC spectral parameters to determine if the respective subject has one or more cardiopulmonary conditions and/or a lung impairment or disease.

30. The computer system of claim 29, wherein the at least one processor is further configured to fit the filtered parameter plots to a sinusoid with phase offset:

$$\frac{1}{2} A_{pk-pk} \sin(2\pi f_c t + \varphi),$$

where $A_{pk-pk}$ is the peak-to-peak amplitude, $f_c$ the cardiac frequency, t is time in seconds, and pp is a phase off-set, and where $f_c$ is cardiac frequency that is derived from the subject's RBC amplitude oscillations.

31. The computer system of claim 30, wherein $f_c$ is used in temporal fits of other RBC spectral parameters including RBC chemical shift, linewidth, and phase.

32. A method of non-invasively screening a subject for one or more cardiopulmonary conditions, comprising:

obtaining a series of $^{129}$Xe free induction decays (FIDs) of a gas exchange region of a lung or lungs of the subject during a breathing maneuver;

fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes;

electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:

(i) barrier amplitude, barrier chemical shift (ppm), and one or more barrier FWHM (ppm) parameters; and (ii) the RBC amplitude, the RBC chemical shift (ppm), the RBC FWHM (ppm), and the RBC phase (degrees), wherein the static and dynamic $^{129}$Xe spectral parameters comprise RBC amplitude oscillations, RBC chemical shift oscillations, RBC FWHM oscillations and RBC phase oscillations;

obtaining $^{129}$Xe Magnetic Resonance Imaging (MRI) gas exchange images of the lung or lungs of the subject;

electronically calculating RBC transfer defects, ventilation defects and barrier defects from the $^{129}$Xe Magnetic Resonance Imaging (MM) gas exchange images of the lung or lungs of the subject and electronically providing a database comprising a plurality of defined different disease patterns, wherein the plurality of defined disease patterns comprise:

pre-capillary pulmonary hypertension defined at least in part by a respective defined disease pattern comprising peak-to-peak amplitude of RBC amplitude oscillations that is 7.9% or less, and post-capillary vascular disease defined at least in part by a respective defined disease pattern comprising peak-to-peak amplitude of RBC amplitude oscillations that is greater than 13.85%.

33. The method of claim 32, further comprising electronically evaluating the generated $^{129}$Xe spectral parameters to identify whether the subject has one or more of the defined different disease patterns.

34. The method of claim 32, wherein one or more of the defined different disease patterns comprises oscillations of the RBC amplitude oscillations, the RBC chemical shift oscillations, the RBC FWHM oscillations or the RBC phase oscillations that exceeds a defined peak-to-peak threshold.

35. The method of claim 32, wherein one or more of the defined different disease patterns comprises at least one feature of the RBC amplitude oscillations and the RBC chemical shift oscillations having peak-to-peak variation that is below a defined peak-to-peak threshold.

36. The method of claim 32, wherein one or more of the defined different disease patterns is based on a shape of oscillations of at least one of the RBC amplitude oscillations, the RBC chemical shift oscillations, the RBC FWHM oscillations and the RBC phase oscillations.

37. The method of claim 32, wherein at least one of the defined disease patterns has a disease pattern comprising an RBC frequency shift obtained during a first second of a breath hold of the breathing maneuver that is lower than a defined norm.

38. The method of claim 32, wherein one or more of the defined different disease patterns identify combined pre- and post-capillary vascular disease.

39. The method of claim 32, wherein one disease pattern of the defined disease patterns that is associated with Idiopathic pulmonary fibrosis (IPF) is at least partially characterized by an RBC chemical shift (ppm) that is below a defined ppm.

40. The method of claim 32, further comprising identifying combined pre- and post-capillary vascular disease by a respective defined disease pattern defined by one or more of a size, shape or frequency of at least two of the RBC amplitude oscillations, the RBC chemical shift oscillations, the RBC FWHM oscillations or the RBC phase oscillations.

41. A method of generating spectroscopy parameters for medical evaluation of a subject, comprising:
   obtaining a series of $^{129}$Xe free induction decays (FIDs) of a gas exchange region of a lung or lungs of the subject during a breathing maneuver;
   fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes; and
   electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:
   (i) barrier amplitude, barrier chemical shift (ppm), and one or more barrier FWHM (ppm) parameters; and
   (ii) the RBC amplitude, the RBC chemical shift (ppm), the RBC FWHM (ppm), and the RBC phase (degrees),
   wherein the static and dynamic $^{129}$Xe spectral parameters comprise RBC amplitude oscillations, RBC chemical shift oscillations, RBC FWHM oscillations and RBC phase oscillations;
   electronically providing a database comprising a plurality of defined different disease patterns of the $^{129}$Xe spectral parameters correlated to different pulmonary hypertension and/or interstitial lung diseases, wherein at least some of the plurality of defined disease patterns comprise defined sets of one or more features of at least two of the RBC amplitude oscillations, the RBC chemical shift oscillations, the RBC FWHM oscillations and the RBC phase oscillations; and
   wherein, when the RBC amplitude oscillations are at least 1.5X larger than a healthy cohort, and when the RBC (chemical shift) oscillations and the RBC phase oscillations are at least 2X above a healthy cohort, identifying that the subject has Idiopathic pulmonary fibrosis (IPF).

42. A method of generating spectroscopy parameters for medical evaluation of a subject, comprising:
   obtaining a series of $^{129}$Xe free induction decays (FIDs) of a gas exchange region of a lung or lungs of the subject during a breathing maneuver;
   fitting real and imaginary components of the FIDs in a time domain with a curve fitting function modeled with one or more non-Lorentzian line shapes, wherein the curve fitting function models each of a $^{129}$Xe barrier resonance, a $^{129}$Xe gas-phase resonance and a $^{129}$Xe red blood cell (RBC) resonance, with the $^{129}$Xe barrier resonance modeled, at least in part, with the one or more non-Lorentzian line shapes; and
   electronically generating a plurality of $^{129}$Xe spectral parameters comprising RBC spectral parameters of RBC amplitude, RBC chemical shift (ppm), RBC full width at half maximum (FWHM) (ppm) and RBC phase (degrees) based on the fitting, wherein the plurality of $^{129}$Xe spectral parameters include static and dynamic $^{129}$Xe spectral parameters using plots over time of at least one of:
   (i) barrier amplitude, barrier chemical shift (ppm), and one or more barrier FWHM (ppm) parameters; and
   (ii) the RBC amplitude, the RBC chemical shift (ppm), the RBC FWHM (ppm), and the RBC phase (degrees),
   wherein the static and dynamic $^{129}$Xe spectral parameters comprise RBC amplitude oscillations, RBC chemical shift oscillations, RBC FWHM oscillations and RBC phase oscillations;
   electronically providing a database comprising a plurality of defined different disease patterns of the $^{129}$Xe spectral parameters correlated to different pulmonary hypertension and/or interstitial lung diseases, wherein at least some of the plurality of defined disease patterns comprise defined sets of one or more features of at least two of the RBC amplitude oscillations, the RBC chemical shift oscillations, the RBC FWHM oscillations and the RBC phase oscillations; and
   wherein when the RBC chemical shift oscillations are more than 5-fold higher than a healthy cohort, and when the RBC phase oscillations are more than 5-fold higher than the healthy cohort, identifying that the subject has Idiopathic pulmonary fibrosis (IPF).

43. A method of identifying whether a patient has one or more defined medical conditions using $^{129}$Xe spectral parameters, comprising:
   obtaining a series of $^{129}$Xe free induction decays (FIDs) of a gas exchange region of a lung or lungs of a patient during a breathing maneuver;
   fitting the FIDs in a time domain with a curve fitting function modeled with one or more non-Lorentzian line shapes, wherein the curve fitting function models each of a barrier resonance, a red blood cell (RBC) resonance and a gas-phase resonance;
   electronically generating a plurality of static and dynamic $^{129}$Xe spectral parameters based on the fitting of a plurality of RBC spectral parameters comprising RBC amplitude, RBC chemical shift (ppm), RBC full width at half maximum (FWHM) (ppm), and RBC phase (degrees), wherein the dynamic $^{129}$Xe spectral parameters comprise oscillations of the plurality of the RBC spectral parameters as at least some of the dynamic $^{129}$Xe spectral parameters;
   electronically evaluating one or more of a defined shape, pattern, peak size, and/or a frequency of the oscillations of at least two of the RBC amplitude, the RBC chemical shift (ppm), the RBC FWHM (ppm), and the RBC phase (degrees);
   electronically calculating RBC transfer defect percentage, ventilation defect percentage, barrier defect percentage and high barrier uptake percentage using data from $^{129}$Xe Magnetic Resonance Imaging (MM) gas exchange images of the lung or lungs of the patient and
   identifying whether the patient has one or more of the defined medical conditions based on the electronic evaluation,
   wherein based at least in part on when peak-to-peak amplitude of the oscillations of the RBC amplitude is 7.9% or less, the patient is identified as likely having pre-capillary pulmonary hypertension, and
   wherein based at least in part on when peak-to-peak amplitude of the oscillations of the RBC amplitude is greater than 10.2% and/or when high barrier uptake percentage is at or above 20%, the patient is identified as likely having Idiopathic pulmonary fibrosis (IPF).

44. The method of claim 43, wherein the plurality of static and dynamic $^{129}$Xe spectral parameters comprise oscillations of the RBC chemical shift and the RBC phase.

45. The method of claim 43, wherein the static $^{129}$Xe spectral parameters are derived from spectra obtained over only about a first second of a breathhold of the breathing maneuver.

46. The method of claim 43, wherein the static and dynamic $^{129}$Xe spectral parameters further comprise (i) a RBC/barrier ratio and (ii) a value of RBC chemical shift calculated based averages of signal over only about a first second of a breathhold of the breathing maneuver.

47. The method of claim 43, further comprising correcting the peak-to-peak amplitude of the RBC amplitude oscillations based on a calculated pulmonary exchange volume of the patient using the ventilation defect percentage and/or the RBC transfer defect percentage, wherein when the corrected peak-to-peak amplitude of the oscillations of the RBC amplitude is 7.9% or less, the patient is identified as likely having pre-capillary pulmonary hypertension.

48. The method of claim 43, wherein the static and dynamic $^{129}$Xe spectral parameters further comprise barrier $^{129}$Xe spectral parameters using plots over time of barrier amplitude, barrier chemical shift (ppm), and one or more barrier FWHM (ppm).

49. The method of claim 48, wherein the static and dynamic $^{129}$Xe spectral parameters further comprise gas-phase $^{129}$Xe spectral parameters using plots over time of gas phase amplitude, gas phase chemical shift (ppm), gas FWHM (ppm), and gas phase (degrees).

* * * * *

UNITED STATES PATENT AND TRADEMARK OFFICE
CERTIFICATE OF CORRECTION

PATENT NO. : 11,944,424 B2
APPLICATION NO. : 16/406630
DATED : April 2, 2024
INVENTOR(S) : Bier et al.

It is certified that error appears in the above-identified patent and that said Letters Patent is hereby corrected as shown below:

In the Specification

Column 2, Line 30: Please correct "$^{12}9Xe$" to read --$^{129}Xe$--

Column 4, Line 11: Please correct "ApRc" to read --$A_{RBC}$--

Column 8, Lines 3-4: Please remove the paragraph break between "(percent)." and "FIG. 5B"

Column 9, Line 25: Please correct "A amplitude" to read --$\Delta$ amplitude--

Column 9, Line 28: Please correct "A shift" to read --$\Delta$ shift--

Column 30, Line 67: Please correct "5.80." to read --5.8°.--

Column 34, Line 52: Please correct "$^{12}9Xe$" to read --$^{129}Xe$--

In the Claims

Column 45, Line 4, Claim 2: Please correct "(FWHMG)" to read --(FWHM$_G$)--

Column 46, Line 7, Claim 11: Please correct "(FWHMG)" to read --(FWHM$_G$)--

Column 47, Line 5, Claim 19: Please correct "(T1app)" to read --(T1app)--

Column 49, Line 4, Claim 28: Please correct ""ARBc"" to read --"$A_{RBC}$"--

Column 49, Line 8, Claim 28: Please correct "V stroke ref is a reference stroke volume, V stroke" to read --V_stroke_ref is a reference stroke volume, V_stroke--

Signed and Sealed this
Ninth Day of July, 2024

Katherine Kelly Vidal
*Director of the United States Patent and Trademark Office*

Column 49, Line 9, Claim 28: Please correct "PEV ref" to read --PEV_ref--

Column 49, Line 51, Claim 30: Please correct "pp" to read --$\varphi$--

Column 50, Line 23, Claim 32: Please correct "(MM)" to read --(MRI)--

Column 50, Line 24, Claim 32: Please correct "subject and" to read --subject; and--

Column 52, Line 56, Claim 43: Please correct "(MM)" to read --(MRI)--

Column 52, Line 57, Claim 43: Please correct "patient and" to read --patient; and--